United States Patent
Ben-Yakar et al.

(10) Patent No.: US 9,333,036 B2
(45) Date of Patent: May 10, 2016

(54) SYSTEMS, DEVICES AND METHODS FOR IMAGING AND SURGERY

(75) Inventors: Adela Ben-Yakar, Austin, TX (US); Christopher L. Hoy, Leiden (NL); William Neil Everett, Cedar Park, TX (US); James B. Kobler, West Roxbury, MA (US); Richard Rox Anderson, Boston, MA (US); William A. Farinelli, Danvers, MA (US); Steven M. Zeitels, Newton, MA (US)

(73) Assignees: Board of Regents, The University of Texas System, Austin, TX (US); The General Hospital Corporation, Boston, MA (US)

( * ) Notice: Subject to any disclaimer, the term of this patent is extended or adjusted under 35 U.S.C. 154(b) by 161 days.

(21) Appl. No.: 13/574,472

(22) PCT Filed: Jan. 21, 2011

(86) PCT No.: PCT/US2011/022099
§ 371 (c)(1),
(2), (4) Date: Jan. 14, 2013

(87) PCT Pub. No.: WO2011/091283
PCT Pub. Date: Jul. 28, 2011

(65) Prior Publication Data
US 2013/0211391 A1  Aug. 15, 2013

Related U.S. Application Data

(60) Provisional application No. 61/297,532, filed on Jan. 22, 2010.

(51) Int. Cl.
*A61B 18/20* (2006.01)
*A61B 17/00* (2006.01)

(52) U.S. Cl.
CPC ....... *A61B 18/20* (2013.01); *A61B 2017/00057* (2013.01); *A61B 2018/2085* (2013.01)

(58) Field of Classification Search
CPC ........... A61B 18/20; A61B 2018/2085; A61B 2017/00057
USPC ..................................................... 607/88–94
See application file for complete search history.

(56) References Cited

U.S. PATENT DOCUMENTS

| | | |
|---|---|---|
| 5,112,328 A | 5/1992 | Taboada et al. |
| 5,178,616 A | 1/1993 | Uemiya et al. |

(Continued)

FOREIGN PATENT DOCUMENTS

| | | |
|---|---|---|
| GB | 2338568 | 12/1999 |
| GB | 2341943 | 3/2000 |

(Continued)

OTHER PUBLICATIONS

Yan et al., Use of Lasers in Laryngeal Surgery, J Voice. Jan. 2010; 24(1): 102-109.*

(Continued)

*Primary Examiner* — Gary Jackson
*Assistant Examiner* — Scott T Luan
(74) *Attorney, Agent, or Firm* — Meunier Carlin & Curfman LLC

(57) ABSTRACT

Provided herein are devices, systems and methods for treating a vocal fold pathology by forming a substantially planar void below the epithelium of the vocal fold using optical energy. Also provided are devices, systems, and methods for combined imaging and treating of a vocal fold pathology.

13 Claims, 24 Drawing Sheets

(56) References Cited

U.S. PATENT DOCUMENTS

| | | | |
|---|---|---|---|
| 5,720,894 A * | 2/1998 | Neev et al. | 216/65 |
| 5,785,704 A | 7/1998 | Bille et al. | |
| 5,893,830 A | 4/1999 | Zeitels | |
| 5,995,867 A | 11/1999 | Zavislan et al. | |
| 6,451,009 B1 | 9/2002 | Dasilva et al. | |
| 6,620,180 B1 | 9/2003 | Bayes et al. | |
| 6,778,902 B2 | 8/2004 | Hathiram et al. | |
| 6,839,586 B2 | 1/2005 | Webb | |
| 6,975,898 B2 | 12/2005 | Seibel | |
| 7,050,906 B2 | 5/2006 | Hathiram et al. | |
| 7,131,968 B2 | 11/2006 | Bendett et al. | |
| 7,167,622 B2 | 1/2007 | Temelkuran et al. | |
| 7,172,588 B2 | 2/2007 | Stingl et al. | |
| 7,218,446 B2 | 5/2007 | Dixon et al. | |
| 2003/0158544 A1 * | 8/2003 | Slatkine | 606/10 |
| 2005/0107852 A1 | 5/2005 | Levernier et al. | |
| 2005/0154380 A1 | 7/2005 | DeBenedictis et al. | |
| 2006/0142746 A1 | 6/2006 | Friedman et al. | |
| 2006/0195076 A1 | 8/2006 | Blumenkranz et al. | |
| 2007/0154461 A1 * | 7/2007 | Kleinsek | 424/93.7 |
| 2007/0213618 A1 | 9/2007 | Li et al. | |
| 2008/0058780 A1 | 3/2008 | Vogler | |
| 2009/0034927 A1 * | 2/2009 | Temelkuran et al. | 385/125 |
| 2009/0099595 A1 | 4/2009 | Cheng et al. | |

FOREIGN PATENT DOCUMENTS

| | | | |
|---|---|---|---|
| WO | 2009094451 A2 | | 7/2009 |
| WO | WO2010091234 | * | 2/2010 |
| WO | 2011091283 A1 | | 7/2011 |

OTHER PUBLICATIONS

International Search Report, dated Mar. 28, 2011, in corresponding International Application No. PCT/US2011/022099.

International Preliminary Report on Patentability and Written Opinion, dated Jul. 24, 2012, in corresponding International Application No. PCT/US2011/022099.

International Search Report, dated Aug. 21, 2009, in related International Application No. PCT/US2009/031694.

Copending U.S. Appl. No. 12/811,888, filed Jul. 7, 2010.

Bird, Damian, et al., "Two-photon fluorescence endoscopy with a micro-optic scanning head," Opt. Let, vol. 28, No. 17, Sep. 1, 2003, pp. 1552-1554.

Flusberg, BA, et al., "Fiber-optic fluorescence imaging," Nat Methods, vol. 2, No. 12, Dec. 2005, pp. 941-950.

Flusberg, BA, et al., "In vivo brain imaging using a portable 3.9 gram two-photon fluorescence nnicroendoscope," Opt Lett., vol. 30, No. 17, Sep. 1, 2005, pp. 2272-2274.

Girard, B. et al., "Microtomographic Analysis of Healing of Femtosecond Laser Bone Calvarial Wounds Compared to Mechanical Instruments in Mice With and Without Application of BMP-7," Lasers in Surgery and Medicine, vol. 39, 2007, pp. 458-467.

Göbel, W., et al., "Miniaturized two-photon microscope based on a flexible coherent fiber bundle and a gradient-index lens objective," Opt. Lett., vol. 29, No. 21, Sep. 1, 2005, pp. 2521-2523.

Goetz, MH, et al., "Computer-guided laser probe for ablation of brain tumours with ultrashort laser pulses," Phys. Med. Biol., Issue 44, 1999, pp. N119-N127.

Helmchen, F., et al., "A miniature Head-Mounted Two-Photon Microscope: High-Resolution Brain Imaging in Freely Moving Animals," Neuron, vol. 31, No. 6, Sep. 27, 2001, pp. 903-912.

Horn, M., et al., "The use of confocal laser-scanning microscopy in microsurgery for invasive squamous cell carcinoma," J. Derm., vol. 156, 2007, pp. 81-84.

Hoy, Christopher, et al., "A Compact Scanning Head for Simultaneous Two-Photon Imaging and fs-Laser Microsurgery," Presentation: SPIE Photonics West 2007, The Ben-Yakar Group, The University of Texas at Austin, Jan. 22, 2007, 11 pages.

Hoy, Christopher, et al., "A Miniature Microscope for Two-Photon Imaging and Femtosecond Laser Surgery," Conference Paper, Frontiers in Optics (FiO), San Jose, California, Sep. 16, 2007, 1 page.

Hoy, Christopher, et al., "Miniaturized probe for femtosecond laser microsurgery and two-photon imaging," Optics Express 9996, vol. 16, No. 13, Jun. 23, 2008, 10 pages.

Kim, D., et al., "High-speed handheld multiphoton multifoci microscopy," Multiphoton microscopy in the biomedical sciences IV, at Biomedical Optics 2001, San Jose, California, SPIE Proc., 5323, 2004, pp. 267-272.

Lee, D., et al., "Two-axis gimbaled microscanner in double SOI layers actuated by self-aligned vertical electrostatic combdrive," in proceedings of Solid-State Sensors, Actuators and Microsystems Workshop, Hilton Head Island, 2004, pp. 352-355.

Leppert, J., et al., "Multiphoton Excitation of Autofluorescence for Microscopy of Glioma Tissue," Neurosurgery, vol. 58, No. 4, 2006, pp. 759-767.

Loesel, FH, et al., "Non-thermal ablation of neural tissue with femtosecond laser pulses," Appl. Phys., B-66, 1998, pp. 121-128.

Skala, M.C., et al., "Multiphoton Microscopy of Endogenous Fluorescence Differentiates Normal, Precancerous, and Cancerous Squamous Epithelial Tissues," Cancer Research 65, 2005, pp. 180-186.

Thomas, T.P., et al., "Detection and Analysis of Tumor Fluorescence Using a Two-Photon Optical Fiber Probe," Biophys. J., vol. 86, Jun. 2004, pp. 3959-3965.

Vogel, A., et al., "Mechanisms of femtosecond laser nanosurgery of cells and tissues," Applied Physics B: Lasers and Optics, vol. 81, No. 8, 2005, pp. 1015-1047.

Wahrburg, J., et al., "Concept of a Novel Laser Probe for Minimal Invasive Applications in Neurosurgery," Mechatronics in Surgery, vol. 6, issue 4, 1996, pp. 479-489.

Wilder-Smith, et al., "In Vivo Multiphoton Fluorescence Imaging: A Novel Approach to Oral Malignancy," Lasers in Surgery and Med., vol. 35, 2004, pp. 96-103.

Wisweh, Henning, et al., "Optical coherence tomography monitoring of vocal fold femtosecond laser microsurgery," Proceedings of the European Conferences on Biomedical Optics, 2007, 7 pages. Retrieved from http://www.dmphotonics.com/Optical-Coherence_Tomography/Optical%20coherence%20tomography%20monitoring.pdf.

Yanik, et al., "Functional regeneration after laser axotomy," Nature, vol. 432, 2004, p. 822.

* cited by examiner

SYSTEMS, DEVICES AND METHODS FOR IMAGING AND SURGERY

CROSS-REFERENCE TO RELATED APPLICATIONS

This application claims the benefit of U.S. Provisional Patent Application No. 61/297,532, filed Jan. 22, 2010, which is incorporated herein by reference in its entirety.

BACKGROUND

Vocal fold scarring, resulting from disease or post-surgical healing, reduces the mechanical compliance of the vocal tissue and is a major cause of voice disorders. There are a current lack of reliable methods and systems for treating vocal fold scarring.

SUMMARY

Provided herein are methods of treating a vocal fold pathology. The methods comprise applying optical energy to a vocal fold within a subject, where the optical energy creates a sub-epithelial void in the vocal fold, and optionally directing a substance into the void, where the substance is substantially confined within the void to treat the vocal fold pathology. Optionally, the method further comprises applying a further optical energy to the vocal fold within the subject, wherein the further optical energy is configured for imaging the vocal fold or portion thereof; receiving light from the irradiated tissue; and producing an image of the vocal fold or a portion thereof from the received light.

A smallest dimension of the void formed, as measured in a direction substantially parallel to the overlying tissue surface of the vocal fold, is preferably at least about 1 millimeter. The vocal fold may comprise scar tissue, and the void can be created below the vocal fold epithelium and above the scar tissue.

Also provided are systems for surgical manipulation of biological tissue. Exemplary systems comprise a pulsed optical energy source configured to produce optical energy for surgical manipulation of biological tissue; an optical arrangement configured for transmission of the optical energy produced by the optical energy source onto the biological tissue for surgical manipulation; and a scanning device configured to direct the optical energy transmitted onto the biological tissue across the tissue surface over an area of tissue surface preferably having dimensions greater than about 1 millimeter by 1 millimeter to form a void beneath the tissue surface. The optical energy source may comprise an ultra-fast pulsed laser configured to ablate or remove biological tissue; and the pulse repetition rate of the pulsed laser may be at least about 250 kilohertz (kHz). Optionally, the system further comprises a biomaterial substance configured to be placed in the void thus formed.

BRIEF DESCRIPTION OF DRAWINGS

FIG. 13b(a) is an image of a human vocal fold. FIG. 13b(b) is a schematic diagram of vocal fold histology (coronal section) corresponding to the A-A' reference line in FIG. 13b(a) showing the site for typical scar formation. FIGS. 13b(c) and 13b(d) are schematic diagrams illustrating an exemplary surgery probe positioned against the compliant vocal tissue, deforming it around the optical window of the probe to facilitate both imaging of the SLP/scar and ablation of a substantially planar void within the scar. FIG. 13b(e) is a schematic diagram illustrating the use of a specialized phonosurgery Zeitels needle to inject a substance into the new surgical plane and fill the void selectively. FIG. 13b(f) is a schematic diagram illustrating a treated vocal fold void filled with a compliant biomaterial substance.

FIG. 17b is a cross-sectional diagram of the miniaturized phonomicrosurgery probe shown in FIG. 17a.

DETAILED DESCRIPTION

Figure 1:
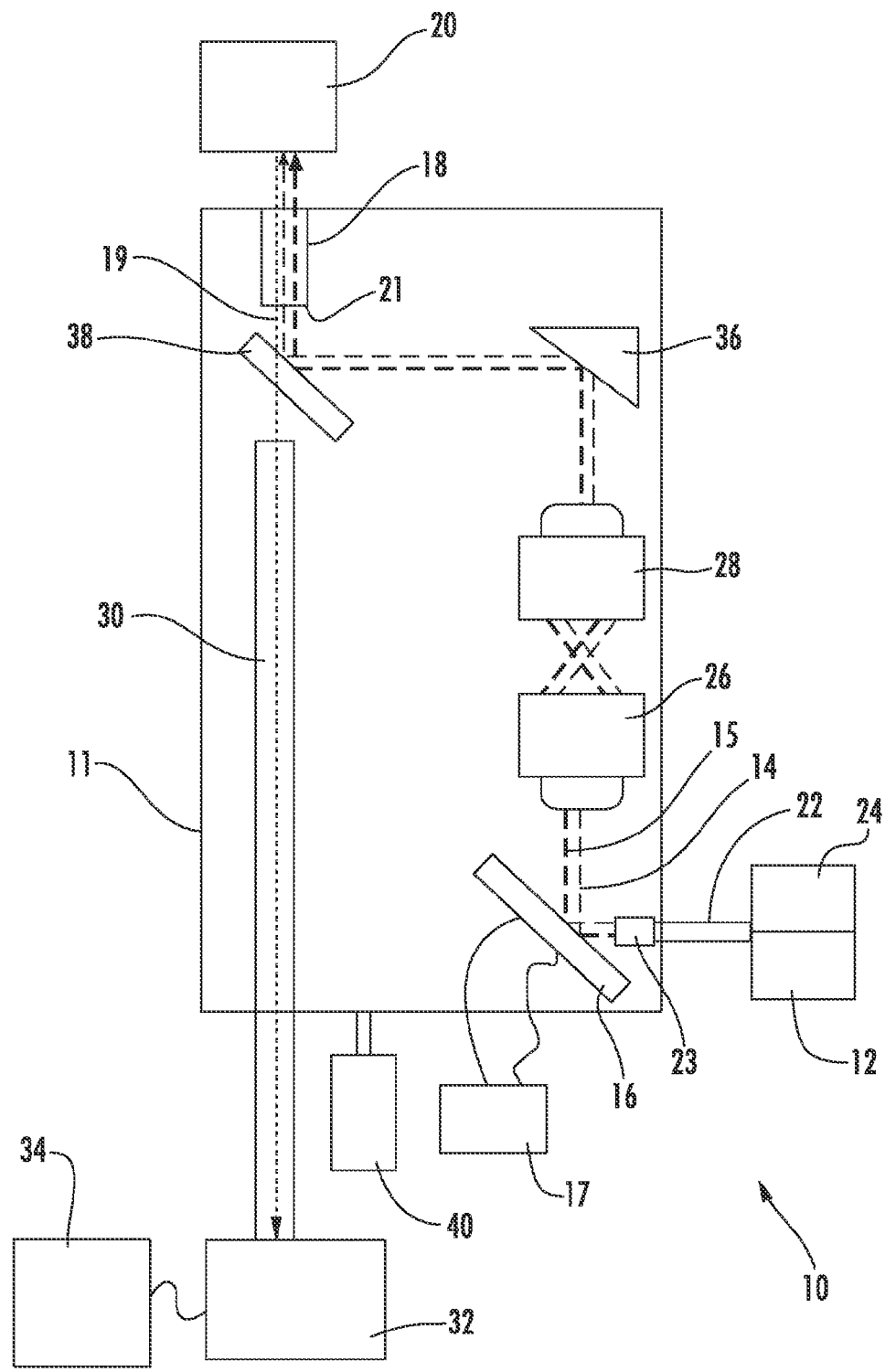
FIG. 1 is a schematic diagram illustrating an exemplary multiphoton imaging and surgical system.

Human vocal folds are paired structures approximately 12-18 millimeters (mm) long and 4 mm thick that vibrate during voicing, effectively valving the air flow from the lungs and producing sound, a process referred to as phonation. Each vocal fold is a layered structure that comprises a pliable connective tissue layer known as the lamina propria (LP) that is sandwiched between a thin epithelium and the vocalis muscle. The LP is further subdivided into the superficial lamina propria (SLP), an intermediate layer, and a deep layer. The SLP is relatively soft and amorphous in structure as compared to the deeper layers, which contain more fibrous proteins. The SLP is critical for normal phonation, since most of the deformation of the mucosa that takes place with each cycle of oscillation occurs in this layer.

The vocal folds of the human larynx may become scarred in response to various traumas or other effects. This scarring can prevent or inhibit proper vibration of the vocal folds and may lead to a loss of voice function. In the vocal folds, the superficial lamina propria located below the epithelium is driven into vibration by the flow of exhaled air. However, this layer is often replaced by dense scar tissue originating from damage to the vocal fold surface.

To re-establish the pliability of this superficial layer, a soft biomaterial can be placed beneath the epithelium. Injecting a biomaterial directly into dense scar tissue generally does not produce the desired results due to the high injection pressures needed, the probability of rupturing the mucosa, and/or the tracking of material to undesired locations within the tissue along paths of least resistance. The lack of proper localization of these injectables is a significant hindrance to their clinical success.

Provided herein are devices, systems and methods for imaging and/or surgical manipulation of biological tissue, such as a vocal fold. The biological tissue can be located in, or can be derived from, a human or non-human animal. Biological tissue can comprise any tissue, or portion thereof, that makes up or is derived from, an organism, such as a mammal. Biological tissue can comprise a cell, a collection of cells, or portions of a cell or cells. Biological tissue also includes organized tissues such as, for example, organs or portions thereof. Biological tissue may be normal or diseased. For example, biological tissue can comprise a cancerous or precancerous cell or collections of cancerous or precancerous cells.

By way of example, the biological tissue can comprise a vocal fold in a larynx. The vocal fold may be scarred. Thus, the surgical manipulation of biological tissue can comprise the surgical manipulation of a vocal fold to treat a vocal fold pathology.

Thus, provided are methods for treating a vocal fold pathology in a subject. The methods comprise creating a void in a vocal fold within a subject by applying optical energy to a vocal fold within a subject. The optical energy can be configured to create a sub-epithelial void in the vocal fold, preferably without piercing or damaging the overlying epithelium, e.g., by ablating a portion of the sub-epithelial tissue.

The sub-epithelial void can, for example, have a length and a width dimension that are each greater than about 1 millimeter (mm), as measured in directions substantially parallel to the surface of the overlying epithelium. Optionally, the length and width dimensions may each be greater than about 2 mm. The void can be formed at a depth of about 100 to 200 microns beneath the epithelial layer of the vocal fold. The void can, for example, be created above or within scar tissue that may be present in the vocal fold. Optionally, the optical energy can be used to excise tissue. For example, the optical energy can be focused up to about 1 mm beneath the surface of the tissue, and a scanning procedure can be used to cut a plane in the tissue. The superficial layer of the tissue can be peeled back to allow access to the deeper tissue. This process can be repeated to remove further layers of tissue beyond 1 mm in depth.

In the exemplary methods and systems described herein, the optical energy can be scanned over a particular area of tissue surface, e.g., to form a sub-epithelial void or pocket thereunder. The scanned area (and corresponding void that may be formed using the scanned optical energy) can have a shape that is substantially rectangular or ovoid, which may be characterized by a width and a length as measured in directions that lie along the tissue surface. The scanned area may have length and width dimensions of at least about 1 mm by about 1 mm. In certain embodiments, the scanned area of the tissue surface may be at least about 2 mm by 2 mm. Optionally, the scanned area of the tissue surface may be as large as about 4 mm by about 14 mm. A width of the scanned area of the tissue surface can be, for example, about 1 mm, about 2 mm, about 3 mm, or about 4 mm. In certain embodiments, the width of the scanned area may be larger than about 4 mm. A length of the scanned area of the tissue surface can be, for example, about 1 mm, about 2 mm, about 3 mm, about 4 mm, about 6 mm, about 8 mm, about 10 mm, about 12 mm, or about 14 mm. In certain embodiments, the length of the scanned area may be greater than about 14 mm.

Optionally, a substance may then be directed into the void formed in the vocal fold. The substance can be substantially confined within the void to treat the vocal fold pathology in the subject. Confined, as used herein, means localized to the site of the void (i.e., the majority, if not all, of the substance stays within the created void) to effect the treatment rather than to diffuse into surrounding tissue.

The substance can, for example, be directed into the void by injecting the substance into the void with a needle. Such injection can be performed using, e.g., a Zeitels vocal fold infusion needle. This needle is designed to enhance the precision of delicate dissection work within the stratified microstructure of the vocal fold.

Optionally, the substance may contain fluorescently labeled nanospheres and/or a fluorescent macromolecular dye so that the optional imaging capabilities of the systems described herein can be utilized to assess the condition and location of the injected substance. The fluorescently-labeled nanospheres can, for example, be obtained from Bang Labs, Inc. (Fishers, Ind.). Optionally, the fluorescently-labeled nanospheres may be about 100 nanometers in diameter. The fluorescent macromolecular dye can, for example, comprise high-molecular weight dextran. The concentration of the nanoparticles or dye can be low enough to not significantly affect the viscosity of the substance, which may be verified by performing basic rheometry.

Characteristics of the substance can be selected to re-establish the pliability of the superficial lamina propria (SLP) in the vocal fold when the substance is introduced into the void formed as described herein. Re-establishing the pliability of the SLP can restore the voicing capabilities of the subject. To re-establish the pliability of the SLP, the substance can be, for example, a biomaterial. Optionally, the biomaterial can comprise collagen, a polymeric gel, fat, or hyaluronic acid. The biomaterial can, for example, include growth factors (e.g., platelet derived growth factor (PDGF), bone morphogenetic protein (BMP), and/or hepatocyte growth factor (HGF)) and/or stem cells. By forming a void in the vocal fold, the substance can be substantially confined to the volume within the void to effect the treatment. The confined substance can, for example, partially or fully restore the function of the vocal fold and improve the vocalization of the subject.

Optionally, any of the exemplary methods for treating a vocal fold pathology described herein can further include directing further optical energy to the vocal fold within the subject, where properties of the further optical energy may be selected to facilitate imaging of the vocal fold or a portion thereof; receiving light from the vocal fold or portion thereof based on the further optical energy; and producing an image of the vocal fold or a portion thereof based on the received light. The further optical energy can optionally be the same as the optical energy used to treat the tissue, or it can be produced by a different energy source and/or have different optical properties.

FIG. 1 is a schematic diagram illustrating an exemplary system 10 for surgical manipulation of biological tissue and/or for multi-photon imaging. The system 10 can be used to treat a vocal fold pathology, including performing laryngeal microsurgery, and/or to image a vocal fold or a portion thereof.

The system 10 includes an ultrafast pulsed laser optical energy source 12. The terms ultrafast and ultrashort are used interchangeably herein. The optical energy source 12 is configured to produce optical energy for surgical manipulation of biological tissue in the subject. For example, the optical energy source 12 can be configured to produce one or more pulses of optical energy having a duration on the order of a nanosecond (ns) or less. Optionally, the optical energy source 12 is a picosecond (ps) or a femtosecond (fs) optical energy source comprising a laser that can generate one or more laser pulses having durations on the order of picoseconds or femtoseconds, respectively. The optical energy source 12 can also be configured to produce laser pulses that are in the near-infrared regime of the optical spectrum.

Femtosecond lasers can be used as an ultrashort laser pulse source for multiphoton imaging and femtosecond laser microsurgery techniques described herein. Femtosecond lasers can include lasers configured to emit laser pulses having pulse durations between about 1 ps and about 1 fs. The femtosecond laser can be a solid state laser that utilizes a broadband gain medium, such as titanium-doped sapphire or chromium-doped forsterite crystals. In such lasers, femtosecond laser pulses can be created when mode-locking is achieved, either passively or actively, and the constructive interference between intracavity modes can provide a powerful ultrashort pulse of optical energy. A picosecond laser can be configured to produce pulses of optical energy having durations between about 1 ns and about 1 ps.

Femtosecond laser pulses of higher intensity can be created using an optical amplifier, for example, a chirped-pulse amplifier or an optical parametric amplifier. In both oscillator and amplifier systems, femtosecond laser pulses are typically in the near-infrared wavelength range, e.g., between about 600 nm and about 1000 nm, where biological tissue is substantially transparent to such energy (e.g., such energy is weakly absorbed by the tissue).

As used herein, surgical manipulation can include photodamage of biological tissue located in a subject. Thus, in vivo or ex vivo biological tissue may be targeted for surgical manipulation using the exemplary systems described herein.

The photodamage can be localized within a focal volume where optical energy from the optical energy source 12 is focused. The focal volume can be located in a target tissue, such as a vocal fold. Application of optical energy from the optical energy source 12 using the described systems can produce ablation of tissue in the subject. Such ablation can also be confined to the focal volume located in the tissue.

The ultra-fast surgical optical energy source 12 can be provided in communication with an optical delivery fiber 22 or other waveguide. The optical delivery fiber 22 is configured to transmit optical energy 14 from the optical energy source 12 into a housing 11. An objective lens 18 can also be provided in conjunction with the housing 11. The objective lens 18 is configured to receive optical energy generated by the optical energy source 12 that is directed into the housing 11 by the optical delivery fiber 22. The objective lens 18 can optionally be a gradient index (GRIN) lens, an aspheric lens, a spherical lens, a chromatic doublet, and the like. Z-scanning techniques can also be used, which include scanning of focused optical energy to varying depths within the target tissue. This can be accomplished, for example, by moving the system 10 or portions thereof towards or away from the target tissue. For example, the objective lens 18 can be actuated to move towards or away from the target tissue using a microelectromechanical (MEMS) actuator or a piezoelectric (PZT) actuator. Similarly the entire housing 11, including the objective lens 18, can be actuated to move towards or away from the target tissue using a MEMS actuator or a PZT actuator.

Optionally, the optical delivery fiber 22 may be an air-core photonic crystal fiber (PCF). Light transmitted along the fiber 22 can be directed through a collimating lens 23 and onto a scanning device 16. In other examples, instead of a scanning device 16, the optical delivery fiber 22 can be moved to provide scanning of optical energy from the optical energy source 12. For example, the fiber 22 can be moved using a piezoelectric scanning device to scan optical energy from the optical energy source 12 over portions of the tissue being treated.

The scanning device 16 can optionally be a MEMS scanner. Exemplary scanning devices 16 may include an electro-optic crystal, a rotating wedge prism, and/or piezoelectric elements. If a MEMS scanner is used, it can be provided as a two-axis gimbaled scanner with a reflective surface. The reflective surface can include a reflective coating, e.g., a metal coating. For example, the metal coating can comprise silver or aluminum. The scanning device 16 can be actuated to scan optical energy from the optical delivery fiber 22 to the objective lens 18. For example, at least one processing unit 17 can be in communication with the scanning device 16. The processing unit 17 can be configured to control the actuated movement of the scanning device 16 for direction of optical energy from the optical delivery fiber 22 to the objective lens 18. The scanning device 16 may also be located in the housing 11, and the housing can be sized for endoscopic in vivo surgical procedures in the subject. Portions of the system 10 can be referred to as a probe, for example, when the housing 11 and/or other portions of the system are configured for surgical manipulation and/or imaging in a human or non-human subject. The probe can be configured, e.g., for insertion into the throat of a subject for surgical and/or imaging applications on a vocal fold.

Optical energy 14 from the ultra-fast pulsed surgical optical energy source 12 that is directed onto the scanning device 16 can be further directed through a pair of relay lenses 26 and 28 prior to contacting the back aperture 21 of the objective lens 18. Each relay lens of the pair 26 and 28 can be an aspherical lens. Optionally, the numerical aperture of each relay lens is about 0.9 or less. The optical energy 14 from the optical energy source 12 may optionally contact a mirror 36 after passing through the relay lens 28. The optical energy 14 from the optical energy source 12 can also be directed to the objective lens 18 using a hot mirror 38. A portion of the optical energy 14 from the optical energy source 12 that contacts the back aperture 21 of the objective lens 18 may be transmitted onto a region of interest, e.g., target tissue 20 of the subject.

The objective lens 18 can focus optical energy 14 from the optical energy source 12 into a focal volume where surgical manipulation can occur by the focused optical energy 14. The objective lens 18 can have a numerical aperture of about 0.4 or higher. As described above, properties of the optical energy 14 can be selected to produce photodamage or ablation of tissue in the subject. An actuator device 40, such as an electric motor, can be provided to move the housing 11 towards or away from the target tissue 20. In certain embodiments, the system 10, or portions thereof such as the housing 11, can be moved in a ferrule using a piezoelectric device or micromotor.

The system 10 can further include a light source 24 for multi-photon imaging. The imaging light source 24 can be a pulsed optical energy source used for multi-photon imaging. Although the light source for surgery 12 and the light source for imaging 24 are separately depicted in this example, in certain embodiments the same light source can be used to provide optical energy for both surgery and imaging. For example, a single light source may be configured to produce both optical energy 14 and imaging light 15. Optionally, optical energy having the same characteristics can be used for both imaging and surgery. Thus, a system that includes an ultra-fast pulsed surgical optical energy source and an imaging light source can be provided with one optical energy source configured to produce light configured for imaging and light configured for surgery. The light used for imaging and for surgery may optionally have the same or similar characteristics such as, for example, wavelength and pulse duration.

The imaging light source 24 can therefore be configured to produce light for imaging of biological tissue, referred to herein as imaging light 15. Similar to the optical energy 14, the imaging light 15 can be transmitted along the optical delivery fiber 22, through the collimating lens 23 and onto a scanning device 16. The imaging light 15 can be further directed through the pair of relay lenses 26 and 28 and through the objective lens 18. Before being transmitted through the objective lens 18, the imaging light 15 may contact the mirror 36 and the mirror 38, which can be configured to guide the imaging light 15 on to the back aperture 21 of the objective lens 18. The objective lens 18 is configured to transmit imaging light 15 to a region of interest such as the target tissue 20.

The objective lens 18 can be further configured to receive light 19 from the target tissue 20. Light received 19 from the target tissue 20 can include light resulting from excitation of fluorophores in the target tissue. The excitation of the fluorophores can be caused by interaction of the imaging light 15 with portions of the target tissue. Light received from the target tissue can also result from luminescence of nanoparticles located in the target tissue 20. For example, gold luminescence from nanoparticles may be received and/or detected. Further, the light received from the target tissue may result from generation of a second harmonic of light incident on a portion of the target tissue. The second harmonic can be produced from the interaction of the target tissue and the imaging light 15.

Thus, multiphoton imaging can refer to methods for imaging or visualization that utilize fluorescent and/or luminescent emission light arising from a multiphoton process event. For multiphoton imaging using the described system, a train of ultrashort laser pulses can optionally be focused into the sample or target tissue 20 to be imaged. Within the focal volume, the light intensities can be sufficiently high to induce nonlinear processes involving the simultaneous absorption of multiple photons. Examples of such processes are two- and three-photon absorption, second harmonic generation, and two-photon luminescence. The light emitted from the multiphoton process can be collected and detected by the photodetector 32, such that an electrical signal is generated that is proportional to the amount of emitted photons collected. By scanning the focused laser beam and collecting emitted light at successive positions in the target tissue, an image can be reconstructed by mapping the detected light signals to corresponding locations in an image.

In addition to imaging based on the intensity of the collected emission light (e.g., the received light 19), additional information about the sample can be gained by further analysis of the received light. In one exemplary method, the received light can be directed to a spectrometer, and spectral information can be assigned to each location in the reconstructed image. In another exemplary method, the received light can be directed to a single-photon counting detector and may be used to assign fluorescent lifetime information to various locations in the reconstructed image.

A portion of the light received by the objective lens 18 from the target tissue can be transmitted to an optical transmitter 30. In the system 10, the hot mirror 38 facilitates passage of light from the objective lens 18 into communication with the optical transmitter 30. The optical transmitter 30 can transmit light received from the target tissue to the photodetector 32. The photodetector 32 is configured to detect at least a portion of the light transmitted along the optical transmitter 30. The photodetector can be in communication with at least one processing device 34 that can be configured to produce an image from light detected by the photodetector 32.

Portions of the system 10 may be located in the housing 11. Some portions of the system 10 may also be located outside of the housing 11. As described above, the housing 11 can optionally be moved towards or away from the target tissue 20 using an actuating device. The system 10 can be used for surgical manipulation of biological tissue and/or for multiphoton imaging using optical energy from the optical energy source 12. For example, the exemplary system 10 can be used for imaging and/or treatment of a vocal fold using optical energy.

Whether the system 10 is used for surgical manipulation of biological tissue alone, multi-photon imaging alone, or both surgical manipulation of biological tissue and multi-photon imaging can be determined by an operator of the system. For example, if only surgical manipulation of biological tissue is desired, the system 10 can be used to direct optical energy 14 to the target tissue. If only multi-photon imaging is desired, the system 10 can be used to direct imaging light 15 to the target tissue. If both multi-photon imaging and surgical manipulation of biological tissue is desired, the system can be used to direct both imaging light 15 and optical energy 14 to the target tissue.

In certain embodiments, at least a portion of the system 10 (or any other exemplary system described herein) may be provided in a miniaturized probe configured to perform multiphoton microscopy and/or ultrashort pulse laser surgery. For example, such probe can be sized to facilitate placement into a subject for imaging and/or surgery of a vocal fold.

The system 10 can be used to enhance a field of view (FOV), resolution, and/or collection efficiency while avoiding undesirable effects that may be present in conventional miniaturized multiphoton fluorescent microscope designs. This can be achieved by providing a miniature optical system between the scanning device 16 and the imaging objective lens 18. The exemplary system 10 may be used for targeted delivery of higher-energy ultrashort pulses for combined ultrashort-pulse laser micro-/nanosurgery and multiphoton imaging. Thus, the exemplary system 10 can be used for combined medical diagnosis and treatment of diseased tissues and for investigation of various biological tissues. In one aspect, the system 10 can configured for real-time diagnosis and removal of small cancerous lesions in skin, in body cavities, or intraoperatively.

The imaging system 10 can be configured to couple the scanning device 16 to the objective lens 18, such that the optical energy 14 and/or imaging light 15 do not traverse the plane of back aperture 21 of the objective lens 18 during scanning. This can facilitate use of the whole scanning angle of the scanning device 16 while avoiding limitations based on the distance to the objective lens 18 or the size of the objective lens 18. Accordingly, the FOV can be enlarged without degrading resolution.

The system 10 may also provide expansion of the optical energy 14 and or the imaging light 15, wherein a diameter or size of either light beam may be relatively small at the scanner 16 so as to reduce diffraction, and can be larger at the objective 18 to increase resolution.

By imaging the scanner 16 to the objective lens 18, the scanning device 16 can be moved away from the objective lens 18, which allows collection optics, such as the optical transmitter 30, to be placed close to the objective 18 to enhance collection efficiency. By utilizing higher-energy ultrashort pulses, ultrashort-pulse laser micro-/nanosurgery can be achieved that provides precision ablation of specifically targeted nanoscale structures, such as organelles or axons with less collateral damage when compared to conventional continuous wave and long pulse (e.g., pulses greater than about 1 ns) lasers. In addition, the system 10 can facilitate scanning of the optical energy 14 for ablation of larger tissue regions.

The scanning device 16 of the exemplary system 10 can be miniaturized, and may optionally be configured to scan a pulse train of near-infrared laser pulses, each with a duration between about 100 and 1/100th of a picosecond, about two axes, using a pair relay lenses (26 and 28), which may optionally be miniaturized positive lenses that can be used to image the location of the scanning device to the back aperture of an objective lens 18. The objective lens 18 can optionally focus optical energy into the sample (e.g., onto a portion of the target tissue 20).

For microscopy, optical energy can excite intrinsic fluorophores (autofluorescence), exogenous fluorophores, and/or metallic nanoparticles. The light emitted from these processes (fluorescence or luminescence) can be collected through the objective lens 18. In addition to use of metallic nanoparticles for imaging of luminescence, the same nanoparticles may be used during surgical applications of the disclosed apparatus by using the ultrashort pulse laser source to excite the plasmon resonance of the nanoparticles and ablating at the particles through the near-field enhancement effect.

Light received by the objective lens 18 (collected light from the sample 20) can pass through a dichroic mirror or hot mirror 38 and be collected by a optical transmitter 30, such as an optical fiber. The system 10 can be used in conjunction with higher-energy ultrashort laser pulses for microsurgery of biological tissues. Optionally, the foci inside the system may be located in air and the light propagation through glass or plastic can be reduced by optionally eliminating long-relay gradient index (GRIN) lenses such as those that may be used in conventional multiphoton endoscope designs. For micro/nanosurgery procedures, the optical energy 14 focused into the target tissue 20 can be of sufficient intensity to cause intentional photodamage within the tissue, either through ablation or indirect bond breaking due to free electron formation.

As described above, the scanning device 16 can optionally be a MEMS scanner. The scanning device 16 can optionally include a MEMS mirror having a diameter larger than the diameter of the light beam projected onto it. The relay lens pair 26 and 28 can optionally include molded aspherical lenses, wherein the numerical apertures of each lens may be less than about 0.9. The relay lenses 26, 28 can also be configured to expand the light beam, where the beam size of the imaging light 15 and/or optical energy 14 can be relatively small at the scanning device 16 so as to reduce diffraction, and can be larger at the objective lens 18 to increase resolution.

The system 10 can optionally provide both ultrashort-pulse laser micro-/nanosurgery and multiphoton microscopy in a single miniaturized device. Ultrashort-pulse laser micro-/nanosurgery provides a high-precision tool for making subcellular incisions, ablating nanoscale structures, modifying organelles and axons, and the like. The exemplary system 10 can provide both imaging and high-surgical precision to facilitate microsurgery without the disruption of vasculature. The surgical manipulations of biological tissue such as formation of incisions, can be directed to a specific point of interest, or scanning techniques can be used to modify a large collection of cells. The surgical manipulations of biological tissue can, for example, include manipulations of vocal folds in the larynx. The system 10 can be used to create a subepithelial void in the vocal fold as described herein, or to destroy diseased cells, such as small neoplastic lesions, in real time during a diagnostic imaging process. For example, the system 10 can be used for the targeting of neoplastic lesions and precancerous cells, for which there are currently no accepted imaging modalities for diagnosing small (e.g., less than about 2 mm in size) lesions in the epithelium except those that include a lengthy and invasive biopsy process.

The system 10, or portions thereof, such as the housing 11, can be used as a surface probe device, to access large body cavities (i.e. the mouth), and/or it may be used intraoperatively. Portions of the system 10 can also be manufactured using nanolithography of silicon to provide a "microscope-on-a-chip," which can fit into commercial endoscope housings for colorectal, tracheal, GI, larynx, esophageal, and other applications. The system 10, or portions thereof, such as the housing 11, can be coupled with an aspiration arrangement in an endoscopic probe so that a laser microsurgery technique can be used to excise tissue sections for analysis. For example, optical energy 14, such as that provided by a laser, can be used to cut away a region of interest, which can be aspirated and analyzed in a flow cytometry assay for detection of various pathologies. The system 10, or portions thereof, such as the housing 11, can be provided as a disposable endoscope system. The system 10, or portions thereof, such as the housing 11, may be sized to be positioned inside a body cavity, to be used endoscopically within the accessory channel of commercially-available endoscope devices or as a stand-alone device, or to be used as a handheld device, both externally and intraoperatively in surgically created body cavities and openings.

As described above, metallic nanoparticles for imaging of luminescence can be used, and metallic nanoparticles may also be used during the surgical operation of the system 10 by using an ultrashort pulsed laser source to excite the plasmon resonance of the nanoparticles and producing ablation at the particles based on a near-field enhancement effect.

A focusing lens, such as an objective lens, can be used to focus optical energy 14 and imaging light 15, such as femtosecond laser pulses, into the core of the optical fiber 22. The optical fiber 22 can be a hollow-core fiber, which can be configured to utilize a photonic bandgap to confine light in a defect region making up the core of the fiber. The focusing lens can be selected such that the numerical aperture of the lens is less than that of the optical fiber 22 and the resulting focused laser spot size is smaller than the core size of the optical fiber 22, which can facilitate efficient coupling of the free-space light into the optical fiber 22. If provided, the hollow-core photonic crystal fiber then directs the optical energy by guiding it in a single transverse mode (TEM00) to the housing 11, where the collimating lens 23 collimates the directed optical energy.

Pre-chirping of the optical energy 14 or imaging light 15, provided as a femtosecond laser pulse or the like, can be performed to compensate for dispersion in the optical fiber 22. Additionally, wavelengths can be selected at or near the zero dispersion wavelength of the optical fiber 22 to reduce dispersion. Pre-chirping is a technique that may be used to generate chirping in light pulses to at least partially compensate for chirping caused in a transmitter. For example, two types of chirping that may be used include blue chirping that shifts the wavelength to a longer wavelength side at the rising of an output pulse and to a shorter wavelength side at the falling thereof, and red chirping that shifts the wavelength of a pulse to a shorter wavelength side at the rising of an output pulse and to a longer wavelength side at the falling thereof. The particular chirping technique may be selected based on the fiber or other waveguide used in the transmission channel.

The system 10 may further include a beam splitter such as the hot mirror 38 to separate excitation and emission light. A beam splitter can separate light based on wavelength and can be provided as an element with a dichroic coating that is reflective to a certain wavelength range, such as that of the excitation optical energy, and is transmissive to another wavelength range, such as that of the emitted fluorescent light.

Optionally, the system 10 can be used for femtosecond laser microsurgery, which is a technique for precise manipulation of biological tissues with reduced damage to surrounding tissues. The combination of this technique with two-photon imaging can provide a non-invasive means of visualization to guide such surgery in situ. This method can be used for imaging and microsurgery with a small probe for diagnosing, treating, and monitoring progression of diseased tissue in vivo, in real time, and with cellular precision.

Femtosecond laser microsurgery (FLMS) can provide a high precision for microsurgery performed inside three-dimensional (3D) volumes of tissue. Because of associated high peak intensities and short pulse durations, near infrared (NIR) femtosecond laser pulses may be absorbed through nonlinear processes inside biological materials that are otherwise transparent to NIR wavelengths. The nonlinear absorption processes can occur within the focal volume of the optical energy where the photon flux is sufficiently high. Thus, certain effects such as tissue ablation can be confined to a small volume in the focal plane. The highly localized and efficient absorption of femtosecond laser pulses can use a relatively small amount of energy to achieve tissue ablation. This microsurgery approach thus may facilitate operation with micron-scale precision while reducing collateral damage to surrounding non-target tissues.

The in vivo application of this surgical technique can be guided and monitored by a penetrating 3D imaging technique having similar precision, such as two-photon microscopy (TPM). In TPM, simultaneous absorption of two photons of NIR wavelengths excites fluorophores that usually absorb in the ultraviolet or visible wavelength ranges. Two-photon excitation can facilitate intrinsic optical sectioning and larger penetration depths, e.g., down to about 1 mm. By combining FLMS with TPM, optical energy can be guided with microscopic imaging capabilities deep inside a scattering tissue. The system 10 can therefore be used for treatment and diagnosis of various diseases as well as for in vivo monitoring of disease progression. The system 10, or portions thereof, such as the housing 11, can be positioned in a small and flexible device for FLMS and TPM applications.

Figure 2:
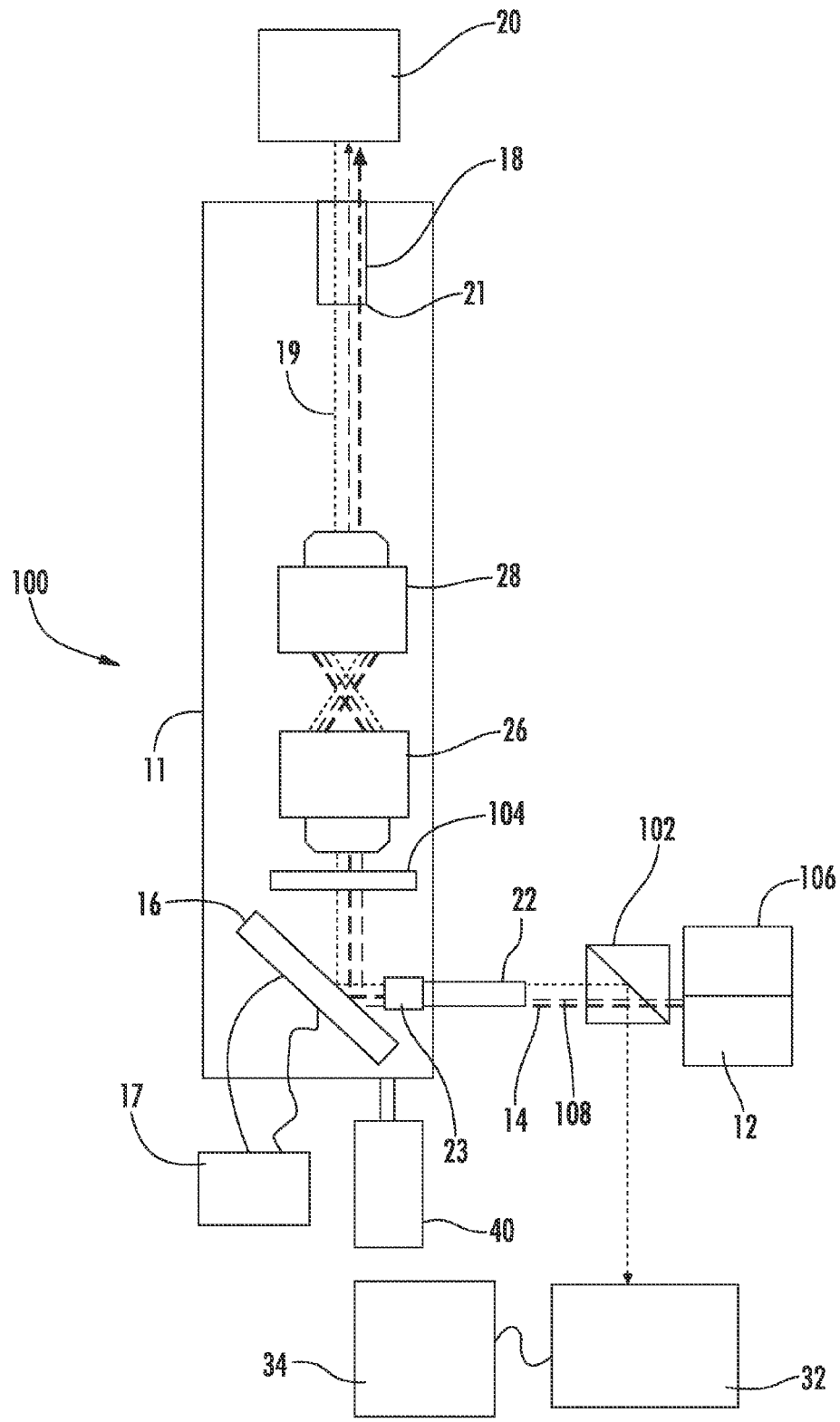
FIG. 2 is a schematic diagram illustrating an exemplary confocal reflectance imaging and surgical system.

FIG. 2 is a schematic diagram of a further exemplary system 100 configured for surgical manipulation of biological tissue in a subject and/or for confocal reflectance imaging in the subject. The system 100 can be used for imaging and/or surgical manipulation of a vocal fold in a subject. The surgical manipulation of biological tissue and/or the confocal reflectance imaging can include, e.g., laryngeal microsurgery or imaging of a vocal fold in a subject to treat or image a vocal fold pathology.

The system 100 includes an ultra-fast pulsed laser optical energy source 12. The optical energy source 12 is configured to produce optical energy for surgical manipulation of biological tissue in the subject. For example, the optical energy source 12 can be configured to produce one or more pulses of optical energy having a duration of about one nanosecond or less. Optionally, the optical energy source 12 may be a picosecond or a femtosecond optical energy source that includes a laser configured to generate one or more laser pulses having a duration on the order of about a picosecond or a femtosecond, respectively. The optical energy source 12 can also be configured to produce laser pulses that are in the near-infrared region of the optical spectrum.

The ultra-fast surgical optical energy source 12 can be provided in communication with an optical delivery fiber 22 or other waveguide. The optical delivery fiber 22 directs light, e.g. optical energy 14, from the optical energy source 12 into a housing 11. A polarizing beam splitter 102 can be provided between the light source 10 and the delivery fiber 22. The polarizing beam splitter 102 can facilitate passage of light from the optical energy source 12 to the delivery fiber 22.

An objective lens 18 may also be provided in conjunction with the housing 11. The objective lens 18 can be configured to receive light generated by the optical energy source 12 that is directed into the housing 11 by the optical delivery fiber 22. Optionally, the optical delivery fiber 22 may be an air-core photonic crystal fiber (PCF). Light transmitted along the fiber 22 can be directed through a collimating lens 23 and onto a scanning device 16. In certain embodiments, the optical delivery fiber 22 can be moved to provide scanning of light from the optical energy source 12 instead of using a scanning device 16. For example, the fiber 22 can be moved using a piezoelectric scanning device that is configured to translate the fiber to scan light from the optical energy source 12 over or along a portion of the tissue of interest.

The scanning device 16 can be a microelectromechanical (MEMS) scanner. If a MEMS scanner is used, it can be provided, e.g., as a two-axis gimbaled scanner with a reflective surface. The reflective surface can include a reflective coating, e.g., a metal coating. For example, the metal coating can comprise silver or aluminum. The scanning device 16 can be actuated to scan light from the optical delivery fiber 22 for transmission to the objective lens 18. For example, at least one processing unit 17 can be provided in communication with the scanning device 16. The processing unit 17 can be configured to control the actuated movement of the scanning device for direction of light from the optical delivery fiber 22 to the objective lens 18. The scanning device 16 may also be located in the housing 11, and the housing can be sized for performing endoscopic in vivo surgical procedures on the subject.

Light from the ultra-fast pulsed surgical optical energy source 12, e.g. optical energy 14, that is directed onto the scanning device 16 can be further directed through a quarter wave plate 104 and through a pair of relay lenses 26 and 28 prior to contacting the back aperture 21 of the objective lens 18. The relay lenses 26, 28 may be aspherical lenses. Optionally, the numerical aperture of each relay lens 26, 28 may be about 0.9 or less. At least a portion of the optical energy 14 from the optical energy source 12 that contacts the back aperture 21 of the objective lens 18 may be directed onto target tissue 20 of the subject. The objective lens 18 can be configured to focus optical energy 14 from the optical energy source 12 into a focal volume, where surgical manipulation can occur by the focused optical energy 14. The objective lens can have a numerical aperture of about 0.4 or higher. As described above, properties of the optical energy can be selected to cause photodamage or ablation of tissue in the subject. An actuator device 40, such as an electric motor, can be used to move the housing 11 towards or away from the target tissue 20 to vary the effective focal depth of the system 100.

The system 100 can further include a light source 106 for confocal reflectance imaging. The imaging light source 106 can be a pulsed or continuous-wave light source such as those used for conventional confocal reflectance imaging. The light source 106 can also produce light that is infrared or near-infrared. For example, the light source 106 can optionally produce pulsed optical energy that is in the infrared or near-infrared region of the optical spectrum. Although the light source for surgery 12 and the light source for imaging 106 are separately depicted in this example, in certain embodiments the same light source can be used for both surgery and imaging. In these embodiments, the light source can be adjustable such that it can produce both light for surgical application and light for imaging application. Thus, the system 100 can include a single source of light or optical energy configured to provide light for both imaging and surgery.

The imaging light source 106 may be configured to produce light for confocal reflectance imaging of biological tissue, referred to herein as imaging light 108. Similar to the optical energy 14, the imaging light 108 can be transmitted along the optical delivery fiber 22, through the collimating lens 23, and onto a scanning device 16. The imaging light 108 can be further directed through the pair of relay lenses 26 and 28 and through the objective lens 18. The objective lens may be configured to transmit imaging light 108 to a region of interest of the target tissue 20.

The objective lens 18 can be further configured to receive light from the target tissue 20. Light received from the target tissue can include light resulting from the back-scattering of light incident on the target tissue. At least a portion of the light received by the objective lens 18 from the target tissue can be transmitted to a photodetector 32. The photodetector 32 can be configured to detect at least a portion of the light transmitted to it. The photodetector can be provided in communication with at least one processing device 34 that is configured to produce an image from light detected by the photodetector 32.

Portions of the system 100 may be located in the housing 11. Some portions of the system 100 can also be located outside of the housing 11. As described above, the housing 11 can be moved towards or away from the target tissue 20 using an actuating device. The system 100 can be configured to provide surgical manipulation of biological tissue using light from the optical energy source 12 and/or confocal reflectance imaging of the tissue.

Whether the system 100 is used for surgical manipulation of biological tissue alone, confocal reflectance imaging alone, or both functions can be determined by an operator of the system. For example, if only surgical manipulation of biological tissue is desired, the system 100 can be used to transmit optical energy 14 to the target tissue. If only confocal reflectance imaging is desired, the system 100 can be used to transmit imaging light 108 to the target tissue. If both confocal reflectance imaging and surgical manipulation of biological tissue is desired, the system can be used to transmit both imaging light 108 and optical energy 14 to the target tissue.

Figure 3:
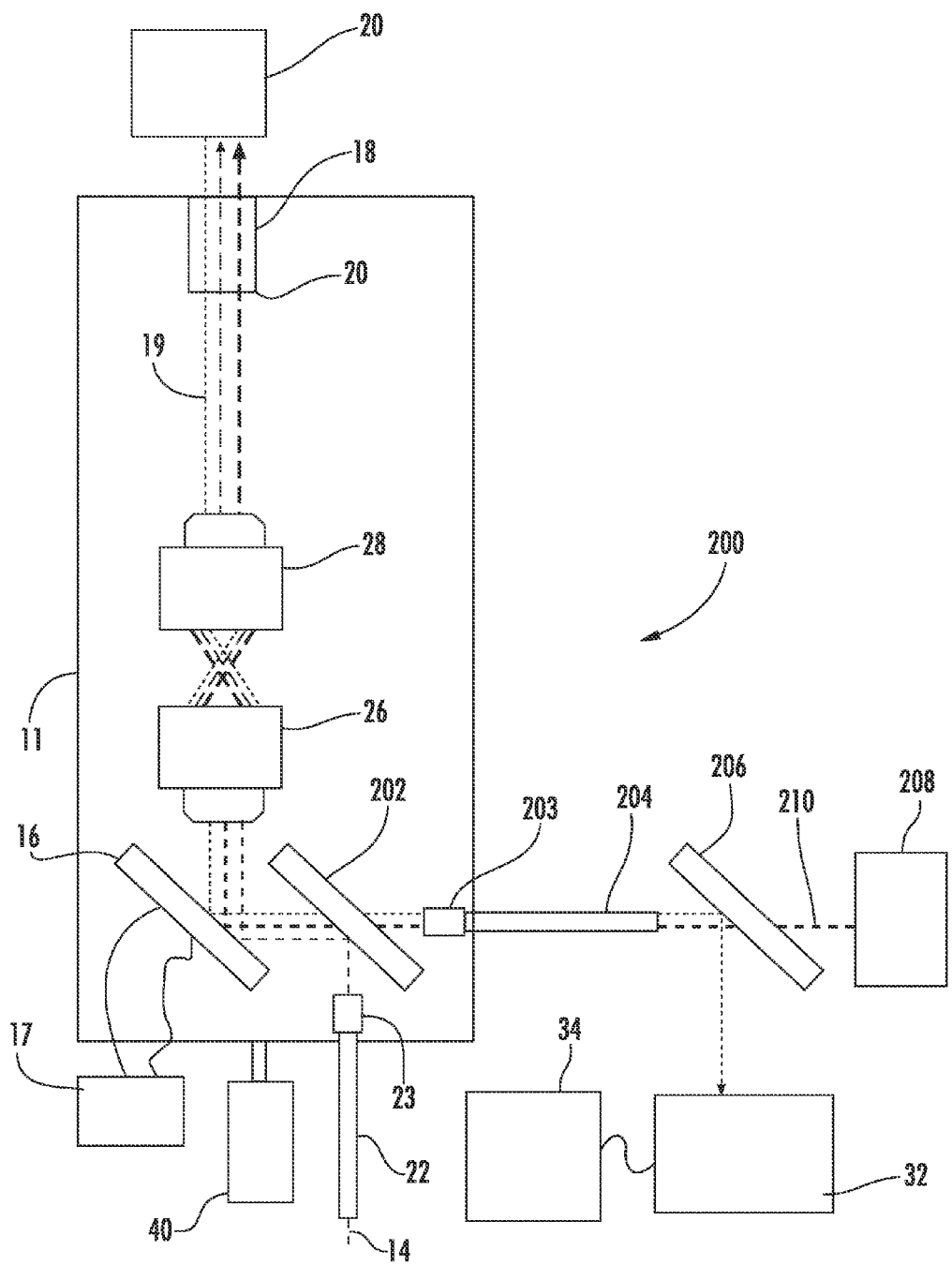
FIG. 3 is a schematic diagram illustrating an exemplary confocal fluorescence imaging and surgical system.

FIG. 3 is a schematic diagram illustrating an exemplary system 200 that may be used for surgical manipulation of biological tissue in a subject and/or for confocal fluorescence imaging in the subject. For example, the system 200 may be used for imaging and/or surgical manipulation of a vocal fold in a subject. Thus, the surgical manipulation of biological tissue and/or the confocal fluorescence imaging can include, for example, laryngeal microsurgery or imaging of a vocal fold in a subject to treat or image a vocal fold pathology.

The system 200 includes an ultra-fast pulsed laser optical energy source 12. The optical energy source 12 is configured to produce optical energy for surgical manipulation of biological tissue in the subject. For example, the optical energy source 12, can be configured to produce one or more pulses of optical energy having a duration of about one nanosecond or less. Optionally, the optical energy source 12 may be a picosecond or a femtosecond optical energy source that includes a laser configured to generate one or more laser pulses having a duration on the order of a picosecond or a femtosecond, respectively. The optical energy source 12 can also be configured to produce laser pulses that are near-infrared.

The ultra-fast surgical optical energy source 12 can be provided in communication with an optical delivery fiber 22 or other waveguide. The optical delivery fiber 22 is configured to direct light, e.g. optical energy 14, from the optical energy source 12 into a housing 11. An objective lens 18 can also be provided in conjunction with the housing 11. The objective lens 18 can be configured to receive light generated by the optical energy source 12 that is transmitted into the housing 11 by the optical delivery fiber 22. Optionally, the optical delivery fiber 22 may be an air-core photonic crystal fiber (PCF). Light transmitted along the fiber 22 can be directed through a collimating lens 23 and onto a mirror 202 for direction onto a scanning device 16. In certain embodiments, the optical delivery fiber 22 can be moved to provide scanning of light from the optical energy source 12 instead of using instead of the scanning device 16. For example, the fiber 22 can be translated using a piezoelectric scanning device that is configured to move the fiber to scan light from the optical energy source 12 along or over a portion of the tissue being treated.

The scanning device 16 can be a microelectromechanical (MEMS) scanner. If a MEMS scanner is used, it can be provided, e.g., as a two-axis gimbaled scanner with a reflective surface. The reflective surface can include a reflective coating, e.g., a metal coating. For example, the metal coating can comprise silver or aluminum. The scanning device 16 can be actuated to scan light from the optical delivery fiber 22 for transmission to the objective lens 18. For example, at least one processing unit 17 can be provided in communication with the scanning device 16. The processing unit 17 can be configured to control the actuated movement of the scanning device for direction of light from the optical delivery fiber 22 to the objective lens 18. The scanning device 16 may also be located in the housing 11, and the housing can be sized for performing endoscopic in vivo surgical procedures on the subject.

Light from the ultra-fast pulsed surgical optical energy source 12, e.g. optical energy 14, that is directed onto the scanning device 16 can be further directed through a quarter wave plate 104 and through a pair of relay lenses 26 and 28 prior to contacting the back aperture 21 of the objective lens 18. The relay lenses 26, 28 may be aspherical lenses. Optionally, the numerical aperture of each relay lens 26, 28 may be about 0.9 or less. At least a portion of the optical energy 14 from the optical energy source 12 that contacts the back aperture 21 of the objective lens 18 may be directed onto target tissue 20 of the subject. The objective lens 18 can be configured to focus optical energy 14 from the optical energy source 12 into a focal volume, where surgical manipulation can occur by the focused optical energy 14. The objective lens can have a numerical aperture of about 0.4 or higher. As described above, properties of the optical energy can be selected to cause photodamage or ablation of tissue in the subject. An actuator device 40, such as an electric motor, can be used to move the housing 11 towards or away from the target tissue 20. Such motion can change the effective focal depth of the optical energy within the tissue being treated.

The system 200 can further include a light source 208 for confocal fluorescence imaging. The imaging light source 208 can be a continuous-wave or pulsed light source, such as that which may be used in conventional confocal fluorescence imaging systems. Optionally, light source 208 can produce light that is visible, or in the near-infrared region of the optical spectrum, and it may be pulsed or continuous wave. Although the light source for surgery 12 and the light source for imaging 208 are depicted separately in FIG. 3, the same light source can be used for both surgery and imaging in other embodiments. Thus, the system 200 can include a single light-emitting component configured to produce optical energy for both imaging and surgery.

The imaging light source 208 can be configured to produce light for confocal fluorescence imaging of biological tissue, referred to herein as imaging light 210. Similar to the optical energy 14, the imaging light 208 can be transmitted along the optical delivery fiber 204, through a collimating lens 203 and onto the scanning device 16. The imaging light 210 can also pass through a dichroic mirror 206 before being transmitted by the optical fiber 204. The imaging light 210 can be further directed through the pair of relay lenses 26, 28 and through the objective lens 18. The objective lens may be configured to transmit imaging light 210 to a region of interest of the target tissue 20.

The objective lens 18 can be further configured to receive light from the target tissue. Light received from the target tissue can include light resulting from excitation of fluorophores in the target tissue, which can be caused by interaction of the imaging light 210 and the target tissue.

At least a portion of the light received by the objective lens 18 from the target tissue 20 can be transmitted to a photodetector 32. The photodetector 32 may be configured to detect at least a portion of the light impinging on it. The photodetector can be provided in communication with at least one processing device 34 that can be configured to produce an image from light detected by the photodetector 32.

Portions of the system 200 can be located in the housing 11 and/or outside of the housing 11. As described above, the housing 11 can be moved towards or away from the target tissue 20 using an actuating device 40. The system 200 can be used to provide surgical manipulation of biological tissue using light from the optical energy source 12 and/or confocal fluorescence imaging of the biological tissue.

An operator may determine whether the system 200 is used for surgical manipulation of biological tissue alone, confocal fluorescence imaging alone, or both surgical manipulation of biological tissue and confocal fluorescence imaging. For example, if only surgical manipulation of biological tissue is desired, the system 200 can be used to transmit optical energy 14 to the target tissue. If only confocal fluorescence imaging is desired, the system 200 can be used to transmit imaging light 210 to the target tissue. If both confocal fluorescence imaging and surgical manipulation of biological tissue is desired, the system 200 can be used to produce and transmit both imaging light 210 and optical energy 14 to the target tissue.

Figure 4:
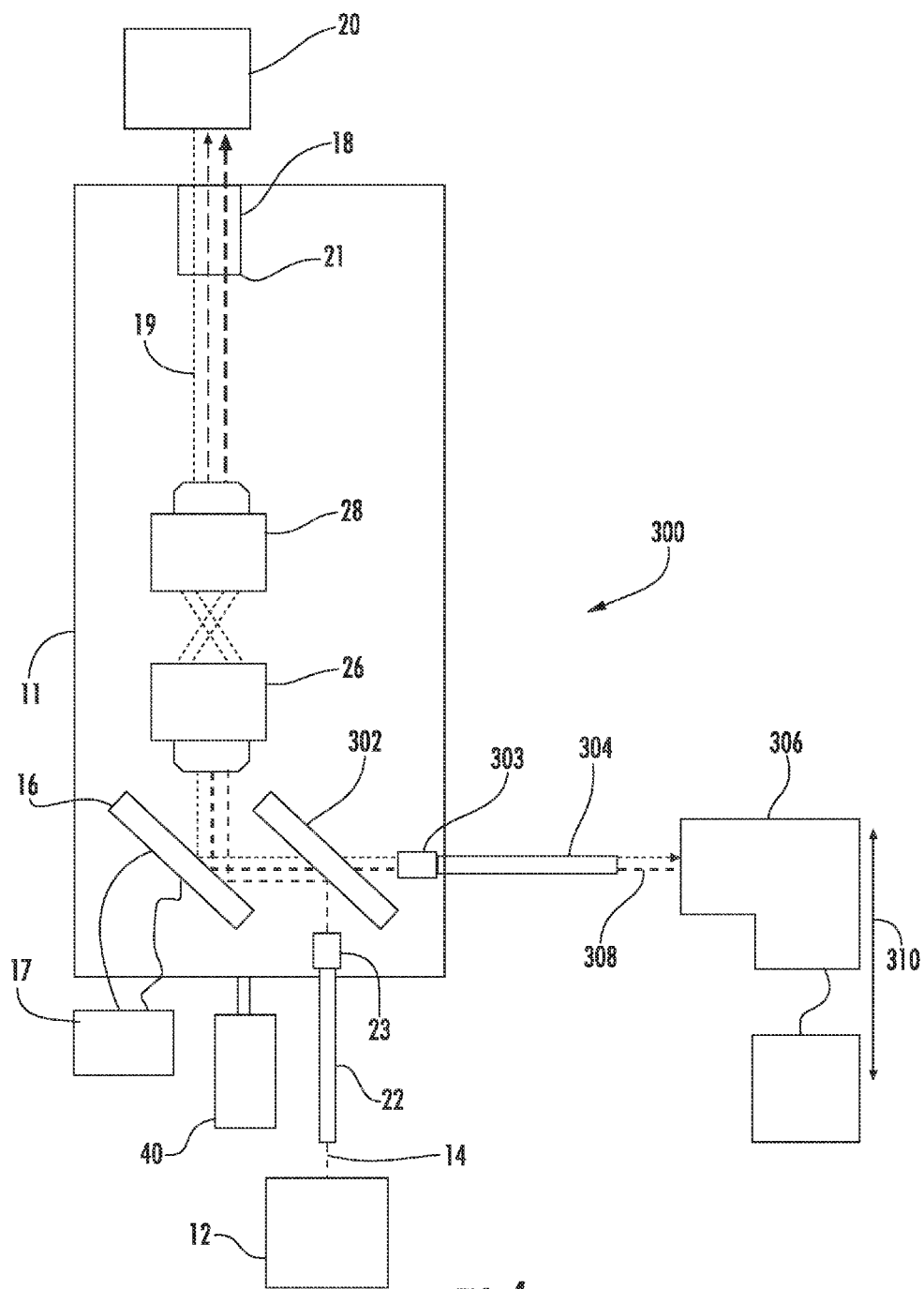
FIG. 4 is a schematic diagram illustrating an exemplary optical coherence tomography (OCT) imaging and surgical system.

FIG. 4 is a schematic diagram illustrating another exemplary system 300 that may be used for surgical manipulation of biological tissue in a subject and/or for optical coherence or optical coherence tomographic (OCT) imaging in the subject. The surgical manipulation of biological tissue and/or the optical coherence tomographic (OCT) imaging can include, e.g., laryngeal microsurgery or imaging of a vocal fold in a subject for treatment or imaging of a vocal fold pathology.

The system 300 includes an ultra-fast pulsed laser optical energy source 12. The optical energy source 12 is configured to produce optical energy for surgical manipulation of biological tissue in the subject. For example, the optical energy source 12 can be configured to produce one or more pulses of optical energy having a duration of about one nanosecond or less. Optionally, the optical energy source 12 may be a picosecond or a femtosecond optical energy source that includes a laser configured to generate one or more laser pulses having a duration on the order of a picosecond or a femtosecond, respectively. The optical energy source 12 can also be configured to produce laser pulses that are near-infrared.

The ultra-fast surgical optical energy source 12 can be provided in communication with an optical delivery fiber 22 or other waveguide. The optical delivery fiber 22 is configured to direct light, e.g. optical energy 14, from the optical energy source 12 into a housing 11. An objective lens 18 can also be provided in conjunction with the housing 11. The objective lens 18 can be configured to receive light generated by the optical energy source 12 that is transmitted into the housing 11 by the optical delivery fiber 22. Optionally, the optical delivery fiber 22 may be an air-core photonic crystal fiber (PCF). Light transmitted along the fiber 22 can be directed through a collimating lens 23, onto a dichroic beam splitter 302 that allows the OCT wavelengths to pass while transmitting the surgery light 14. The dichroic beam splitter 302 can optionally be a hot or cold mirror for direction onto a scanning device 16. In certain embodiments, the optical delivery fiber 22 can be moved to provide scanning of light from the optical energy source 12 instead of using instead of the scanning device 16. For example, the fiber 22 can be translated using a piezoelectric scanning device that is configured to move the fiber to scan light from the optical energy source 12 along or over a portion of the tissue being treated.

The scanning device 16 can be a microelectromechanical (MEMS) scanner. If a MEMS scanner is used, it can be provided, e.g., as a two-axis gimbaled scanner with a reflective surface. The reflective surface can include a reflective coating, e.g., a metal coating. For example, the metal coating can comprise silver or aluminum. The scanning device 16 can be actuated to scan light from the optical delivery fiber 22 for transmission to the objective lens 18. For example, at least one processing unit 17 can be provided in communication with the scanning device 16. The processing unit 17 can be configured to control the actuated movement of the scanning device for direction of light from the optical delivery fiber 22 to the objective lens 18. The scanning device 16 may also be located in the housing 11, and the housing can be sized for performing endoscopic in vivo surgical procedures on the subject.

Light from the ultra-fast pulsed surgical optical energy source 12, e.g. optical energy 14, can be directed onto the scanning device 16 and further directed through a pair of relay lenses, 28 prior to contacting the back aperture 21 of the objective lens 18. The relay lenses 26, 28 can be aspherical lenses. Optionally, the numerical aperture of each relay lens is about 0.9 or less. At least a portion of the light from the optical energy source 12 that impinges on the back aperture 21 of the objective lens 18 can be directed onto target tissue 20 of the subject. The objective lens 18 can be configured to focus light from the optical energy source 12 into a focal volume where surgical manipulation of the tissue can be achieved using the focused optical energy 14. The objective lens can have a numerical aperture of 0.4 or higher. As described above, the optical energy can cause photodamage or ablation of tissue in the subject. An actuator device 40, such as an electric motor, can be used to move the housing 11 towards or away from the target tissue 20 to vary the effective focal depth within the tissue.

The system 300 can further include a light source 306 for OCT imaging. The imaging light source 306 can be, for example, a continuous wave or pulsed light source used in conventional OCT imaging systems. Optionally, light source 306 can be configured to produce light that is broadband, visible, near-infrared, and which may be pulsed or continuous wave. Although the light source for surgery 12 and the light source for imaging 306 are separately depicted in this example, in other examples the same light source can be used for both surgery and imaging. In these other examples, the light source can be adjustable such that it can produce light for surgical application and light for imaging application. Thus, a system comprising an ultra-fast pulsed surgical optical energy source and further comprising an imaging light source can include only one actual light emitting component that can produce light configured for imaging and light configured for surgery.

The imaging light source 306 can therefore be configured to produce light for OCT imaging of biological tissue, referred to herein as imaging light 308. Similar to the optical energy 14, the imaging light 308 can be transmitted along an optical delivery fiber 304, through a collimating lens 303 and onto the scanning device 16. The imaging light 308 can be further directed through the pair of relay lenses 26 and 28 and through the objective lens 18. The objective lens is configured to transmit imaging light 308 to a region of interest of the target tissue 20.

The objective lens 18 is further configured to receive light from the target tissue. Light received from the target tissue can comprise light resulting from the backward scattering of light incident on the target tissue. For example, backward scattering of imaging light 308 can be received by the objective lens 18.

At least a portion of the light received by the objective lens from the target tissue can be transmitted to an OCT imaging system 310. The OCT imaging system 310 is configured to produce an OCT image from light received 19 from the target tissue 20. An exemplary OCT imaging system can optionally comprise a broadband light source, a delay line, an interferometer, and a photodetector. The OCT imaging system 310 can further comprise or be in communication with at least one processing device for producing an OCT image.

Portions of the system 300 can be located in the housing 11. Some portions of the system 300 can also be located outside of the housing 11. As described above, the housing 11 can be moved towards or away from the target tissue 20 using an actuating device 40. The system 300 can be used for surgical manipulation of biological tissue using light from the optical energy source 12. Optionally, the system 300 can be used for OCT imaging in addition to its use for surgical manipulation of biological tissue. The system 300 can also be used for OCT imaging. Optionally, the system 300 can be used for surgical manipulation of biological tissue in addition to its use for OCT imaging.

Whether the system 300 is used for surgical manipulation of biological tissue alone, OCT imaging alone, or both surgical manipulation of biological tissue and OCT imaging can be determined by an operator of the system. For example, if only surgical manipulation of biological tissue is desired, the system 300 can be used to transmit optical energy 14 to the target tissue. If only OCT imaging is desired, the system 300 can be used to transmit imaging light 308 to the target tissue. If both OCT imaging and surgical manipulation of biological tissue is desired, the system can be used to transmit imaging light 308 and optical energy 14 to the target tissue.

Figure 11:
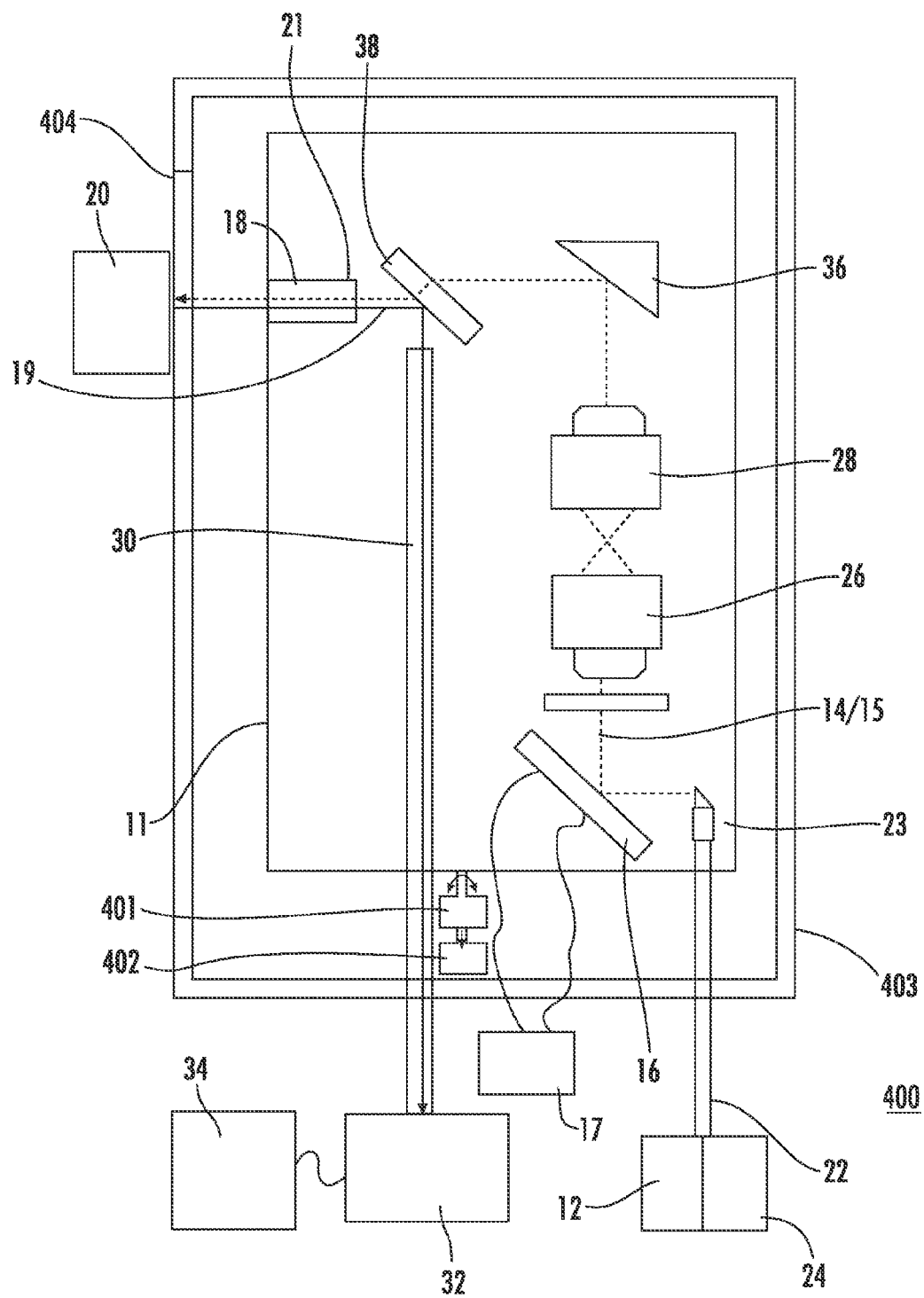
FIG. 11 is a schematic diagram illustrating an exemplary multiphoton imaging and surgical system.

FIG. 11 is a schematic diagram illustrating a further exemplary system 400 for surgical manipulation of biological tissue in a subject and/or multi-photon imaging. The system can be used for imaging and/or surgical manipulation of a vocal fold in a subject. For example, the surgical manipulation and/or multi-photon imaging can include laryngeal microsurgery and imaging of a vocal fold in a subject for treatment or imaging of a vocal fold pathology.

The system 400 includes an ultrafast pulsed laser optical energy source 12. The optical energy source 12 is configured to produce optical energy for surgical manipulation of biological tissue in the subject. For example, the optical energy source 12 can be configured to produce one or more pulse of optical energy having a duration of about one nanosecond or less. Optionally, the optical energy source 12 may be a picosecond or a femtosecond optical energy source, e.g., a laser that is configured to generate one or more laser pulses having a duration on the order of about a picosecond or about a femtosecond, respectively. Optionally, the optical energy source 12 can be configured to have a pulse repetition rate greater than about 250 kilohertz (kHz). For example, the pulse repetition rate may be between about 250 kHz and about 1 megahertz (MHz). In certain embodiments, the pulse repetition rate is at least about 500 kHz. The optical energy source 12 can also be configured to produce laser pulses having wavelengths in the near-infrared region of the optical spectrum. Optionally, the optical energy source 12 can be configured to produce laser pulses with one or more wavelengths in the range of about 600 nm to about 2250 nm.

Optionally, the system 400 further includes a substance configured to be provided within and substantially confined to the sub-epithelial void formed in the vocal fold tissue as described herein to treat the vocal fold pathology. Properties of the substance can be selected to re-establish the pliability of the superficial lamina propria (SLP) in the vocal fold. Re-establishing the pliability of the SLP can restore the voicing capabilities of the subject. To re-establish the pliability of the SLP, the substance can, for example, be a biomaterial. Optionally, the biomaterial comprises collagen, polymeric gel, fat, and/or hyaluronic acid. The biomaterial can, for example, include growth factors (e.g., platelet derived growth factor (PDGF), bone morphogenetic protein (BMP), and/or hepatocyte growth factor (HGF)) and/or stem cells. By creating a void in the vocal fold, the substance can be substantially confined to the volume within the void to effect the treatment. The confined substance can, for example, partially or fully restore the function of the vocal fold and may improve the vocalization of the subject.

The ultra-fast surgical optical energy source 12 can be provided in communication with an optical delivery fiber 22. The optical delivery fiber 22 transmits light, e.g. optical energy 14, 15, from the optical energy source 12 into a housing 11. An objective lens 18 can also be provided in conjunction with the housing 11. The objective lens 18 is configured to receive light generated by the optical energy source 12 that is transmitted into the housing 11 by the optical delivery fiber 22. The objective lens 18 can optionally be a gradient index (GRIN) lens, asperic lens, a spherical lens, a chromatic double, and the like. Z-scanning can be used, which is the scanning of focused optical energy in a direction that is towards or away from a surface of the target tissue. This scanning can be accomplished, e.g., by moving the system 400 or portions thereof towards or away from the target tissue. For example, the objective lens 18 can be actuated to move towards or away from the target tissue using a MEMS actuator or a PZT actuator. Similarly the housing, including the objective lens 18 can be actuated to move towards or away from the target tissue using a MEMS actuator or a PZT actuator. The objective lens 18 itself can be moved, for example, by MEMS devices or piezoelectric devices.

Optionally, the optical delivery fiber 22 may be an air-core photonic crystal fiber (PCF). Light transmitted along the fiber 22 can be directed through a collimating lens 23 and onto a scanning device 16. In certain embodiments, the optical delivery fiber 22 can be moved to provide scanning of light from the optical energy source 12 instead of using a scanning device 16. For example, the fiber 22 can be moved using a piezoelectric scanning device that is configured to translate the fiber to scan light from the optical energy source 12 over or along a portion of the tissue of interest.

The scanning device 16 can be a microelectromechanical (MEMS) scanner. If a MEMS scanner is used, it can be provided, e.g., as a two-axis gimbaled scanner with a reflective surface. The reflective surface can include a reflective coating, e.g., a metal coating. For example, the metal coating can comprise silver or aluminum. The scanning device 16 can be actuated to scan light from the optical delivery fiber 22 for transmission to the objective lens 18. For example, at least one processing unit 17 can be provided in communication with the scanning device 16. The processing unit 17 can be configured to control the actuated movement of the scanning device for direction of light from the optical delivery fiber 22 to the objective lens 18. The scanning device 16 may also be located in the housing 11, and the housing can be sized for performing endoscopic in vivo surgical procedures on the subject. Portions of the system 400 can be referred to as a probe. For example, when the housing 11, or other portions of the system, are configured for surgical manipulation and/or imaging in a human or non-human subject, portions of the system can be referred to as a probe.

Optical energy 14 from the ultra-fast pulsed surgical optical energy source 12 that is directed onto the scanning device 16 can be further directed through a pair of relay lenses 26 and 28 prior to contacting the back aperture 21 of the objective lens 18. Each relay lens of the pair 26 and 28 can be an aspherical lens. Optionally, the numerical aperture of each relay lens is about 0.9 or less. The optical energy 14 from the optical energy source 12 may optionally contact a mirror 36 after passing through the relay lens 28. The optical energy 14 from the optical energy source 12 can also be directed to the objective lens 18 using a hot mirror 38. A portion of the optical energy 14 from the optical energy source 12 that contacts the back aperture 21 of the objective lens 18 may be transmitted onto a region of interest, e.g., target tissue 20 of the subject such as a vocal fold in the larynx.

The objective lens 18 can be configured to focus optical energy 14 from the optical energy source 12 into a focal volume where surgical manipulation can occur by the focused optical energy 14. The objective lens 18 may have a numerical aperture of about 0.4 or higher. As described above, the optical energy 14 can cause photodamage or ablation of tissue in the subject. An actuator arrangement 401, 402, such as an electric motor, can be used to move the housing 11 towards or away from the target tissue 20. Optionally, the actuator arrangement 401, 402 can provide translational and rotational motions to translate the field of view (e.g., the region of laser scanning) along the tissue substantially parallel to the plane of the tissue surface. The actuator arrangement 401, 402 can include separate actuators or motors. For example, it may include one actuator device 401 configured to provide translational movement, and a further actuator device 402 configured to provide rotational movement. Alternatively, the actuator arrangement 401, 402 can include a single device that is configured to provide both translational and rotational movement. In certain embodiments, the system 400, or portions thereof, such as the housing 11, may be moved in a ferrule using a piezoelectric device or micro-motor.

The scanning device 16 can be configured to direct the optical energy transmitted onto the biological tissue across the tissue surface. Optionally, the movement of the housing 11 can be used together with the scanning device 16 to direct the optical energy over a focal area of the tissue surface, such as the vocal fold tissue surface. For example, the housing 11 can be translated relative to the target tissue such that the optical energy is translated across a particular area of the tissue surface. The scanning of the light can be performed along one axis (e.g., a line scan) or along two axes (e.g., a planar scan over the tissue). The actuator arrangement 401, 402 can be configured to rotate the optical system or parts therein such that the line scan or the planar scan is swept circumferentially through the tissue. Optionally, the scan may be swept both circumferentially and longitudinally. The scan can, for example, be achieved by using an actuator to move the entire optical system or, e.g., to move just a single mirror and objective lens.

The system 400 can include an imaging light source 24 configured to provide light suitable for multi-photon imaging, e.g., it can be a pulsed optical energy source. Although the light source for surgery 12 and the imaging light source 24 are depicted separately in FIG. 11, in certain embodiments the same light source can be used to provide optical energy for both surgery and imaging. For example, a single light source may be configured to produce both optical energy 14 and imaging light 15. Optionally, optical energy having the same characteristics can be used for both imaging and surgery. Thus, a system that includes an ultra-fast pulsed surgical optical energy source and an imaging light source can be provided with one optical energy source configured to produce both light configured for imaging and light configured for surgery. The light used for imaging and for surgery may optionally have the same or similar characteristics such as, for example, wavelength and pulse duration.

The imaging light source 24 can therefore be configured to produce light for imaging of biological tissue (e.g., vocal folds of larynx), referred to herein as imaging light 15. Similar to the optical energy 14, the imaging light 15 can be transmitted along the optical delivery fiber 22, through the collimating lens 23 and onto a scanning device 16. The imaging light 15 can be further directed through the pair of relay lenses 26, 28 and through the objective lens 18. Before being transmitted through the objective lens 18, the imaging light 15 can contact the mirror 36 and mirror 38, which guide the imaging light 15 on to the back aperture 21 of the objective lens 18. The objective lens may be configured to transmit imaging light 15 to a region of interest or target tissue 20.

The objective lens 18 can be further configured to receive light 19 from the target tissue 20. Light received 19 from the target tissue 20 can include light resulting from excitation of fluorophores in the target tissue. The excitation of the fluorophores can be caused by interaction of the imaging light 15 and the target tissue. Light received from the target tissue can also result from luminescence from nanoparticles located in the target tissue 20. For example, gold luminescence from nanoparticles can be received. Further, the light received from the target tissue can result from the generation of a second harmonic of light incident on a region of interest of the target tissue. The second harmonic can be produced from the interaction of the target tissue and the imaging light 15.

At least a portion of the light received by the objective lens 18 from the target tissue can be directed to an optical transmitter 30. In the system 400, the hot mirror 38 reflects light from the objective lens 18 into the optical transmitter 30. The optical transmitter 30 can transmit light received from the target tissue to the photodetector 32. The photodetector 32 can be configured to detect at least a portion of the light transmitted along the optical transmitter 30. The photodetector can be provided in communication with at least one processing device 34, which may be configured to produce an image from light detected by the photodetector 32.

Portions of the system 400 can be provided within the housing 11. Some portions of the system can also be located outside of the housing 11. As described above, the housing 11 can be moved towards or away from the target tissue 20 using an actuating device. Optionally, the housing 11 can be located in an outer housing 403. The outer housing 403 can include an aperture comprising a transparent window 404, which can be structured to directly contact the target tissue 20. The aperture may be configured to facilitate transmission of optical energy produced by the optical energy source onto the biological tissue for surgical manipulation. The target tissue 20 can, for example, comprise a vocal fold and the transparent window 404 can be configured to flatten the vocal fold tissue against its exterior surface. Optionally, the inner housing 11 can move relative to the outer housing 403, which may be held stationary against a portion of the tissue being treated, to transmit optical energy over an area of the target tissue 20. Optionally, the inner housing 11 and outer housing 403 can each move relative to the target tissue 20 to transmit light over an area of the target tissue 20.

The system 400 may be used for surgical manipulation of biological tissue using light from the optical energy source 12 and/or for multi-photon imaging of the tissue. An operator may determine whether the system 400 is used for surgical manipulation of biological tissue, multi-photon imaging of the tissue, or for both surgical manipulation and multi-photon imaging. For example, if only surgical manipulation of biological tissue is desired, the system 400 can be used to transmit optical energy 14 to the target tissue. If only multi-photon imaging is desired, the system 400 can be used to transmit imaging light 15 to the target tissue. If both multi-photon imaging and surgical manipulation of biological tissue is desired, the system 400 can be used to transmit both imaging light 15 and optical energy 14 to the target tissue.

Figure 12:
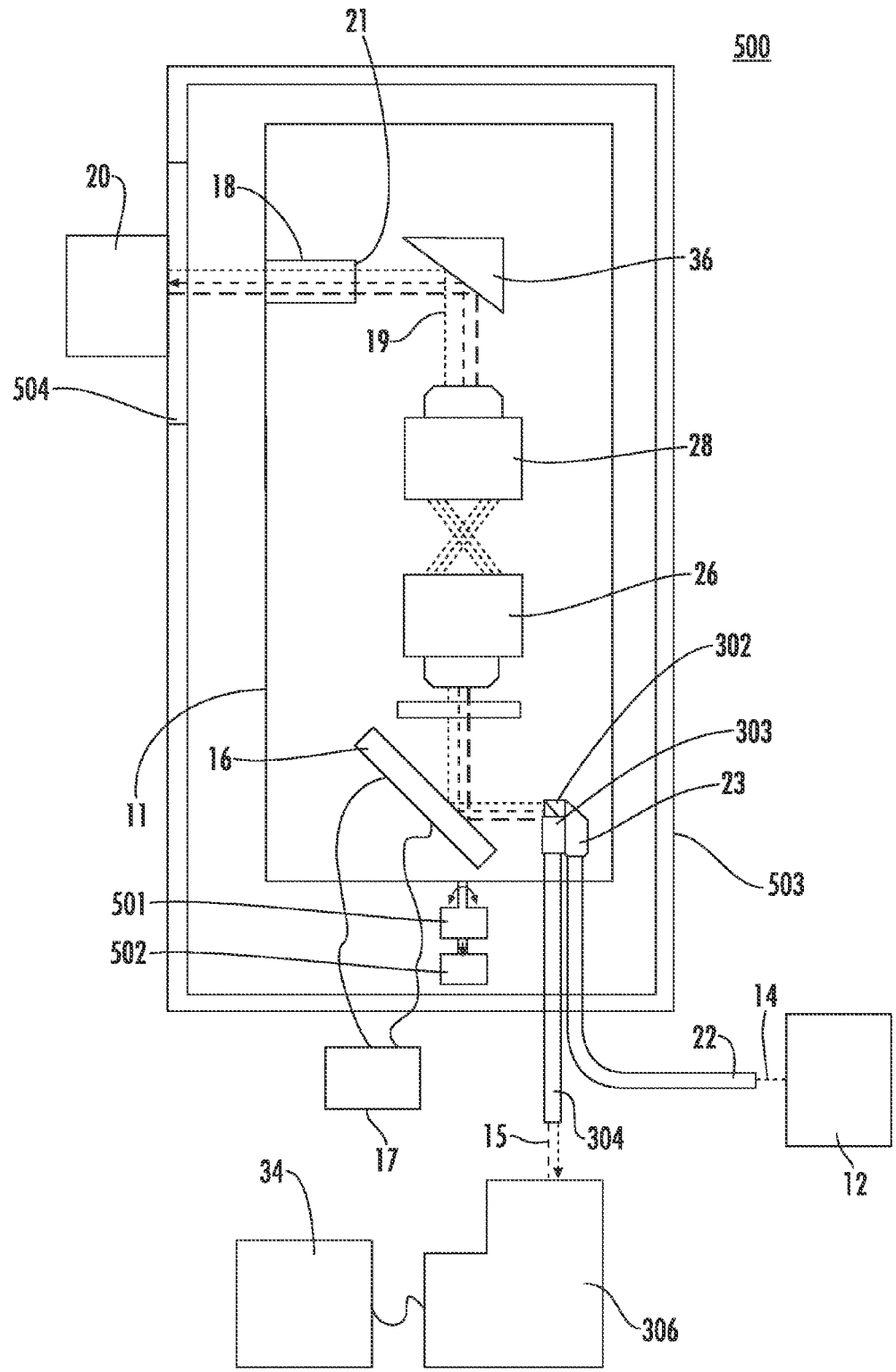
FIG. 12 is a schematic diagram illustrating an exemplary optical coherence tomography (OCT) imaging and surgical system.

FIG. 12 is a schematic diagram illustrating another exemplary system 500, which may be used for surgical manipulation of biological tissue in a subject, as described above, and/or for optical coherence or optical coherence tomographic (OCT) imaging in the subject. The system can be used, for example, for imaging and/or surgical manipulation of a vocal fold in a subject. The surgical manipulation and/or optical coherence or optical coherence tomographic (OCT) imaging can include laryngeal microsurgery and imaging.

The system 500 includes an ultra-fast pulsed laser optical energy source 12. For example, the optical energy source 12 can be configured to produce one or more pulses of optical energy having a duration of about one nanosecond or less. Optionally, the optical energy source 12 may be a picosecond or a femtosecond optical energy source, e.g., a laser that is configured to generate one or more laser pulses having a duration on the order of about a picosecond or about a femtosecond, respectively. Optionally, the optical energy source 12 can be configured to have a pulse repetition rate greater than about 250 kilohertz (kHz). For example, the pulse repetition rate may be between about 250 kHz and about 1 megahertz (MHz). In certain embodiments, the pulse repetition rate is at least about 500 kHz. The optical energy source 12 can also be configured to produce laser pulses having wavelengths in the near-infrared region of the optical spectrum. Optionally, the optical energy source 12 can be configured to produce laser pulses with one or more wavelengths in the range of about 600 nm to about 2250 nm.

Optionally, the system 500 further includes a substance configured to be provided within and substantially confined to the sub-epithelial void formed in the vocal fold tissue as described herein to treat the vocal fold pathology. Properties of the substance can be selected to re-establish the pliability of the superficial lamina propria (SLP) in the vocal fold. Re-establishing the pliability of the SLP can restore the voicing capabilities of the subject. To re-establish the pliability of the SLP, the substance can, for example, be a biomaterial. Optionally, the biomaterial comprises collagen, polymeric gel, fat, and/or hyaluronic acid. The biomaterial can, for example, include growth factors (e.g., platelet derived growth factor (PDGF), bone morphogenetic protein (BMP), and/or hepatocyte growth factor (HGF)) and/or stem cells. By creating a void in the vocal fold, the substance can be substantially confined to the volume within the void to effect the treatment. The confined substance can, for example, partially or fully restore the function of the vocal fold and may improve the vocalization of the subject.

The ultra-fast surgical optical energy source 12 can be provided in communication with an optical delivery fiber 22 or other waveguide. The optical delivery fiber 22 may be structured to direct light, e.g. optical energy 14, from the optical energy source 12 into the housing 11. An objective lens 18 can also be provided in conjunction with the housing 11. The objective lens 18 may be configured to receive light generated by the optical energy source 12 that is transmitted into the housing 11 by the optical delivery fiber 22. Optionally, the optical delivery fiber 22 can be an air-core photonic crystal fiber (PCF). Light transmitted along the fiber 22 can be directed through a collimating lens 23 and onto a dichroic beam splitter 302 that facilitates passage of the OCT wavelengths while transmitting the surgery light 14. The dichroic beam splitter 302 can optionally be a hot or cold mirror, e.g., for directing optical energy onto a scanning device 16. In certain embodiments, the optical delivery fiber 22 itself can be moved or translated to provide scanning of light from the optical energy source 12, instead of using a scanning device 16. For example, the fiber 22 can be moved using a piezoelectric scanning device that is configured to move the fiber to scan light from the optical energy source 12 over a portion of the tissue surface.

The scanning device 16 can be a microelectromechanical (MEMS) scanner. If a MEMS scanner is used, it can be provided, e.g., as a two-axis gimbaled scanner with a reflective surface. The reflective surface can include a reflective coating, e.g., a metal coating. For example, the metal coating can comprise silver or aluminum. The scanning device 16 can be actuated to scan light from the optical delivery fiber 22 for transmission to the objective lens 18. For example, at least one processing unit 17 can be provided in communication with the scanning device 16. The processing unit 17 can be configured to control the actuated movement of the scanning device for direction of light from the optical delivery fiber 22 to the objective lens 18. The scanning device 16 may also be located in the housing 11, and the housing can be sized for performing endoscopic in vivo surgical procedures on the subject. If the housing 11 or other portions of the system are configured for insertion into a subject to provide surgical manipulation and/or imaging of tissue, such portions of the system can be referred to as a probe.

Light from the ultra-fast pulsed surgical optical energy source 12, e.g. optical energy 14, that is directed onto the scanning device 16 can be further directed through a quarter wave plate 104 and through a pair of relay lenses 26 and 28 prior to contacting the back aperture 21 of the objective lens 18. The relay lenses 26, 28 may be aspherical lenses. Optionally, the numerical aperture of each relay lens 26, 28 may be about 0.9 or less. At least a portion of the optical energy 14 from the optical energy source 12 that contacts the back aperture 21 of the objective lens 18 may be directed onto target tissue 20 of the subject. For example, the target tissue 20 can be a vocal fold in the larynx.

The objective lens 18 can be configured to focus light from the optical energy source 12 into a focal volume, where surgical manipulation of the tissue can occur based on the focused optical energy 14. The objective lens can preferably have a numerical aperture of about 0.4 or higher. As described above, the optical energy can cause photodamage and/or ablation of tissue in the subject. An actuator arrangement 501, 502, such as an electric motor, can be used to move the housing 11 towards or away from the target tissue 20. Optionally, the actuator arrangement 501, 502 can provide translational and/or rotational motions to translate the field of view (e.g., the region of laser scanning) along the tissue surface substantially parallel to the plane of the tissue. The actuator arrangement 501, 502 can include separate actuators or motors, for example, where one actuator device 501 is configured to provide translational movement, and the other actuator device 502 is configured to provide rotational movement. Alternatively, the actuator arrangement 501, 502 can include a single device that is configured to provide both translational and rotational movement of the housing 11. In certain embodiments, the system 500 or portions thereof, such as the housing 11, can be moved in a ferrule using a piezoelectric device or micro-motor.

The scanning device 16 can be configured to direct the optical energy transmitted onto the biological tissue across the tissue surface. Optionally, the movement of the housing 11 can be used together with the scanning device 16 to direct the optical energy over a focal area of the tissue surface, such as the vocal fold tissue surface. For example, the housing 11 can be translated relative to the target tissue such that the optical energy is translated across a particular area of the tissue surface. The scanning of the light can be performed along one axis (e.g., a line scan) or along two axes (e.g., a planar scan over the tissue). The actuator arrangement 501, 502 can be configured to rotate the optical system or parts therein such that the line scan or the planar scan is swept circumferentially through the tissue. Optionally, the scan may be swept both circumferentially and longitudinally. The scan can, for example, be achieved by using an actuator to move the entire optical system or, e.g., to move just a single mirror and objective lens.

The system 500 can further include a light source 306 for OCT imaging. The imaging light source 306 can be, for example, a continuous wave or pulsed light source used in conventional OCT imaging systems. Optionally, light source 306 can be configured to produce light that is broadband, visible, near-infrared, and which may be pulsed or continuous wave. Although the light source for surgery 12 and the light source for imaging 306 are separately depicted in this example, in other examples the same light source can be used for both surgery and imaging. In these other examples, the light source can be adjustable such that it can produce light for surgical application and light for imaging application. Thus, a system comprising an ultra-fast pulsed surgical optical energy source and further comprising an imaging light source may include a single light emitting component that can produce light configured for imaging and light configured for surgery.

The imaging light source 306 can therefore be configured to produce light for OCT imaging of biological tissue, referred to herein as imaging light 15. Similar to the optical energy 14, the imaging light 15 can be transmitted along an optical delivery fiber 304, through a collimating lens 303 and onto the scanning device 16. The imaging light 15 can be further directed through the relay lenses 26, 28 and through the objective lens 18. The objective lens may be configured to transmit imaging light 15 onto a region of interest of the target tissue 20.

The objective lens 18 may be further configured to receive light from the target tissue. Light received from the target tissue can include, e.g., light resulting from the backscattering of light incident on the target tissue. For example, backscattered light from the tissue caused by imaging light 15 can be received by the objective lens 18.

At least a portion of the light received by the objective lens from the target tissue can be transmitted to an OCT imaging system 34. The OCT imaging system 34 is configured to produce an OCT image based on light 19 received from the target tissue 20. An exemplary OCT imaging system can optionally include, e.g., a broadband light source, a delay line, an interferometer, and a photodetector. The OCT imaging system 34 can further include or be provided in communication with at least one processing device configured to produce an OCT image based on detected signals.

Portions of the system 500 can be provided within the housing 11. Some portions of the system can also be located outside of the housing 11. As described above, the housing 11 can be moved towards or away from the target tissue 20 using an actuating device. Optionally, the housing 11 can be located in an outer housing 503. The outer housing 503 can include an aperture comprising a transparent window 504, which can be structured to directly contact the target tissue 20. The aperture may be configured to facilitate transmission of optical energy produced by the optical energy source onto the biological tissue for surgical manipulation. The target tissue 20 can, for example, comprise a vocal fold and the transparent window 504 can be configured to flatten the vocal fold tissue against its exterior surface. Optionally, the inner housing 11 can move relative to the outer housing 503, which may be held stationary against a portion of the tissue being treated, to transmit optical energy over an area of the target tissue 20. Optionally, the inner housing 11 and outer housing 503 can each move relative to the target tissue 20 to direct light over a particular area of the target tissue 20.

The system 500 may be used for surgical manipulation of biological tissue using light from the optical energy source 12 and/or for OCT imaging of the tissue. An operator may determine whether the system 500 is used for surgical manipulation of biological tissue, OCT imaging of the tissue, or for both surgical manipulation and OCT imaging. For example, if only surgical manipulation of biological tissue is desired, the system 500 can be used to transmit optical energy 14 to the target tissue. If only OCT imaging is desired, the system 500 can be used to transmit imaging light 15 to the target tissue. If both OCT imaging and surgical manipulation of biological tissue is desired, the system 500 can be used to transmit both imaging light 15 and optical energy 14 to the target tissue.

Figure 17A:
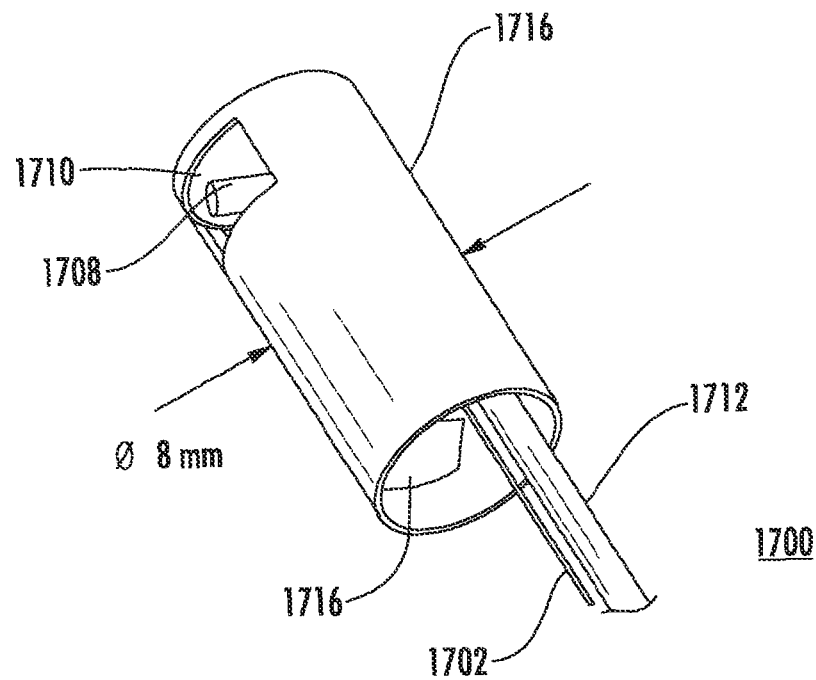
FIG. 17a is a schematic illustration of an enclosed miniaturized phonomicrosurgery probe.
Figure 17B:
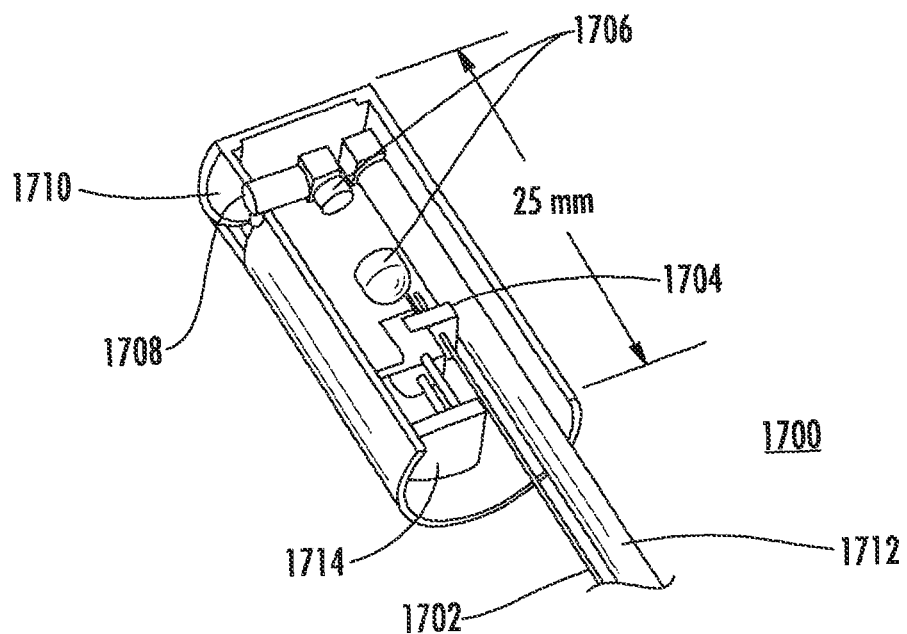

The exemplary optical-based systems described herein can be packaged in a small and flexible probe that can be used access constrained regions. For example, for phonomicrosurgery use, a miniaturized optical system 1700 that may be approximately 8 mm in diameter, illustrated in FIG. 17, can be delivered through a conventional laryngoscope that may be used in larynx/voice box surgeries. In a clinical setting, the surgery probe can be fed through the laryngoscope before the laryngoscope is inserted into the subject's throat. Such probes can provide a large ablation field of view (FOV) while maintaining collagen imaging capabilities, and can deliver optical energy in the form of amplified microsurgical optical pulses having durations on the order of a femtosecond without distortion or damage to optical components.

The exemplary probe 1700 can be coupled to an air bandgap photonic crystal fiber (PCF) 1702 to deliver optical energy from the laser energy source to the optical components in the probe. The femtosecond laser pulses can be transmitted through the air-core PCF 1702 to a single-axis gimbaled MEMS scanning mirror 1704, relay lens pair 1706, and molded aspheric objective lens 1708, which may be configured to focus the optical energy through a viewing window 1710 into the tissue. Components of the exemplary probe 1700 can be mounted to a CNC (computer numerical control)-machined micro-optical table with grooves for self-alignment of the optics. The autofluorescence and second harmonic generation (SHG) signals can be collected from the tissue through the objective lens 1708 and directed to a large-core, high-numerical aperture (NA) collection fiber 1712. The collected light can then be delivered to a photomultiplier tube for detection and subsequent image reconstruction or other signal processing.

Femtosecond laser pulses can be delivered through the air-core photonic crystal fiber 1702, which can use a photonic bandgap material to guide single-mode optical energy through a hollow core. The hollow core can facilitate delivery of fs laser pulses, which have high peak intensities that may generate nonlinear stretching of the pulses in conventional fibers. Also, because material dispersion is significantly reduced or eliminated in such air-core fibers, the air-core fiber 1702 can deliver fs laser pulses without dispersion at a specific wavelength. The fiber can be, for example, an air-6-800, (Crystal Fibre A/S), which has a zero dispersion wavelength of 753 nm that works well with a 500 kHz laser (776 nm) once the beam is appropriately adjusted with a pulse pre-stretcher.

Laser beam scanning can be achieved using a single-axis gimbaled MEMS scanning mirror 1704. MEMS mirrors can provide the advantages of fast scanning speeds (e.g., greater than about 1 kHz) and relatively high deflection angles (e.g., greater than about 20° full optical deflection) in a small footprint.

Maximizing the field-of-view (FOV) while keeping the resolution and energy transmission constant during scanning can be desirable. In large-scale systems, such conditions can be achieved using a relay lens pair 1706, in which the scanning mirror 1704 is imaged to the back aperture of the objective lens 1708. In miniaturized probes, this configuration has generally been compromised in order to use distal, fiber-tip scanning and/or to keep the design compact and simple, both of which may reduce the effective FOV. To address this effect, some optical probe designs may employ a rigid multi-pitch GRIN relay lens; however, the internal focal points in these lenses render them unsuitable for use with ultrashort laser pulses at high laser fluences. Rather than compromise the ablation conditions, embodiments of the present invention can incorporate a relay lens pair 1706 using small aspherical lenses that are commercially available. The aspherical lenses can have diameters as small as about 3 mm. In addition to facilitating use of a full scanning range of the MEMS mirror 1704, the system 1700 can eliminate focal points within the glass and can also expand the beam of optical energy. The beam expansion can allow for use of a smaller beam diameter at the MEMS mirror 1704 to minimize energy loss due to overfilling, while maintaining a larger diameter at the objective lens 1708 to take advantage of its full NA.

Performance of the miniature objective lens 1708 can be improved by switching from a GRIN lens to a small molded glass aspheric lens. Aspheric lenses can provide several advantages, such as a corrected spherical aberration and a greater working distance. For example, a 0.55-NA, 2.4 mm-diameter aspheric lens can provide a 0.88 mm working distance. Such lenses can be obtained, e.g., from LightPath Technologies, Inc. (Orlando, Fla.). The larger NA and diameter of such aspheric lenses can provide more efficient collection of the second harmonic generation (SHG) and autofluorescence signals, while the increased working distance can facilitate imaging through an optical window. By sealing the device behind a window, the system can be partitioned from fluids that may be encountered in clinical applications, and can facilitate sterilization of the device prior to and after its use.

The assembly housing may be constructed using CNC micromachining techniques. The packaging can include an outer housing 1714 that is configured to directly contact tissue, and an inner housing 1716 that encloses the optical system. The inner housing 1716 can be configured to move within the outer housing 1714 to provide large-area scanning of the beam. This inner housing can be provided with fixed grooves in which the optical components can be placed. The outer housing may be substantially cylindrical in shape, and it may include an optical window through which the fs laser pulses can be directed.

The single-axis MEMS scanning mirror 1704 can be configured to scan the beam to ablate a line in the focal plane, which can lie below the surface of the tissue. The line width may be, for example, about 500 microns. While scanning with the MEMS mirror, the inner housing (and thus the optical assembly affixed thereto) can also be rotated around the primary axis of the probe by using a microactuator. The optical assembly can, for example, sweep an area of about 10 mm by about 0.5 mm inside the deformed vocal fold by rotation of the microactuator. After each circumferential scan is complete, a second microactuator can move the entire optics assembly within the outer housing 1714 using step sizes approximately the same as the exemplary 0.5-mm scan width. This second scanning process can provide coverage of approximately 3 mm of axial travel by the optical energy beam along the primary axis of the probe. Various microactuator arrangements can be used in the probe 1700, such as electromagnetic motors or piezoelectric linear actuators.

The probe can be designed to facilitate careful but quick scanning of the optics assembly in order to position the focused beam into the scar tissue. Since a dimension of the scar tissue may be several millimeters in one direction, the probe design can be configured to rotate the entire assembly inside of a transparent cylindrical enclosure to sweep the focal plane. The endoscope can be placed against the vocal fold such that the relatively compliant tissue can be deformed against the optical window. The probe can be held firmly in place by temporarily securing it to the interior of a modified surgical laryngoscope during the procedure with, for example, a small but powerful neodymium magnet or the like. Using the imaging modalities of the probe, the location of the scar tissue can be determined a priori. This information can be used to determine the region of tissue to be subsequently ablated.

The disclosed methods, systems, and devices can be used to image biological tissues in real-time, detect abnormalities, and treat the affected cells/tissues as necessary without the time or expense of conventional biopsy and with greater resolution than conventional diagnostics (MRI, PET, CT, ultrasound, white-light endoscopy). Embodiments of the present invention may be used, e.g., for medical endoscopy (for example, multiphoton fluorescence imaging of epithelial tissues for detection of neoplasia), dermal pathologies, pathologies of the larynx, oral cavity, and esophagus (including but not limited to, cancer), in vivo biological research, and the like.

Figure 13A:
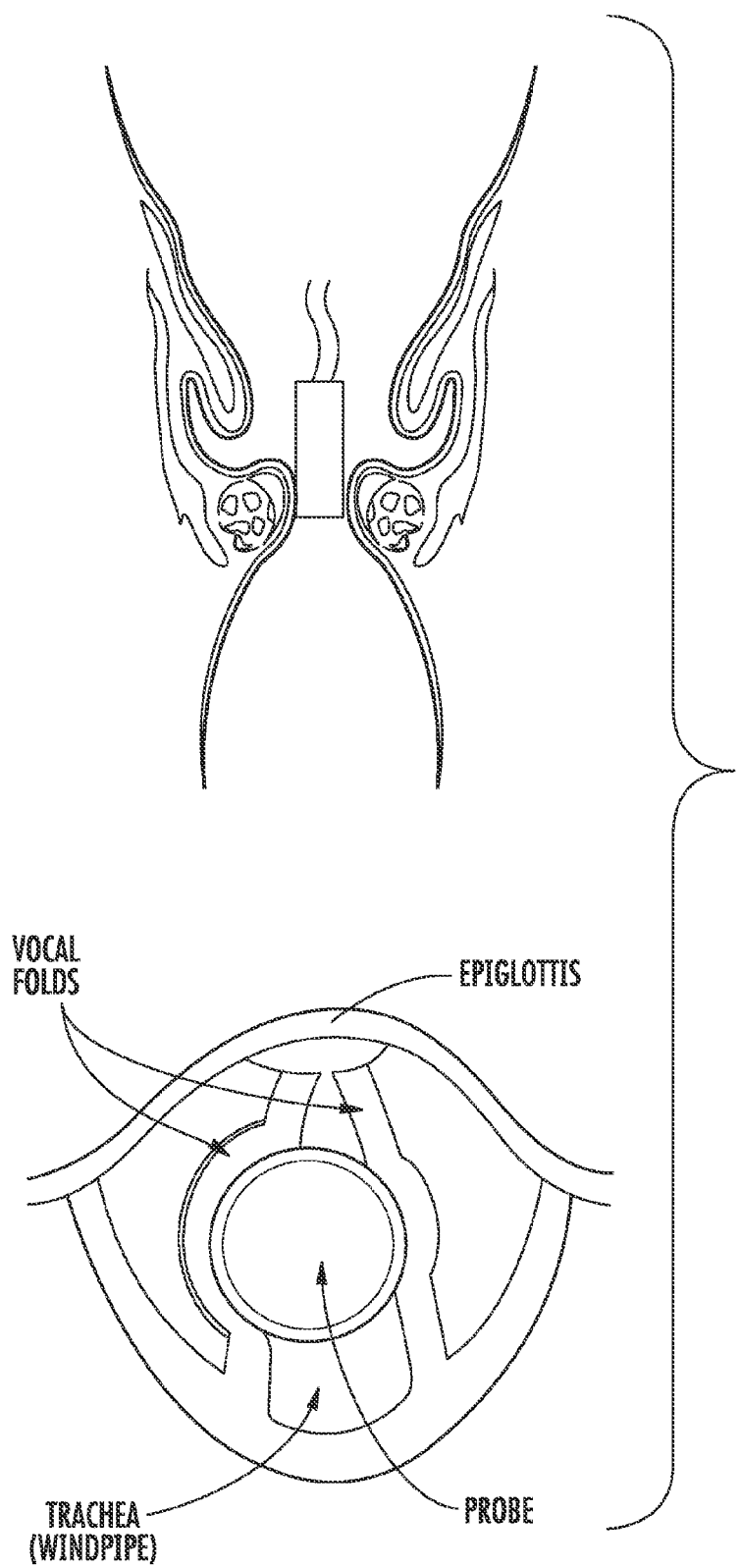
FIG. 13a shows exemplary diagrams of a human vocal fold. The top diagram illustrates a probe device inserted in the larynx of a human. The bottom diagram illustrates a cross-section of the human neck showing the vocal folds, trachea, and epiglottis.
Figure 13B:
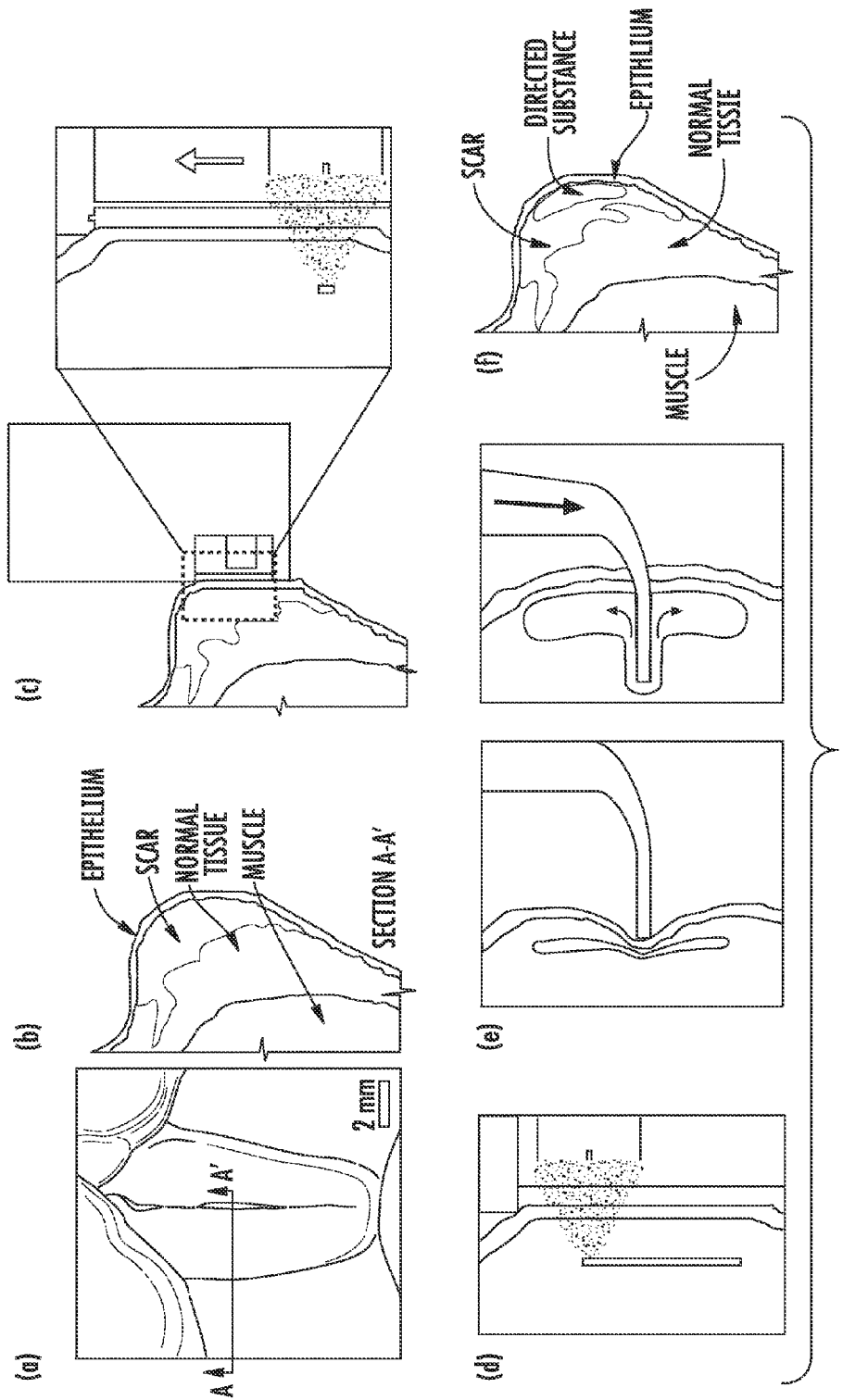
FIG. 13b is a schematic diagram of a method of treating a vocal fold histology.

An exemplary illustration of the human trachea is provided in FIG. 13*a*, and an exemplary method for creating a void and localizing a substance in the void is illustrated in FIG. 13*b*. FIG. 13*b* includes an image of human vocal folds and a diagram of a typical scar formation site (FIGS. 13*b*(a) and 13*b*(b), respectively). The probe device can be positioned against the compliant vocal tissue, deforming the tissue around the optical window of the probe and facilitating both imaging of the scar and ablation of a planar void within the scar (shown in FIGS. 13*b*(c) and 13*b*(d), respectively). The substantially planar void formed using the probe device can optionally be filled with a substance, such as a biomaterial as described above, using a phonosurgery needle to inject the substance (FIG. 13*b*(e)). The void, optionally filled with the biomaterial, can improve the resiliency or pliability of the tissue near the surface of the vocal fold, thus affecting a treatment of the vocal fold pathology (FIG. 13*b*(f)).

Figure 5:
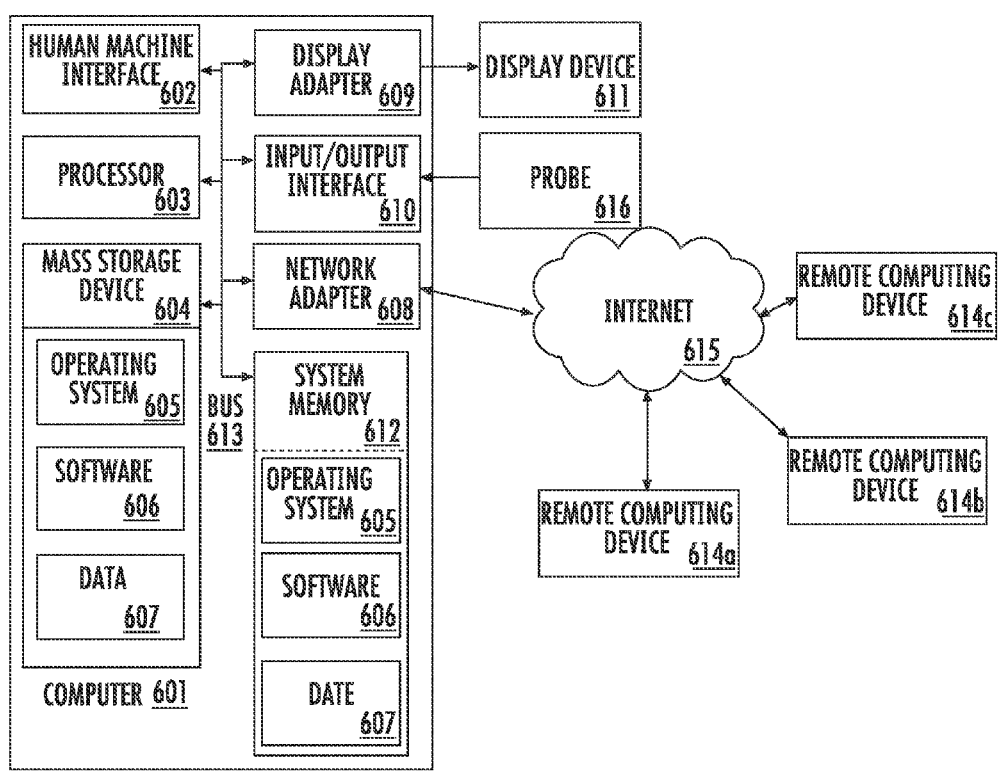
FIG. 5 is schematic diagram illustrating an exemplary operating environment for use with the disclosed systems, devices and methods.

The exemplary systems described herein can include one or more processing devices (e.g. 34 and 17). FIG. 5 is a block system diagram illustrating an exemplary operating environment for using the described systems, devices and methods. One skilled in the art will appreciate that this is a functional description and that certain ones of the various functions shown in FIG. 5 can be performed by software, hardware, or a combination of software and hardware. This operating environment is exemplary in nature and is not intended to suggest any limitation as to the scope of use or functionality of operating environment architecture. Neither should the operating environment be interpreted as having any specific dependency or requirement relating to any one component or combination of components illustrated in FIG. 5.

The present methods, devices and systems can be operated with various other general-purpose or special-purpose computing system environments or configurations. Examples of well-known computing systems, environments, and/or configurations that may be suitable for use with the systems and methods described herein include, but are not limited to, personal computers, server computers, laptops or other portable computing devices, and multiprocessor systems. Additional examples include set-top boxes, programmable consumer electronics, network PCs, minicomputers, mainframe computers, distributed computing environments that include any of the above systems or devices, and the like.

The processing procedures associated with the disclosed methods, devices and systems can be performed by software components. The disclosed systems, devices, and methods can be described in the general context of computer-executable instructions, such as program modules, which may be executed by one or more computers or other devices. Generally, such program modules include computer code, routines, programs, objects, components, data structures, etc. that are configured to perform particular tasks or implement particular abstract data types. The disclosed methods can also be practiced in grid-based and distributed computing environments where tasks are performed by remote processing devices that are linked through a communications network. In a distributed computing environment, program modules can be located in both local and remote computer storage media including, e.g., memory storage devices.

Further, one skilled in the art will appreciate that the systems, devices, and methods disclosed herein can be implemented via a general-purpose computing device in the form of a computer 601 illustrated in FIG. 5. The components of the computer 601 can include, but are not limited to, one or more processors or processing units 603, a system memory 612, and a system bus 613 that couples various system components including the processor 603 to the system memory 612. A computer 601 that includes multiple processing units 603 may utilize parallel computing algorithms and processes.

The system bus 613 represents one or more of several possible types of bus structures, including a memory bus or memory controller, a peripheral bus, an accelerated graphics port, and a processor or local bus using any of a variety of bus architectures. By way of example, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI) bus, also known as a Mezzanine bus. The bus 613, and other buses specified in this description, can also be implemented over a wired or wireless network connection. Various ones of the subsystems, including the processor 603, a mass storage device 604, an operating system 605, software 606, data 607, a network adapter 608, system memory 612, an Input/Output Interface 610, a display adapter 609, a display device 611, and a human machine interface 602, can be contained within one or more remote computing devices 614a,b,c at physically separate locations and connected through buses of this form, in effect implementing a fully distributed system.

The computer 601 may typically be configured to include and/or access a variety of computer readable media. Exemplary readable media can include any available media that is accessible by the computer 601, such as both volatile and non-volatile media, and both removable and non-removable media. The system memory 612 comprises computer readable media in the form of volatile memory, such as random access memory (RAM), and/or non-volatile memory, such as read only memory (ROM). The system memory 612 typically stores data such as data 607 and/or program modules such as operating system 605 and software 606 that can be immediately accessible to and/or operated on by the processing unit 603.

In another embodiment, the computer 601 can include other removable/non-removable, volatile/non-volatile computer storage media. By way of example, FIG. 5 illustrates a general mass storage device 604 that can provide non-volatile storage of computer code, computer readable instructions, data structures, program modules, and other data for the computer 601. Such a mass storage device 604 can be a hard disk, a removable magnetic disk, a removable optical disk, magnetic cassettes or other magnetic storage devices, flash memory cards, CD-ROM, digital versatile disks (DVD) or other optical storage media, random access memory (RAM), read only memory (ROM), electrically erasable programmable read-only memory (EEPROM), and the like.

Optionally, any number of program modules can be stored on the mass storage device 604 including, by way of example, an operating system 605 and software 606. The operating system 605 and/or software 606 can optionally include elements of the programming and the software 606. Data 607 can also be stored on the mass storage device 604. Data 607 may be stored in a form compatible with any of one or more database software packages known in the art. Examples of such database software packages include DB2®, Microsoft® Access, Microsoft® SQL Server, Oracle®, mySQL, PostgreSQL, and the like. The databases may be centralized or they may be distributed across multiple systems.

In certain embodiments, the user can enter commands and information into the computer 601 via an input device. Examples of such input devices include, but are not limited to, a keyboard, pointing device (e.g., a "mouse"), a microphone, a joystick, a scanner, tactile input devices such as gloves, and other body coverings, and the like. These and other input devices can be connected to the processing unit 603 via a human machine interface 602 that is coupled to the system bus 613, and/or can be connected by various other interface and bus structures, including but not limited to a parallel port, a game port, an IEEE 1394 Port (also known as a Firewire port), a serial port, or a universal serial bus (USB).

In yet another embodiment, a display device 611 can also be connected to the system bus 613 via an interface, such as a display adapter 609. It is contemplated that the computer 601 can have more than one display adapter 609 and the computer 601 can have more than one display device 611. For example, a display device can be a monitor, an LCD (Liquid Crystal Display), a digital readout display, a projector, etc. In addition to the display device 611, peripheral output devices can include components such as a speaker or a printer that can be connected to the computer 601 via Input/Output Interface 610. In one embodiment, a probe 616 can be coupled to the computer 601 via Input/Output Interface 610.

The computer 601 can operate in a networked environment using logical connections to one or more remote computing devices 614a-c. By way of example, a remote computing device can be a personal computer, a portable computer, a server, a router, a network computer, a peer device or other common network node, and so on. Logical connections between the computer 601 and a remote computing device 614a-c can be made via a local area network (LAN) and a general wide area network (WAN). Such network connections can be through a network adapter 608. A network adapter 608 can be implemented in both wired and wireless environments. Such networking environments are conventional and commonplace in offices, enterprise-wide computer networks, intranets, and the Internet 615.

For purposes of illustration, application programs and other executable program components such as the operating system 605 are illustrated herein as discrete blocks, although it is recognized that such programs and components may reside at various times in different storage components of the computing device 601, and can be executed by the data processor(s) of the computer. An implementation of software 606 may be stored on or transmitted via some form of computer readable media. Any of the disclosed methods can be performed based on computer readable instructions embodied on computer readable media.

The methods, devices and systems described herein can optionally employ artificial intelligence (AI) techniques or algorithms such as machine learning and iterative learning. Examples of such techniques include, but are not limited to, expert systems, case-based reasoning, Bayesian networks, behavior-based AI, neural networks, fuzzy systems, evolutionary computation (e.g. genetic algorithms), swarm intelligence (e.g. ant algorithms), and hybrid intelligent systems (e.g. Expert inference rules generated through a neural network or production rules from statistical learning).

As used throughout, the term exemplary, is defined herein to mean an example. Thus, for example, an exemplary system is an example of a system, e.g., one that may be provided in accordance with embodiments of the present invention.

As used throughout, a subject can be a vertebrate, more specifically a mammal (e.g. a human, horse, cat, dog, cow, pig, sheep, goat, mouse, rabbit, rat, and guinea pig), a bird, a reptile, an amphibian, a fish, and any other animal. The term 'subject' does not denote a particular age or sex. Thus, both adult and newborn vertebrates, whether male or female, are intended to be covered within the scope of the term 'subject.' The term 'subject' thus can include both human and veterinary subjects. As used herein, 'patient' and 'subject' may be used interchangeably and can refer to a subject with a disease or disorder (e.g. vocal fold pathology).

As used herein, the terms treatment, treat, or treating can refer to a method or procedure for reducing the effects of a disease or symptom of the disease or other physiological condition. Thus in the disclosed method, treatment can refer to a 10%, 20%, 30%, 40%, 50%, 60%, 70%, 80%, 90%, or 100% reduction in the severity of an established disease or symptom of the disease or other condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any other percent reduction in between 10% and 100% as compared to native or control levels. It is understood that treatment does not necessarily refer to a cure or complete eradication of the disease, symptoms of the disease, or other condition.

Disclosed herein are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of various individual and collective combinations and permutations of these compounds may not be explicitly disclosed, such combinations and permutations are specifically contemplated and described herein. For example, if a particular method or system is disclosed and discussed, and certain modifications or optional features or steps are described for the method or system, combinations and permutations of the other described methods and systems that include various ones of the modifications or optional features that are possible are specifically contemplated unless specifically indicated to the contrary. Likewise, any subset or combination of these modifications or optional features is also specifically contemplated and disclosed. This concept applies to all aspects of this disclosure including, but not limited to, steps to be performed in the described methods or components of the described systems. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

All patents and publications cited herein are hereby specifically incorporated herein by reference in their entireties.

EXAMPLE 1

Two-photon Microscopy (TPM) Femtolaser Microsurgery (FLMS) System

Figure 6:
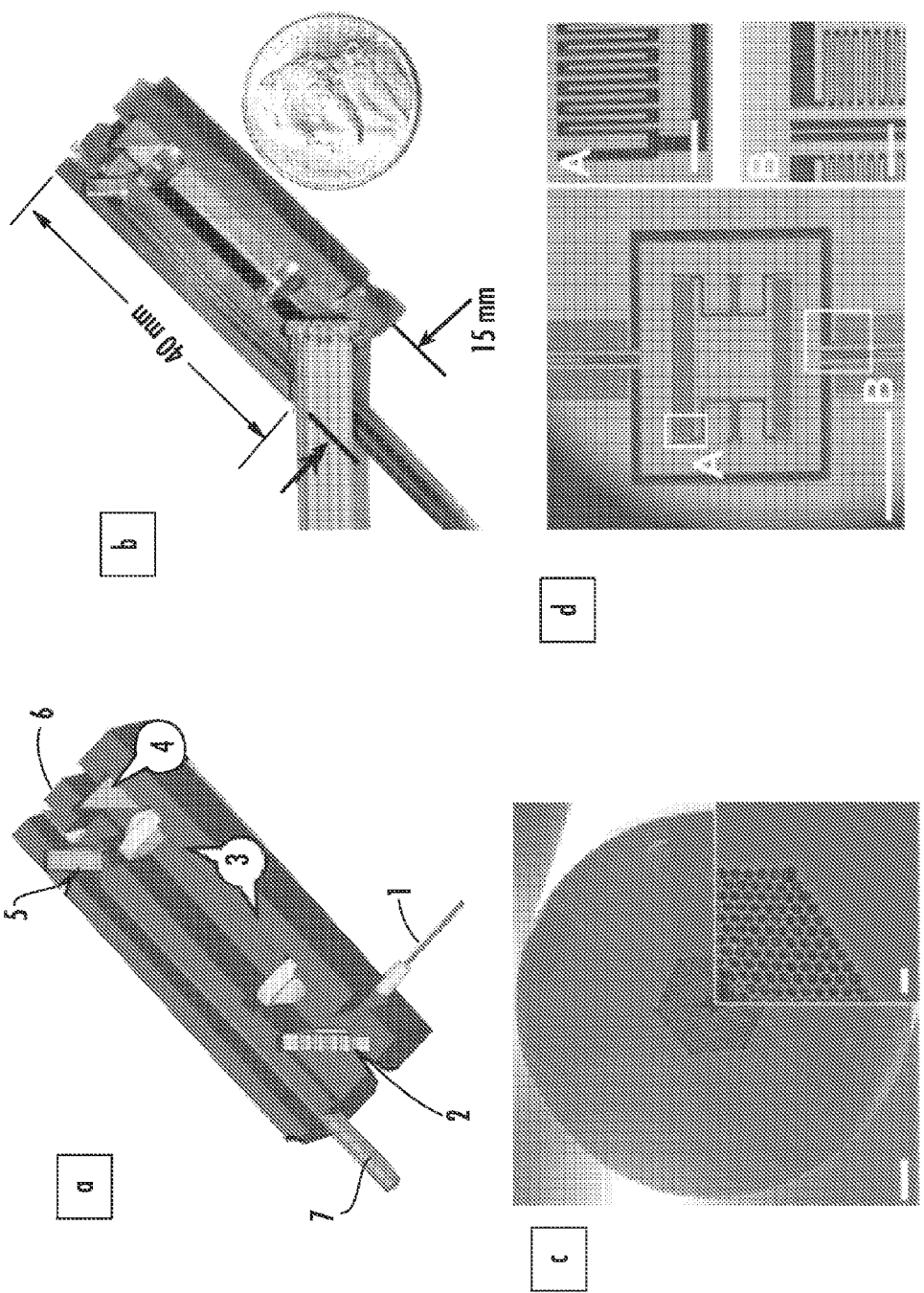
FIG. 6a is a perspective illustration of an exemplary two-photon microscopy and femtolaser microsurgery (TPM/FLMS) probe.
FIG. 6b is a photograph of an exemplary TPM/FLMS probe, indicating relevant dimensions, but not displaying a fiber for optical energy delivery or lid for sealing out stray light.
FIG. 6c is a scanning electron microscope (SEM) micrograph of an exemplary photonic crystal fiber used for delivery of ultrashort optical energy pulses in the system; the scale bar is 15 µm (3 µm inset).
FIG. 6d is a scanning electron microscope (SEM) micrograph of an exemplary micro-scanning device used for scanning and positioning of ultrashort optical energy pulses in the system; the scale bar is 600 µm (120 µm inset).

FIG. 6, is an illustration of portions of an exemplary TPM/FLMS system in accordance with exemplary embodiments of the present invention. The TPM/FLMS system includes a 10 mm×15 mm×40 mm miniaturized two-photon microscope and femtosecond laser microsurgery probe. As shown in FIG. 6a, the probe includes 1) an air-core photonic crystal fiber (PCF) and a gradient index (GRIN) collimating lens, 2) a two-axis MEMS scanning mirror, 3) miniature aspheric relay lenses, 4) a mirror, 5) a hot mirror, 6) a 0.46-NA GRIN objective lens, and 7) a 2 mm-core plastic optical fiber. The image in FIG. 6b shows the probe without the delivery fiber and the lid provided to seal the probe from its surroundings. The PCF delivery fiber and its collimating GRIN lens are mounted separately and aligned to the probe during experiments. FIG. 6c shows two scanning electron microscope (SEM) micrographs (at different magnifications) of the PCF core and cladding structure, where the white scale bar is 15 µm (3 µm in the inset image). FIG. 6d is an image of the MEMS scanning mirror design, where the white scale bar is 600 µm (60 µm for inset A and 120 µm for inset B).

In the exemplary probe shown in FIG. 6a, (1) the air-core fiber facilitates delivery of high peak intensity femtosecond pulses for microsurgery, (2) the relay lenses image the scanning mirror to the back aperture of the objective lens, thus providing a large FOV with uniform excitation, (3) the relay lenses also expand the beam, thus allowing the use of a small and fast MEMS scanning mirror for high frame rates while still overfilling the objective lens aperture for improved resolution, (4) both axes of the MEMS scanner are driven at resonance, allowing the use of low driving voltages to scan a large FOV, and (5) the collection pathway is separated from the excitation fiber and uses a large numerical aperture (NA) fiber, providing improved collection efficiency.

The TPM/FLMS probe can use, e.g., a one meter long air-core PCF (Air-6-800, Crystal Fiber A/S) to deliver femtosecond (fs) pulses of optical energy for both imaging and microsurgery into a 10 mm×15 mm×40 mm Delrin housing (see FIG. 6c). Various lengths of fiber are contemplated, and the fiber length can vary depending on the application. The fiber can have a peak transmission band between about 750 nm and about 800 nm, and may be configured to largely depolarize the laser pulses. Pulses for imaging at an 80 MHz repetition rate were provided by a chirped-pulse amplification system (Mai Tai®, Spectra Physics, Mountain View, Calif.). The pulses were delivered at a minimum-dispersion wavelength of the PCF near 753 nm. The pulse duration was measured to be 152 fs after the fiber for 117 fs input pulse duration using an interferometric autocorrelator. Pulses for microsurgery were provided at a 1 kHz repetition rate using a tunable 80 MHz repetition rate fs pulse laser (Spitfire®, Spectra Physics, Mountain View, Calif.) at a wavelength near 780 nm, the operation wavelength of the chirped pulse amplifier. These pulses were prechirped by adjusting the compressor in the amplifier to compensate for the fiber dispersion, resulting in a pulse duration of 178 fs exiting the fiber. The beam coming out of the fiber was collimated to a $1/e^2$ diameter of 366 μm by a gradient index (GRIN) lens (0.46 NA, 1.8 mm diameter). The fiber tip and its collimating lens were held in a micropositioning stage that was aligned to send the collimated laser beam into the probe housing.

Inside the housing, the laser beam can be scanned using a two-axis gimbaled MEMS scanning mirror. The MEMS scanning mirror can be, for example, a bare silicon mirror, an aluminum-coated mirror, and the like. The mirror can be etched directly onto silicon-on-insulator and can be rotated about two axes using vertical electrostatic combs (see FIG. 6d). The 500 μm×500 μm mirror exhibits resonance frequencies of about 1.54 kHz and about 2.73 kHz. Maximum optical beam deflections of about ±10.5° for the outer axis and about ±10° for the inner axis can be achieved by driving the mirrors with sinusoidal voltage signals at their resonant frequencies using peak voltage values of about 80 volts. Above this voltage, no increase in deflection was observed. The corresponding number of resolvable spots for this exemplary scanning mirror configuration was about 172×232. The collimated beam on the scanning mirror can be imaged onto the back aperture of a GRIN lens (0.46 NA, 210 μm working distance, and 1.8 mm diameter) through an aspherical lens pair, which also serves as a 3.4× beam expander.

In one embodiment, fluorescence emission can be collected by a 2-mm core plastic optical fiber (0.51 NA). The collection fiber can be positioned directly behind a 5 mm×5 mm hot mirror with a cut-off wavelength of about 715 nm. The collected fluorescence can be delivered through a length of the fiber and focused into a photomultiplier tube (H7422-40, Hamamatsu, Bridgewater, N.J.) by a 4 mm focal length lens with a Schott (Duryea, Pa.) BG38 filter cutting scattered optical energy.

For imaging, the laser beam can be Lissajous scanned using a software program to drive both axes of the MEMS mirror at resonant frequencies with sinusoidal voltage signals. Using peak voltage values between about 20 volts and about 80 volts, the diameter of the FOV can be varied over a range between about 36 μm and about 310 μm, respectively. The emission signal can be collected at a 1 MHz rate (1 μs dwell time per pixel) and processed by a computing arrangement to display a 256×256 pixel image at 10 Hz. A variable pixel delay can be included in the processing and display procedures to compensate for a phase delay between the driving voltage and the acquired signal, as well as a phase delay between mirror axes. The pixel delay can be adjusted before imaging to reduce double and quadruple images arising from phase errors in the image reconstruction.

Sample Preparations

For experiments on a single layer of cells, MDMBA468 breast carcinoma cells were cultured in complete L15 medium on a tissue culture dish. Following replacement of the growth medium with a solution of 14 μM calcein AM in Dulbecco's Phosphate Buffered Saline (DPBS), the cells were incubated for 30 min at 37° C. Before imaging, the calcein solution was replaced with fresh DPBS.

For tissue phantoms, MDMBA468 breast carcinoma cells were suspended in a solution of 14 μM calcein AM in DBPS. The cell suspension was then spun down at 200 g for 7 min and resuspended in a buffered solution of high concentration type I collagen (BD Biosciences, San Jose, Calif.). The collagen/cell mixture was pipetted into a 500 μm deep silicon isolator (Molecular Probes®, Invitrogen, Carlsbad, Calif.) and then incubated for 25 minutes before imaging.

Image Processing

Post processing of images and vertical slice reconstructions were handled in ImageJ v1.37a, which is available from the National Institutes of Health, USA. Post-processing comprised averaging over 50 raw frames (5 seconds of imaging time); calibrating pixel dimensions and scaling for square pixels; and low-pass spatially filtering with a fast Fourier transform (FFT) algorithm at 1.2 cycles/μm cut-off frequency in the x and y directions. Filtering eliminated isolated pixels which were not sampled during the Lissajous scan and appear as sub-resolution zero-value pixels aligned in vertical and horizontal rows in the center of the image. The cut-off frequency was based on the measured resolution of the system, so as to not filter out any useful signal. Pixel dimensions were calibrated by moving the sample a known distance using piezoelectric stages and correlating this distance to pixels traversed in the image.

Imaging Characterization

The imaging characteristics (FOV, flatness, and resolution) of the probe were measured before testing the probe's potential for 3D imaging of live cells. To characterize the maximum extent and flatness of the FOV, 1 μm fluorescent beads deposited onto a microscope slide were imaged. FIG. 7a displays a representative image demonstrating a maximum FOV of about 310 μm in diameter. The limiting aperture for the maximum FOV was found to be the clear aperture of the second relay lens in the beam path. A fairly constant intensity over much of the field was observed. The extent of the FOV was varied between about 36 μm and about 310 μm by changing the peak voltage values from about 20 volts to about 80 volts.

Figure 7:
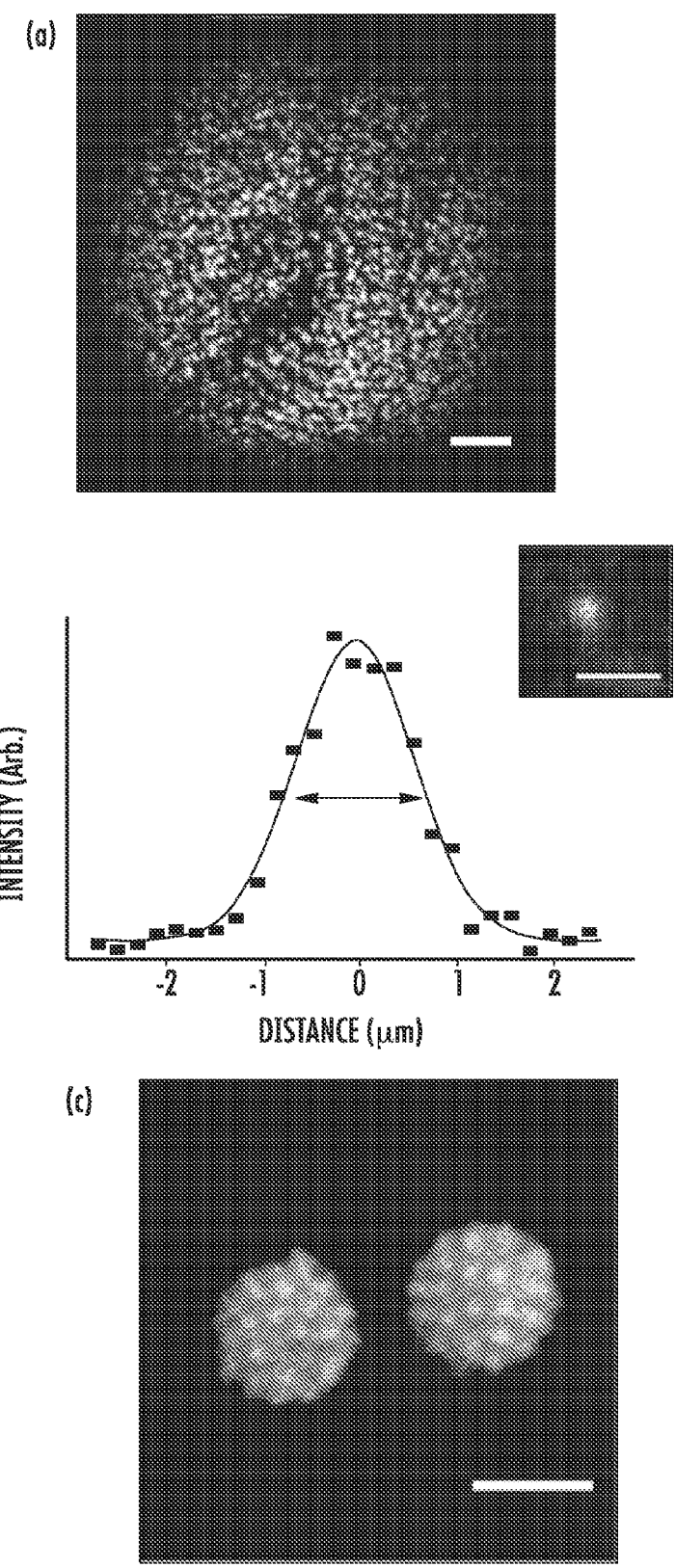
FIG. 7a is an exemplary multiphoton microscopy image of fluorescent beads taken using an exemplary TPM/FMLS probe and demonstrating a field of view (FOV) for this device of about 310 µm; the scale bar is 50 µm.
FIG. 7b is a plot of the lateral fluorescence intensity profile measured during imaging of 100 nm fluorescent beads taken using an exemplary TPM/FMLS probe. Measured values and the Gaussian curve fit are provided, with a full-width at half-maximum value of 1.64 µm; the inset shows an original bead multiphoton image with a scale bar of 5 µm.
FIG. 7c is an exemplary multiphoton microscopy image of fluorescent pollen grains obtained using an exemplary TPM/FMLS probe; the scale bar is 20 µm.

FIG. 7 illustrates two-photon fluorescence imaging characterization of the TPM/FLMS probe. FIG. 7a illustrates 1 μm fluorescent beads on glass, demonstrating a 310 μm maximum FOV. Laser power at the sample was measured to be about 8.2 mW. FIG. 7a represents a six-frame average of the observed fluorescence signals. FIG. 7b illustrates a representative lateral point spread function from 100 nm fluorescent beads provided in agar (shown in inset). Dots represent measured intensity values, while the line represents a Gaussian curve fit to the data. FIG. 7c is an image of two pollen grains. The images shown in FIG. 7b and FIG. 7c represent signals averaged over 5 seconds. FIG. 7a and FIG. 7c were spatially filtered with a low-pass FFT filter. The white scale bars are 50 μm in FIG. 7a, 5 μm in FIG. 7b, and 50 μm in FIG. 7c.

Lateral and axial resolutions were determined experimentally by imaging 100 nm fluorescent beads in an agar gel across a 100 μm FOV to obtain the 3D point-spread function (PSF) of the probe. Using the Rayleigh criterion, the resolution was defined as the full width at half maximum (FWHM) of the Gaussian fit to the lateral and axial intensity profiles of an imaged bead, shown in FIG. 7b. The measured lateral and axial resolutions of the probe were 1.64±0.09 μm and 16.4±1.0 μm, respectively. The measurements were taken across 10 beads. Reported errors correspond to the standard error of the mean value. The extended axial resolution had been previously attributed to spherical aberration from the GRIN lens. The resolution was not observed to vary significantly throughout the FOV, indicating that the beam was well imaged to the back aperture of the objective lens for all scanning angles.

The two-photon imaging capabilities of the probe were demonstrated using pollen grains deposited on a glass slide (30-4264, Carolina Biological Supply Co., Burlington, N.C.). FIG. 7c presents an image of two pollen grains, obtained using a 9.0 mW average laser power directed at the sample. This image indicates the existence of pollen spines and demonstrates the resolving power of the probe at the micrometer scale.

Cellular Imaging

To demonstrate 3D imaging of live cells in a turbid media, a collagen-based tissue phantom with breast carcinoma cells (MDMBA468) was prepared. Phantoms are engineered 3D tissue cultures that mimic optical properties of a real epithelial tissue, and are therefore useful in simulating tissue imaging capabilities. Before suspension in a tissue phantom, the cells were stained with 14 µM calcein acetoxymethyl (calcein AM). Calcein AM is a cell permeable dye that indicates cell vitality when it is converted into fluorescent calcein by esterases found in living cells. Images obtained immediately after uptake and activation of the calcein indicated a uniform fluorescence in the living cells.

Figure 8:
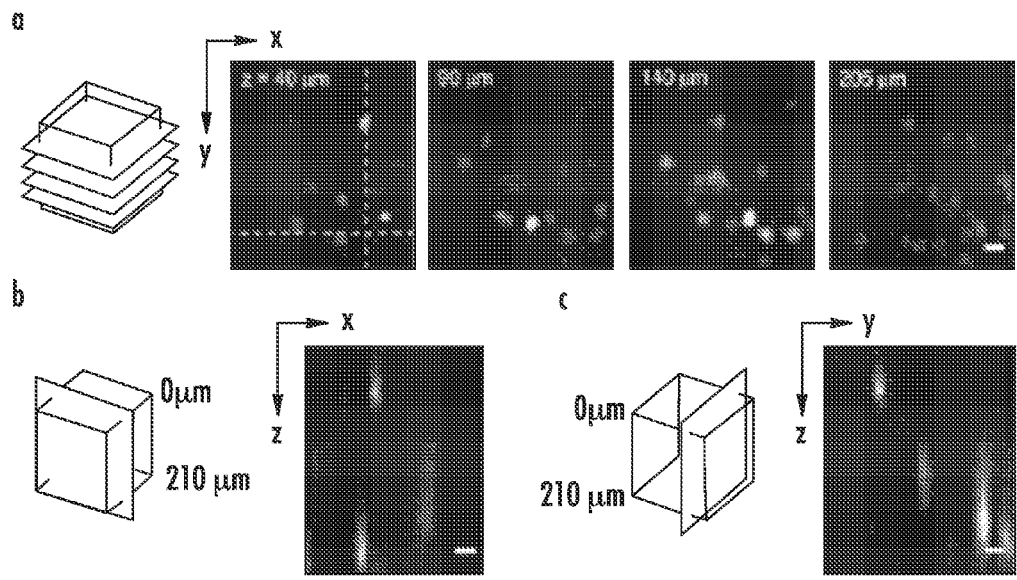
FIG. 8a is an exemplary series of x-y plane images of fluorescently labeled cancer cells in a 3D tissue-like medium obtained using an exemplary TPM/FMLS probe, with images obtained at different depths within the 3D cell volume; the scale bar is 20 µm.
FIG. 8b is an exemplary image of the x-z plane of the sample used in FIG. 8a, reconstructed from images such as those shown in FIG. 8a; the scale bar is 20 µm.
FIG. 8c is an exemplary image of the y-z plane of the sample used in FIG. 8a, reconstructed from images such as those shown in FIG. 8a; the scale bar is 20 µm.

FIG. 8a shows two-dimensional (2D) images of a 182 µm×195 µm lateral FOV taken at various depths below the surface of the tissue phantom. The probe was able to image down to a depth of about 210 µm utilizing the full working distance of the GRIN objective lens. Average power at the sample was measured to be about 17 mW. Despite the existence of scattering and absorption in the phantom, the entire volume was imaged using a substantially uniform laser excitation power. FIG. 8b and FIG. 8c show vertical sections through the imaged volume. The axial spacing between z steps is approximately 6.6 µm and was achieved by translating the sample in the z-direction using a piezoelectric stage. The images in FIG. 8 show the structure and orientation of cells at various depths embedded in a highly scattering media, although the 16.4 µm axial resolution results in an elongation of the cells in the axial direction.

FIG. 8 illustrates three-dimensional imaging of live cancer cells in a tissue phantom. FIG. 8a shows TPM images of a 182 µm×195 µm FOV, taken at various depths beneath the surface. FIGS. 8b and 8c show images of vertical slices reconstructed from lateral images taken 6.6 µm apart. The total imaging depth was 210 µm. The white scale bars in these images are 20 µm.

Cellular Microsurgery

To study the microsurgery capabilities of the exemplary probe, single cells were ablated both in a single cell layer and in a 3D tissue phantom. During these experiments, the cells were imaged before and immediately following ablation. For microsurgery, a flip mirror was used to direct the microsurgery laser into the fiber while the imaging laser was blocked. The MEMS mirror remained static and undeflected during microsurgery, thus targeting the center of the FOV.

FIGS. 9a and 9b present two-photon images of a single layer of live cancer cells before and after femtosecond laser microsurgery, respectively, using a single pulse at 280 nJ pulse energy. Based on the PSF measurement and using the $1/e^2$ diameter (about 2.8 µm), this pulse energy corresponds to a peak laser intensity of about 14 $TW/cm^2$. Ablation of the targeted cell was evidenced by the loss of its fluorescence signal, and the observed abrupt signal loss suggests that the membrane of the targeted cell was ruptured, releasing all of the calcein dye. As only a single laser pulse was used in this experiment, it was expected that the loss in fluorescence was due to ablation rather than photobleaching of the total volume of calcein, which would require longer exposure times. Note that the high precision of fs-laser ablation allowed disintegration of the target cell while adjacent cells remain unharmed.

Figure 9:
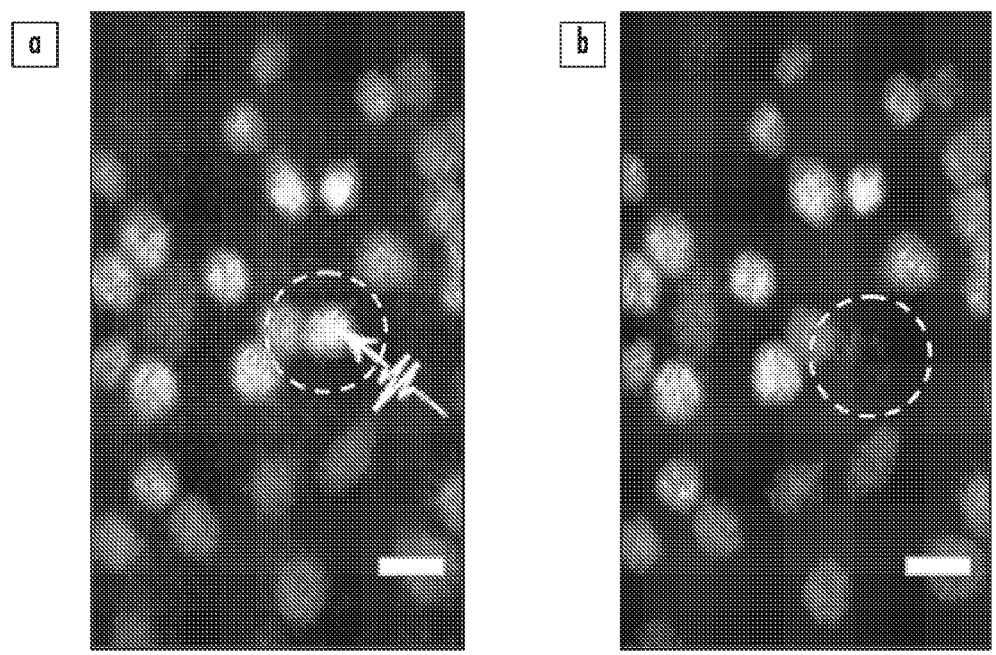
FIG. 9a is an exemplary image of a single layer of labeled cancer cells obtained using an exemplary TPM/FMLS probe before irradiation of the indicated cell by a single ultrashort laser pulse of 280 nJ pulse energy (~14 TW/cm$^2$ peak intensity); the scale bar is 20 µm.
FIG. 9b is an exemplary image of a single layer of labeled cancer cells taken using an exemplary TPM/FMLS probe after irradiation of the indicated cell by a single ultrashort laser pulse of 280 nJ pulse energy (~14 TW/cm$^2$ peak intensity); the scale bar is 20 µm.

FIG. 9 illustrates an exemplary combined two-photon microscopy imaging and femtosecond laser microsurgery of a single layer of breast carcinoma cells. FIG. 9a shows a two photon image of a single layer of live breast carcinoma cells after uptake of calcein AM taken prior to irradiation of the cells with high intensity pulses. FIG. 9b shows the same FOV as FIG. 9a, immediately after irradiation with a single pulse of optical energy at 280 nJ pulse energy. Note that the targeted cell (in the dashed oval) has lost fluorescence while the neighboring cell is left intact.

Figure 10:
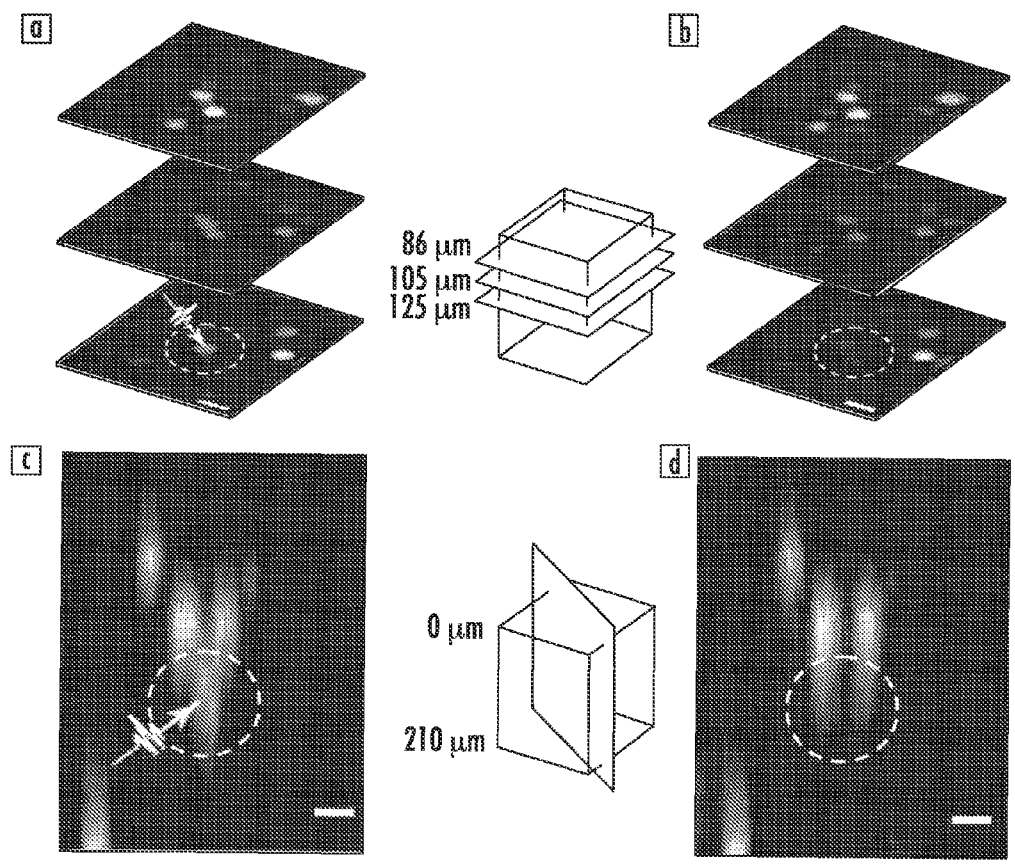
FIG. 10a is an exemplary series of x-y plane images taken using an exemplary TPM/FMLS probe of fluorescently labeled cancer cells in a 3D tissue-like media, with images obtained at different depths within the 3D cell volume before irradiation of the indicated cell; the scale bar is 20 µm.
FIG. 10b is an exemplary series of x-y plane images taken using an exemplary TPM/FMLS probe of fluorescently labeled cancer cells in a 3D tissue-like media, with images taken at different depths within the 3D cell volume after irradiation of the indicated cell by 5000 ultrashort laser pulses of 213 nJ pulse energy; the scale bar is 20 µm.
FIG. 10c is an exemplary image of the sample used in FIG. 10a, reconstructed from images such as those shown in FIG. 10a to give a vertical representation of the sample; the scale bar is 20 µm.
FIG. 10d is an exemplary image of the sample used in FIG. 10b, reconstructed from images such as those shown in FIG. 10b to give a vertical representation of the sample; the scale bar is 20 μm.

Ablation of cells was also investigated within a breast carcinoma tissue phantom. FIG. 10 presents images where a cell approximately 125 µm deep within the phantom was targeted for ablation and destroyed. Here, 5000 pulses at about 213 nJ per pulse were used. In this case, the immediate loss of cellular fluorescence was observed after irradiation with the microsurgery laser, while the cells closest to the target remained intact. In addition to demonstrating microsurgery of cancer cells in turbid media, these images also demonstrate the utility of the probe for optically-based detection and ablation. Femtosecond laser ablation of subsurface cells in tissue provides a noninvasive technique for removing cells in sensitive areas, such as neural tissue.

FIG. 10 illustrates combined two-photon microscopy imaging and femtosecond laser microsurgery of breast carcinoma cells in a collagen tissue phantom. FIG. 10a shows lateral sections of the phantom with a FOV of 116 µm×160 µm depicting a cell targeted for ablation, and the cells above it. FIG. 10b shows the same cells shown in FIG. 10a after irradiation of the targeted cells with 5000 pulses of optical energy at 213 nJ pulse energy. FIG. 10c and FIG. 10d illustrate a vertical slice through the same targeted cell and the cells above it before and after laser irradiation, respectively. The total imaging depth was 210 µm and the axial spacing between lateral slices was 6.6 µm. The white scale bars in these images are 20 µm.

The laser dosages used for the two-photon imaging were estimated to be at a safe level for cell vitality, which can be important for sensitive clinical applications. Cell viability depends on both the incident peak laser intensity and the number of pulses at this intensity that the cell receives. Thus, for comparison purposes, the number of overlapping consecutive pulses was estimated as well as their peak intensity. The number of overlapping pulses was defined as the laser repetition rate divided by the product of the spot size and the scanning speed. The slow axis MEMS scanning frequency and the approximately 116 µm FOV of the exemplary probe were used to arrive at a conservative estimate of scanning speed. Based on the peak intensity, the maximum average power used during cell imaging (17 mW used for imaging in the tissue phantom) corresponded to a peak intensity in the sample of about 13 $GW/cm^2$, which was below the maximum peak intensities found to be safe for long-term two-photon imaging procedures. In addition, the fast scanning speed used in the probe resulted in far fewer consecutive pulses delivered per spot at this intensity, which further reduced the effective overall laser dosage to the sample when imaging with the probe.

MEMS mirrors with high reflectivity in the NIR and miniature objective lenses with minimal spherical aberrations and higher NAs can be used for autofluorescence imaging capabilities, for example, to image weak fluorophores such as those found naturally within living cells. This autofluorescence signal may be useful in many potential clinical applications for providing additional diagnostic information.

Two-photon contrast agents, such as bright luminescent gold nanorods, can be used to reduce the required excitation power by orders of magnitude in addition to providing molecularly specific imaging. Accordingly, a TPM/FLMS probe can be provided that is configured to perform microsurgery using precise femtosecond laser ablation and to provide 3D visualization of the operation region using two-photon imaging techniques.

In certain embodiments, imaging can be accomplished by Lissajous scanning of a two-axis gimballed MEMS mirror, achieving a maximum FOV of about 310 μm and lateral and axial resolutions of about 1.64 μm and about 16.4 μm, respectively. The probe can incorporate an axial scanning arrangement, which may include a micro-motor, a piezoelectric device, or a MEMS device configured to translate individual components or the entire optical system for fully-automated three-dimensional imaging. In certain embodiments, femtosecond laser microsurgery can be accomplished by delivering precompensated laser pulses having pulse energies of up to about 280 nJ through an air core PCF.

EXAMPLE 2

Figure 14A:
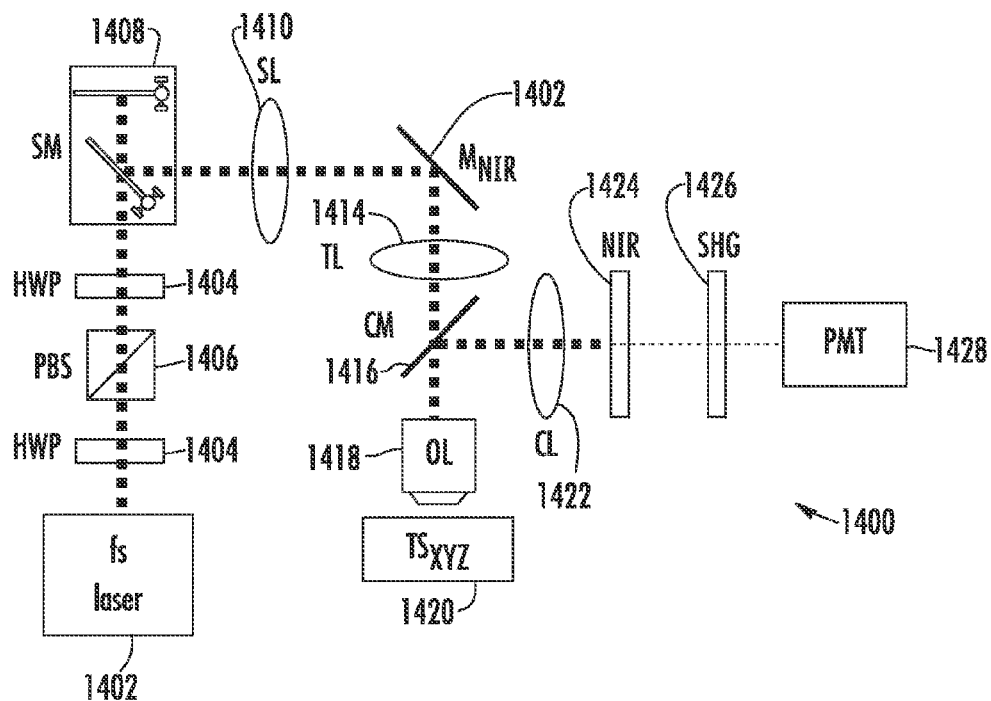
FIG. 14a is a schematic diagram illustrating an exemplary two-photon imaging and microsurgery system.

Femtosecond Laser Microsurgery (FLMS) and Nonlinear Optical Imaging (NOI) of Excised Vocal Fold Tissue Healthy, excised pig vocal folds were subjected to image-guided laser microsurgery to create a void and to locate a substance in the void. The image-guided laser microsurgery on the pig vocal folds used an exemplary femtosecond laser microsurgery (FLMS) system 1400 with TPM capabilities (FIG. 14A). The FLMS system 1400 with TPM capabilities includes a femtosecond (fs) laser 1402, a half-wave plate (HWP) 1404, a polarizing beam splitter (PBS) 1406, scanning mirrors (SM) 1408, a scan lens (SL) 1410, a near-infrared mirror ($M_{NIR}$) 1412, a tube lens (TL) 1414, a cold-mirror (CM) 1416, an objective lens (OL) 1418; a translation stage (TSXYZ) 1420, a collection lens (CL) 1422, a near-infrared filter (NIR) 1424, a second-harmonic generation filter (SHG) 1426, and a photomultiplier tube (PMT) 1428.

Figure 14B:
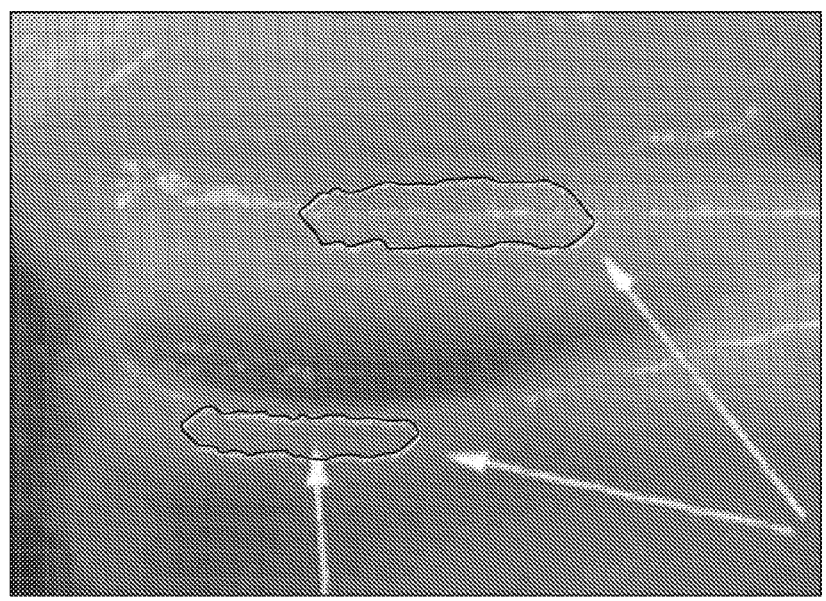
FIG. 14b is an image of an excised and bisected porcine larynx showing a portion of the vocal fold tissue.
Figure 14C:
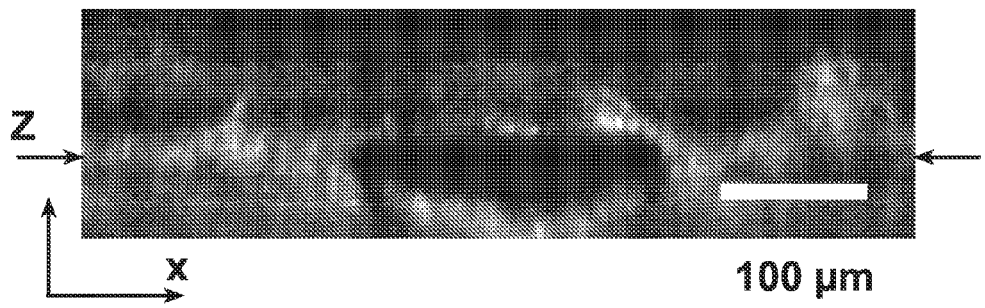
FIGS. 14c-14f are images of laryngeal tissue showing a series of voids ablated using 750 nJ pulse energy at 100 μm below the epithelial surface.
Figure 14D:
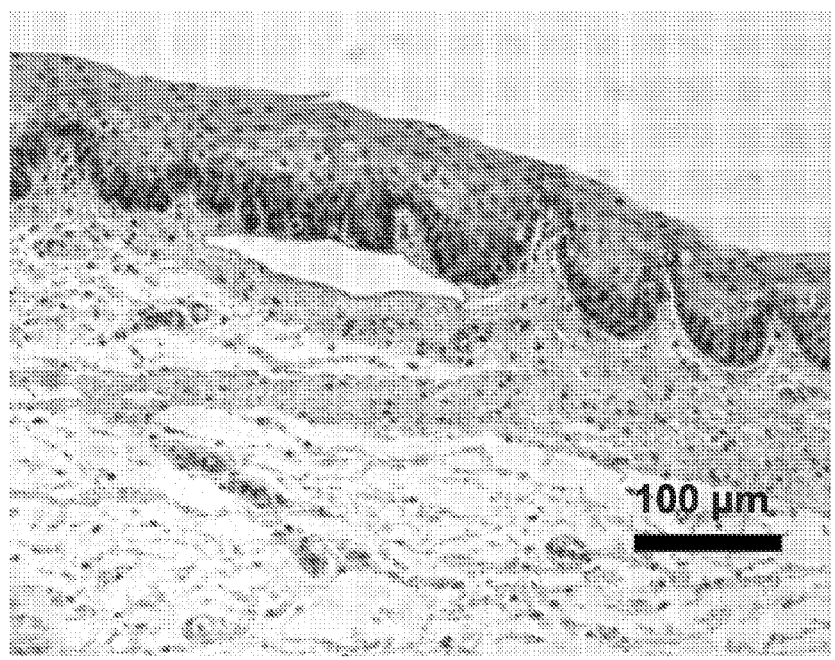
Figure 14E:
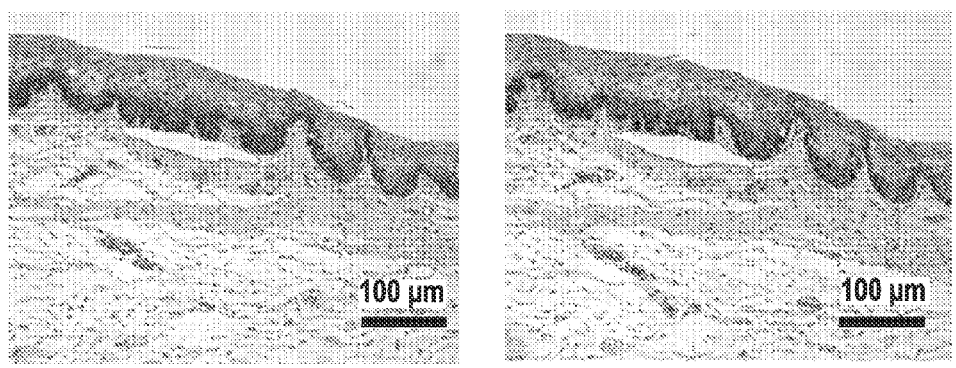
Figure 14F:
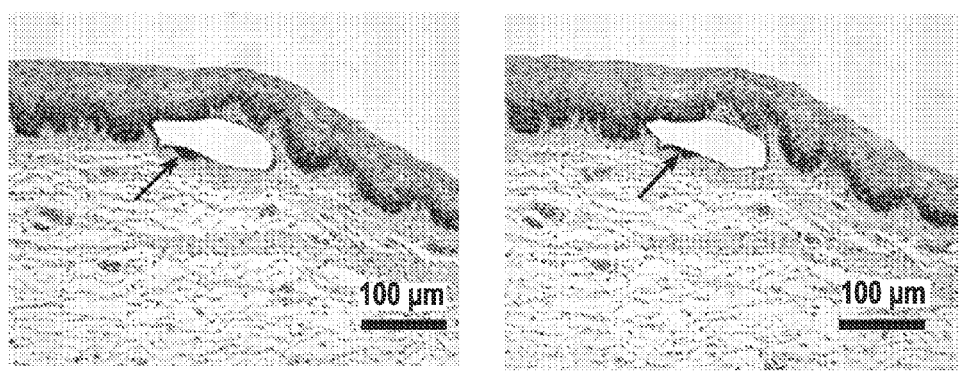
Figure 15A:
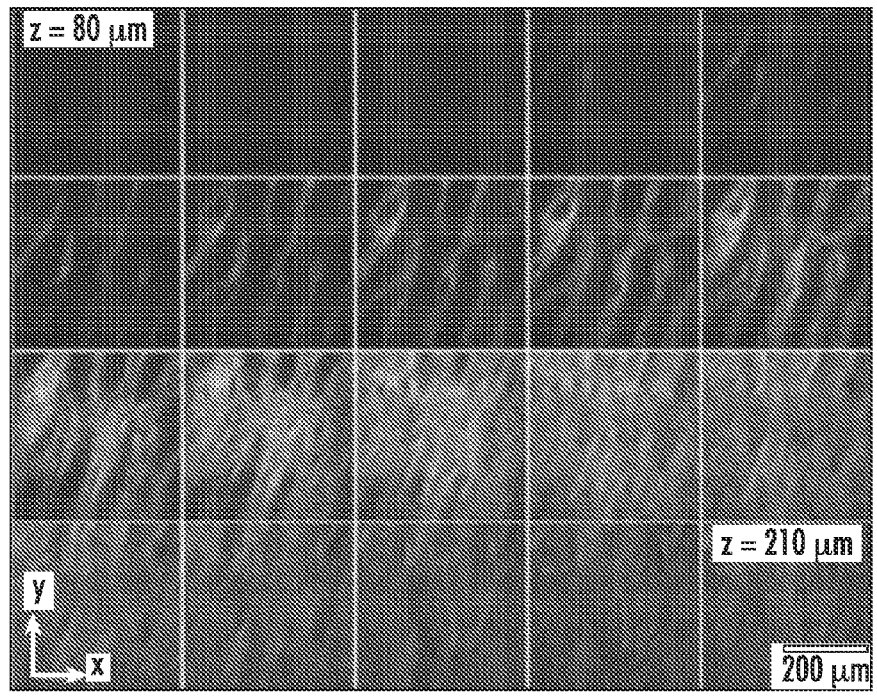
FIG. 15a shows X-Y images of autofluorescence and second harmonic generation (SHG) of porcine vocal folds at increasing depth (z) into the vocal folds.
Figure 15B:
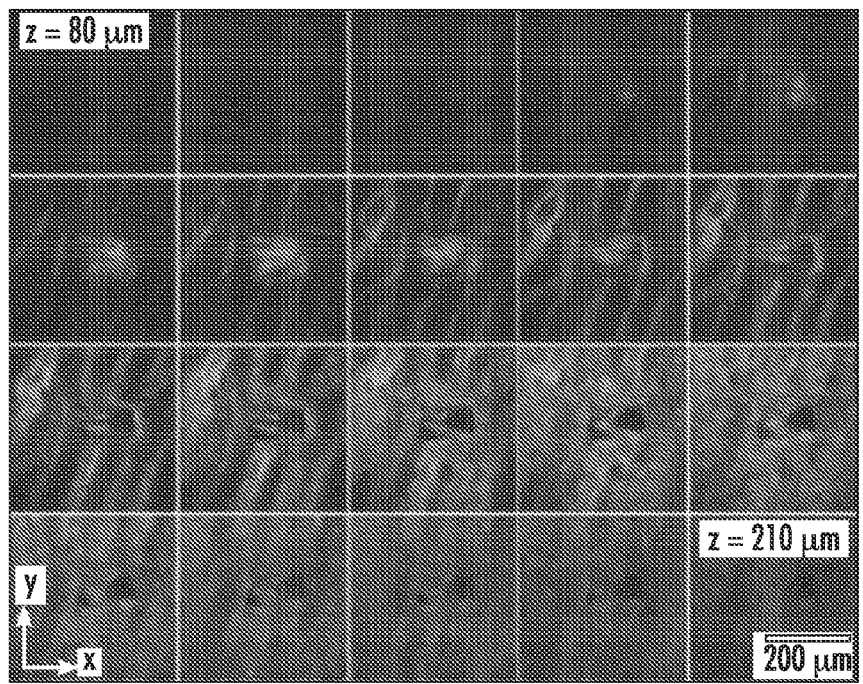
FIG. 15b shows X-Y images of autofluorescence and second harmonic generation (SHG) of porcine vocal folds at increasing depth (z) into the vocal folds after ablation of tissue therein.
Figure 16A:
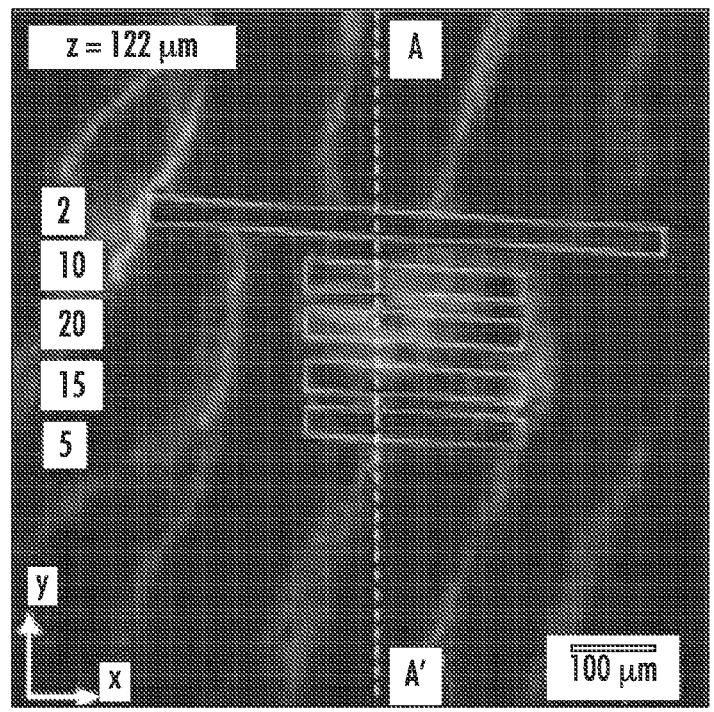
FIG. 16a is a single, magnified X-Y image showing a number of overlapping pulses (boxes) for each ablated channel.
Figure 16B:
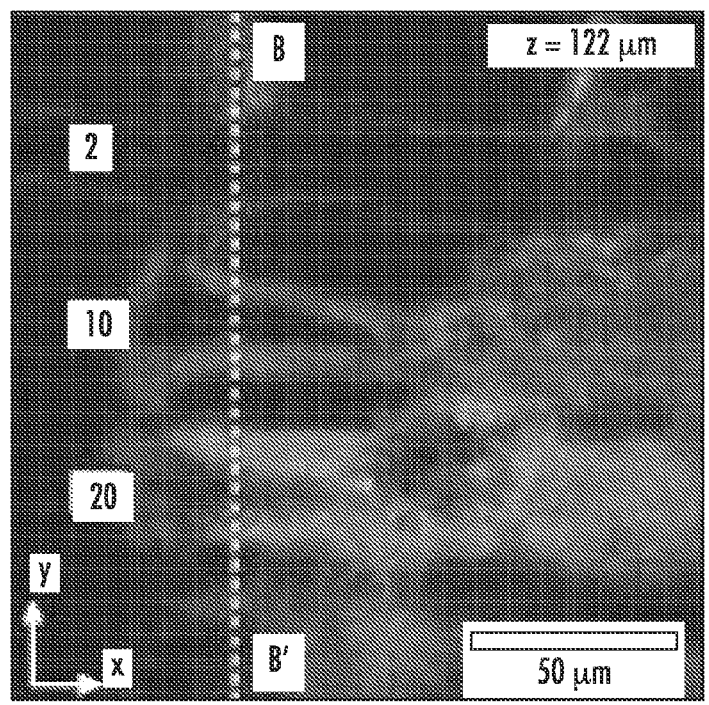
FIG. 16b is an image of the same region shown in FIG. 16a taken at a higher magnification.
Figure 16C:
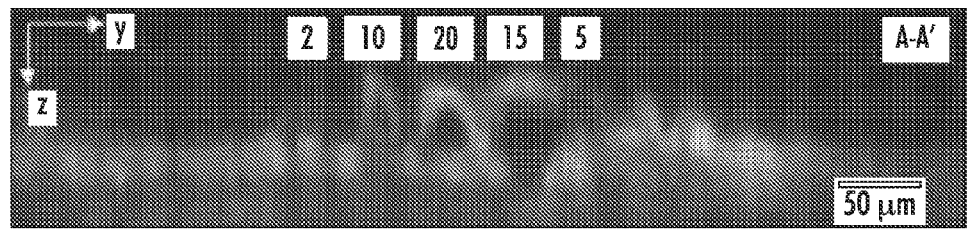
FIG. 16c is a Z-Y image of the same region shown in FIG. 16a, indicating the depth of the ablated voids.
Figure 16D:
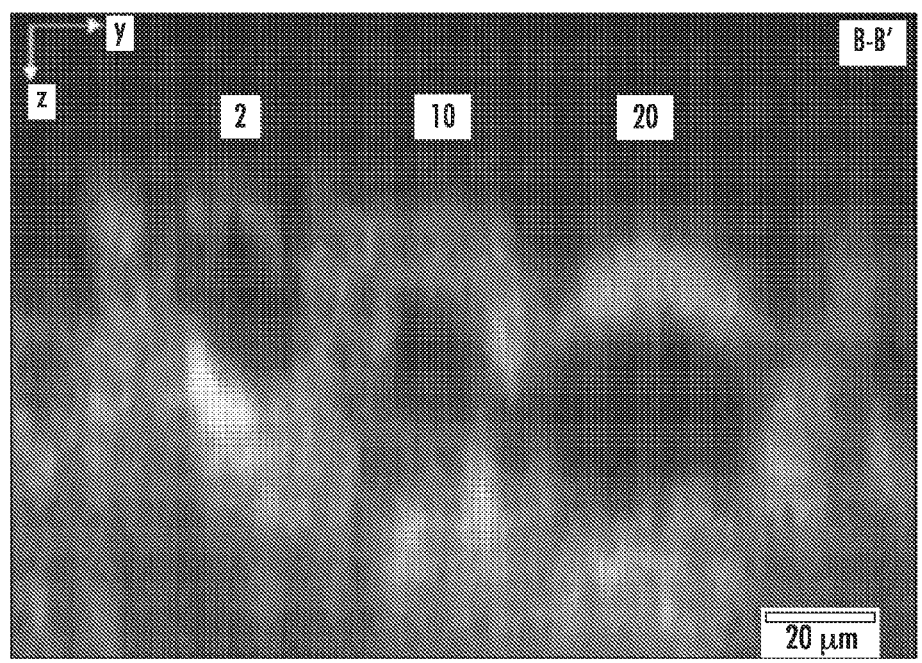
FIG. 16d is an image of the same region shown in FIG. 16c taken at a higher magnification.

A pig larynx (FIG. 14B) was removed, bisected, snap-frozen in liquid nitrogen, shipped, and rapidly thawed to room temperature. Vocal fold tissue was excised from the pig larynx with a scalpel. The vocal fold tissue was placed against the glass optical window of a modified polystyrene cell culture dish and oriented such that the most-midline portion of the vocal fold's superficial lamina propria (SLP) was perpendicular to the glass. The culture dish was then filled with room-temperature isotonic 0.9% saline solution through two pre-drilled holes and sealed with paraffin to prevent evaporation. In the table-top microscope, the specimen was situated on a three-axis translation stage (Thorlabs NanoMax®; Newton, N.J.) with a spatial addressability of approximately 200 nanometers (nm).

FIGS. 14c-f show a series of voids ablated using the system 1400 using 750 nJ pulse energy, 100 μm below the epithelial surface. Void dimensions agreed well with second harmonic imaging, with a width calculated using imaging at 215 μm and a centerline depth of 97 μm and calculated using histology of a width of 175 μm and a 99 μm centerline depth.

FIGS. 15a, 15b, and 16a-16d present autofluorescence and second-harmonic generation (SHG) images of tissue at different imaging depths between 80 and 210 μm, before and after ablation. Nonlinear imaging was performed using a 0.95-numerical aperture (NA) water-dipping objective with a measured lateral resolution of about 675 nm and a field of view (FOV) of about 560 μm. Autofluorescence and SHG signals were detected by a photomultiplier tube.

To identify the fastest speed at which the vocal fold SLP could be successfully ablated at a practical depth, an exemplary FLMS procedure was performed to create a series of voids at various translation speeds. The translation speed determined the number of overlapping pulses that were delivered to a spot in the tissue during rastering of the sample. The dimensions of each ablated subsurface void were about 20 μm wide (y-axis) by about 150 μm long by about 30 μm deep (z-axis) in order to help confirm that a void was indeed created. All voids were formed with 500 nJ pulses at a 1 kHz repetition rate using a chirped-pulse amplification system (Spitfire®, Spectra Physics; Mountain View, Calif.). Following ablation, TPM was performed with a tunable 80 MHz repetition rate fs pulse laser (Mai Tai®, Spectra Physics; Mountain View, Calif.) to analyze the voids formed within the vocal fold tissue. It was observed that the void/tissue interface of the ablated regions exhibited a strong fluorescent signal (shown in FIGS. 15b and 16a-16d). This type of photodamage signal can be useful for locating and confirming ablation zones in vivo, provided that a direct correlation between tissue ablation and the presence of fluorescent scarring can be established.

The extent of scarring in different subjects may vary, with the degree of associated dysphonia related to the degree of and location of the scarring. Vocal fold scarring is typically superficial because of the injury mechanisms involved, whether due to epithelial disease, surgical trauma, or vocal fold collision trauma. The depth of the scar can extend deep (e.g., up to about 500 μm) into the lamina propria of the vocal fold. However, it is desirable to form a void within the scar tissue as close as possible to the epithelial layer to improve the resiliency/flexibility thereof, and to optionally introduce a pliable substance into such void. Therefore, voids may be formed at a depth between about 100 and 200 μm into the scar tissue to treat vocal fold scarring. Note, however, that the depth of the void formation may depend on the subject's extent of scarring. As can be seen in FIG. 16, the fs laser pulses were able to form voids at a depth of about 100 μm beneath the surface of the excised vocal fold tissue, even when using as few as 2 overlapping pulses per spot and a 500 nJ pulse energy. The total surgery duration to form a useful void can be several minutes or less when using a high repetition rate laser and more reasonable endoscopy-capable objectives, e.g., having an NA of about 0.5, that can produce a larger ablation volume from each laser pulse. An exemplary laser having such characteristics can be obtained, e.g., from Raydiance Inc. (500 kHz) (Petaluma, Calif.).

Characterization of the Ablation and Imaging Conditions Using a Single 500 kHz Repetition Rate Laser.

The ablation and imaging parameters can be optimized at different depths using the 500 kHz repetition rate laser (at a wavelength of 776 nm) to form microsurgical voids and collect autofluorescence and SHG images of the same tissue volume before and after laser surgery. A single-laser system for performing microsurgery procedures with a fast ablation rate as well as imaging with an improved imaging depth (as compared to a combination of two laser systems) using a laser with an adjustable pulse rate between, e.g., 1 kHz and 80 MHz can be used. Imaging can be achieved with lower repetition rates (e.g., less than about 80 MHz). Ablation can be accomplished with a repetition rate greater than about 1 kHz. Ablation of a particular area having dimensions of about 3 mm by about 10 mm can be performed in less than 1 minute using the 500 kHz repetition-rate laser (with a surgical spot size of about 1.5 μm diameter and 2-3 overlapping pulses per spot). Ablation of 2D planes below the surface of a vocal fold can be accomplished using a low NA (0.5) objective.

Protocol for Characterizing the Ablated Void and Finding the Optimal Ablation/imaging Conditions To verify the formation of a sub-surface void within the scar tissue, three tests were conducted: (1) visualization of the ablated region using non-linear imaging before and after microsurgery, (2) analysis of the emission spectra of the laser-induced autofluorescence to determine if it exhibits a unique spectral signature that could be used in verifying the success of void creation, and (3) a histopathological analysis performed after fixing the tissue. For assessment of thermal damage, specimens were frozen and cryosectioned for lactate dehydrogenase histochemistry, which demarcates regions of enzyme denaturation.

The SHG signal vanished in the region of ablation and enhanced autofluorescence was consistently observed around the periphery of the ablated void. The lack of an SHG signal and the presence of the laser-induced autofluorescence was observed to correlate with the histopathological analysis of the ablated region.

Characterization and Optimization of the Miniaturized Probe

Two sets of experiments can be performed to characterize the prototype miniaturized probe by: (1) ablation of excised healthy and scarred tissue, and correlation of the observed results with those achieved using a table-top system; and (2) performing surgery in fully intact healthy porcine larynxes obtained from a local slaughterhouse.

First, the capability of the exemplary miniaturized probe to perform surgery and imaging using available maximum power of a 500 kHz laser system can be determined. The maximum imaging and ablation power that can be delivered to the sample may be based on the optical coupling efficiency, the damage threshold of the fiber tip during laser-to-fiber coupling, and insertion losses of the remaining optics.

Second, the performance of the probe can be characterized using fully intact pig larynxes. As with other conventional laryngoscopy procedures, the miniaturized probe can be directed into a subject's throat and positioned against the scarred vocal fold once within the larynx. The surgeries can be performed with the tissue and probe fixed to the optical table. Tissue samples may remain submerged in 0.9% isotonic saline until the experiments are performed to reduce dehydration of the tissue. The probe can then be positioned between the vocal folds, and a substantially planar sub-epithelial void having dimensions of about 3 mm by about 10 mm can be created using the ablative procedure described herein. A Zeitels needle can optionally be used after formation of the void to precisely deliver a fluorescently labeled injectable substance into the region containing the void. A post-surgical scan of the region can then be performed to identify the site of injection and determine the degree of localization of the substance within the formed void.

EXAMPLE 3

Ablative Formation of Planar Voids in Excised Vocal Fold Tissue Using a Picosecond Laser Three samples of calf larynxes containing the vocal fold were obtained. The samples were bisected to allow full view and exposure of the vocal fold and bounding arytenoid and thyroid cartilages. The samples were placed on a flat surface with the vocal fold face-up. Two spacers having the same thickness as the samples were placed on each side of the samples, and a cover glass (160 microns thick) was place on top of the spacers so that it flattened the vocal fold surface. Such flattening can facilitate formation of voids at a uniform depth within the sample, and determination of the depth of the focal point within the tissue samples. The cover glass was in good contact with the tissue sample surface so that no air spaces were present.

Three exemplary procedures were then performed, one on each sample, using a benchtop Nd:YAG 1064 nm, 800 picosecond laser to assess the feasibility of forming ablated sub-epithelial planar voids in vocal folds using a picosecond laser.

Procedure 1.

The Nd:YAG laser was adjusted to provide optical energy pulses having a pulse energy of about 120 mj/pulse as measured at a distance of about 60 mm away from the output of the beam. Two 19 mm diameter achromatic lenses were stacked together and placed in the path of the beam to create a delivered laser spot of about 5.5 mm in diameter at a focal distance of 11.5 mm. The measured energy passing through the lenses was 68 mj/pulse and the pulse repetition rate was 500 Hz.

A computer-controlled mechanical stage scanner was used that was configured to translate the laser apparatus in the X, Y and Z directions at a controlled speed and location along each axis.

An initial location was selected at a depth of about 240 microns within the tissue sample (about 400 microns from the top surface of the cover glass). This depth was achieved by first lowering the activated laser over the cover glass and sample (in the Z direction) until the focal point just contacted the cover glass and etched the top surface. Then, with the laser turned off, the scanner was lowered another 400 microns, so that the focal point of the laser was positioned at a depth of about 260 microns from the surface of the tissue sample.

Starting at this initial location, the laser was turned on and the focal point of the laser beam was scanned 3 mm in the X direction, then shifted 25 microns in the Y direction and translated back 3 mm in the opposite direction along the X axis. This procedure of scanning 3 mm in the X direction, shifting 25 microns in the Y direction, and scanning back 3 mm in the X direction was repeated until a total distance of 3 mm was traversed in the Y direction. This scan pattern created about 120 rows, each 3 mm long and parallel to the X direction, spaced 25 microns apart. The scan speed used in this procedure was 3 mm/sec.

The scanner was then used to return the focal point of the laser to the initial position in the X-Y plane, and to raise the focal point to a depth that was 25 microns higher (i.e., closer to the tissue surface) in the Z direction. The scan pattern described above (25 rows of 3 mm scans spaced 25 microns apart along the Y direction) was then repeated at the shallower depth. This scan pattern was performed a total of 5 times, with each successive scan pattern overlying the previous one and being 25 microns above it within the tissue sample. The time required to produce each scanned layer was about 120 seconds (2 minutes).

Procedure 2.

The positioning and scanning procedures described in Procedure 1 above were performed on a second vocal fold sample. However, the lens arrangement was changed to provide a 14 micron spot size at a focal length of 30 mm. The laser pulses had an energy of 110 mJ/pulse and were delivered at a rate of 500 Hz. The dimensions of the scan pattern (including the 25 micron distance between scan layers) remained the same. However, a total of 6 scan layers were formed (as compared with 5 such layers in Procedure 1 above) to ablate a planar void approximately 3 mm by about 3 mm and about 150 microns thick below the surface of the tissue sample.

Procedure 3.

The positioning and scanning procedures described in Procedure 1 above were performed on a third vocal fold sample, using the same conditions described in Procedure 2 above. However, a total of 8 scan layers were formed in the third tissue sample (as compared with 6 such layers in Procedure 2 above) to ablate a planar void approximately 3 mm by about 3 mm and about 200 microns thick below the surface of the tissue sample.

Void Formation Results.

Figure 18:
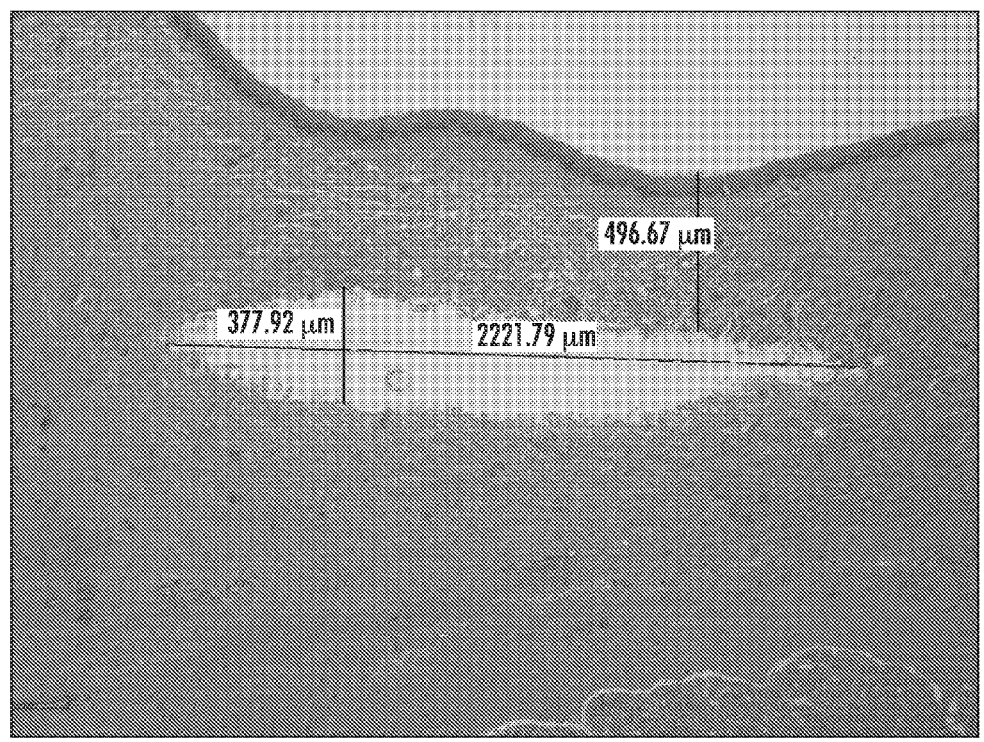
FIG. 18 is an exemplary cross-sectional image of a subepithelial void formed by ablating tissue using a Nd:YAG picosecond laser.

The three irradiated samples were each biopsied and processed for histology at the end of the ablation procedures described above. An exemplary histological image of the void formed in Procedure 2 is shown in FIG. 18. Histological analysis revealed that substantially planar voids were formed in the samples. Further, the epithelium and upper tissue region overlying the voids appeared intact and undamaged. These benchtop procedures demonstrate the feasibility of forming millimeter-scale planar sub-epithelial voids in vocal fold tissue using a picosecond laser in reasonable times (e.g., on the order of several minutes per void). The exemplary systems and methods described herein can be adapted to use a similar laser source, scanning speeds and geometry, etc., to form such ablated sub-epithelial voids using an apparatus having a probe configuration that can be inserted, e.g., directly into a subject's throat to treat vocal folds.

EXAMPLE 4

Ultrafast Laser Microsurgery of Vocal Folds

Experimental Set-up.

Figure 19:
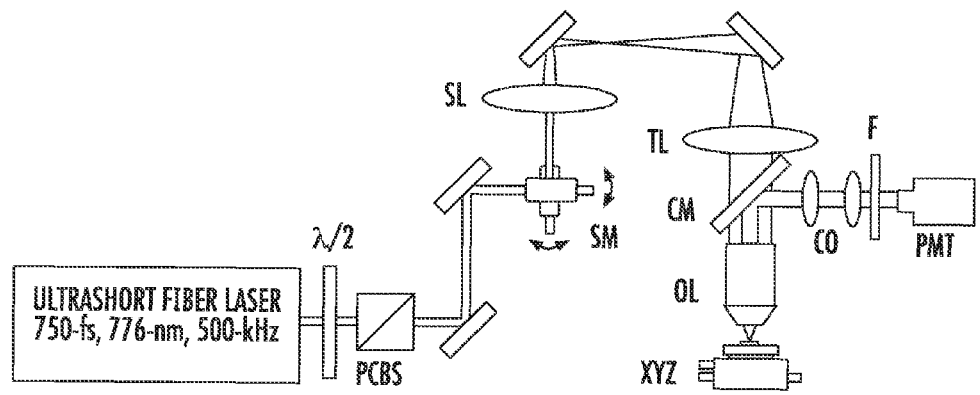
FIG. 19 is a schematic diagram illustrating an exemplary bench-top microsurgery microscope system used for combined imaging and microsurgery.

FIG. 19 is a schematic diagram illustrating an exemplary bench-top microsurgery microscope system used for combined imaging and microsurgery. Femtosecond laser pulses are delivered from a compact fiber laser system to a half-wave plate ($\lambda/2$) and polarizing cube beamsplitter (PCBS) for energy attenuation. The beam is then scanned by a pair of galvanometric scanning mirrors (SM) through a scan lens (SL) and tube lens (TL) that image the mirrors to the back aperture of a 0.75-NA 20× objective lens (OL). The laser is then used to either ablate or image the sample on a three-axis motorized stage (XYZ). Emitted light is redirected by a cold mirror (CM) through collection optics (CO) and a laser-blocking filter (F) to the photomultiplier tube (PMT). The PMT, stage, and scanning mirrors are all in communication with a personal computer through data acquisition cards.

A bench-top microsurgery microscope with nonlinear imaging capabilities as shown in FIG. 19 was used for the procedures presented below. The surgery laser is a 500 kHz repetition rate erbium-doped fiber laser. Optionally, the surgery laser can be a Discovery® model laser Raydiance, Inc. (Petaluma, Calif.). When frequency-doubled, the laser can produce pulses having a wavelength of 776 nm with a duration of 750 fs and a maximum pulse energy of 2.5 µJ. The laser was delivered into a laser scanning microscope and focused at the sample with a 0.75-NA, 20× objective lens for both multiphoton imaging and femtosecond laser microsurgery. The use of 0.75-NA objective provided a spot size of approximately 1.88 µm, which is comparable to the spot sizes achieved in current miniaturized femtosecond laser surgery probes. For microsurgery, the laser beam was scanned by the x-axis of a pair of galvanometric scanning mirrors, while the sample was translated using precision stepper-motor stages in the y-axis for covering a linear distance of either 300 µm or 3 mm of tissue. Optionally, the scanning mirrors can be obtained at Cambridge Technologies, Inc. (Cambridge, Md.). Optionally, the precision stepper-motor stages can be a NanoMax® MAX343 obtained from Thorlabs, Inc. (Newton, N.J.). The use of the motor for the slow axis of ablation was used to extend the maximum length of ablation over what the scanning mirrors could provide using the 20× objective.

The scanning speed and beam deflection of the mirror controlled the degree to which sequential pulses overlapped each other (or the distance between sequential pulses) at the focal plane. The degree of pulse-to-pulse overlap impacted the extent of damage and the speed of ablation. A higher degree of overlap was used to increase pulse-to-pulse accumulation effects to achieve the desired extent of tissue ablation at low pulse energies. However, for a fixed repetition rate, increased pulse overlap decreased the speed of ablation, thus increasing the time for ablating a given region. The duration of the procedure was a factor in development of a clinical technique. To minimize the time to perform the ablation, experiments were performed using 2 overlapping pulses. The laser beam was deflected such that 75% of the focused spot diameter overlapped the spot of the previous pulse. The length of the line scanned by the galvo-mirror on the tissue was chosen to be 300 µm. To achieve 75% pulse-to-pulse overlap with the 300 µm field of view, the mirror scanning speed was 390 Hz, and the translation speed of the y-axis was 0.72 mm/s.

For multiphoton imaging, the laser beam was scanned over a 550 µm×550 µm field of view using both axes of the scanning mirrors, with the emitted light separated from the laser light by a cold mirror and detected by a photomultiplier tube (PMT). Optionally, the cold mirror can be a HT-1.00 cold mirror and can be obtained at CVI Laser (Carlsbad, Calif.). Optionally, the PMT can be a H7422-40 PMT and can be obtained at Hamamatsu (Bridgewater, N.J.). The signal was sampled at 250 kHz to produce a 512×512 pixel image at a frame rate of 0.75 frames per second. This imaging speed roughly corresponds to the same 75% pulse-to-pulse overlap used for the ablation procedure. The laser scanning speed was chosen to be approximately equal for both tissue ablation and imaging because miniaturized beam scanning systems can utilize resonant actuation and exhibit optimum deflection at a particular frequency. The use of the same scanning speed for both imaging and ablation was chosen to demonstrate that both functions could be achieved using a single resonant scanning device in the future.

During imaging, it may be desirable to differentiate two-photon fluorescence (TPF) and second harmonic generation (SHG) signals. To achieve this, a wavelength-tunable femtosecond laser oscillator was used to provide excitation pulses. The wavelength-tunable femtosecond laser oscillator can be a Mai Tai® obtained from Spectra Physics (Irvine, Calif.). Using an 870 nm excitation wavelength and a bandpass filter (436/20 nm) inserted before the PMT, the majority of fluorescence generated at this wavelength was effectively blocked while frequency-doubled signals generated by SHG were collected. The wavelength-tunable laser was used to access the pass-band of the filter.

Ex vivo Tissue Samples.

Frozen whole porcine trachea were acquired, after which the larynx was isolated and the superior vocal fold was thawed in a room-temperature saline bath. Porcine vocal folds have a layered lamina propria very similar in organization and constituents to human vocal folds. The porcine larynx differs slightly from the human larynx in several ways.

First, it has been reported that the porcine vocal fold is more clearly divided into superficial and deep lamina propria (DLP), without an obvious intermediate layer (Garrett et al., Laryngoscope 110:814-24 (2000)). Second, the superior vocal fold of the pig plays the dominant role in phonation, rather than the inferior (or "true") vocal fold, which is dominant in humans (Alipour and Jaiswal, J. Acoustical Soc. Amer. 123:4572-81 (2008)). The superior vocal fold was excised for the experiments. After excision, the vocal fold was placed in saline and covered by a glass coverslip to flatten the upper surface. The use of a coverslip acted to gently flatten the surface of the sample so that a uniform plane could be accessed for experimentation. In a clinical application, the function of the glass coverslip can be performed, e.g., using a window of a microsurgery probe provided in contact with the sample, thus facilitating maintenance of a particular and/or constant depth of ablation. As a result of the freezing process, little cellular autofluorescence was expected from which the surface of the sample could be identified during imaging. To ensure proper identification of the tissue surface, 5 μL of a solution of 1 μm fluorescent beads in saline was deposited onto the tissue surface prior to placement of the coverslip. The fluorescent beads in saline can be 0.002% solids, F-8823 beads and can be obtained from Invitrogen (Carlsbad, Calif.).

Results.

Figure 20:
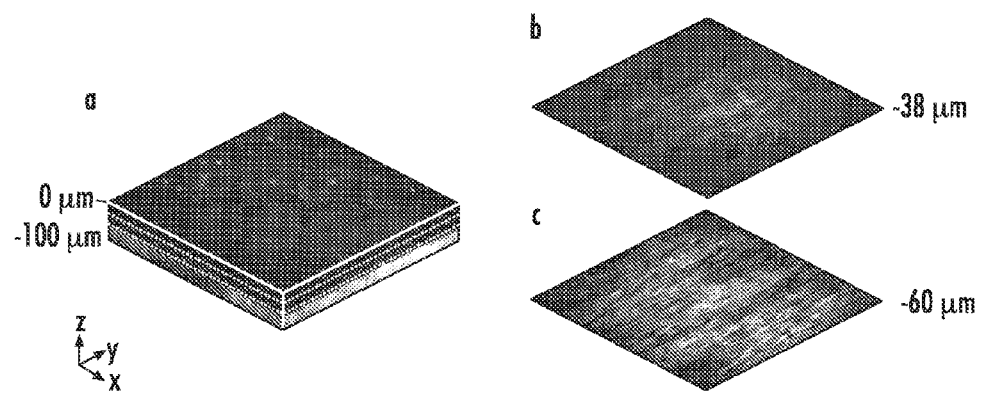
FIG. 20 shows representative nonlinear images of excised porcine fold mucosa.

Nonlinear imaging was used to target the ablation region within the desired tissue architecture of the vocal folds before the ablation procedure and to assess the quality and extent of the ablation after the procedure. FIG. 20 shows a representative image stack through the vocal fold mucosa of one sample before ablation. FIG. 20(a) is a three dimensional reconstruction of an image stack. Each image is based on an average of 5 frames and the separation between each image is 2 μm. The punctuated bright spots on the surface represent the fluorescent beads that were placed for surface identification. Total imaging depth is 100 μm and lateral field of view is 550 μm×550 μm. The dotted lines in FIG. 20(a) represent the planes shown in FIG. 20(b) and FIG. 20(c), at depths of 38 μm and 60 μm below the surface, respectively. The average laser power used during imaging was 0.85 mW at the surface, gradually increasing to 4.35 mW at a depth of 100 μm below the surface. In FIG. 20(c), the imaging plane is entirely within the collagen layer of tissue and the straight, strongly aligned fibers can be seen.

Since no cellular autofluorescence is expected to be present in the superficial layer of samples after the freezing and thawing cycle experienced by the tissue, fluorescent beads were deposited on the surface to facilitate identification of the surface (FIG. 20(a)). As imaging depth was increased, the SHG signal was detected, which appeared to correspond to highly organized and dense collagen fibers. The depth at which the presence of collagen became apparent varied significantly between samples, ranging from 24 μm to 55 μm below the surface (FIG. 20(b)), while the depth at which the image plane was entirely inside the collagen layer varied between 60 μm and 75 μm below the surface (FIG. 20(c)). Identification of the fibers as collagen, rather than elastin was verified using the SHG differentiation protocol described above. The images with and without the filter at constant imaging power demonstrated equal signal intensity, indicating that the signal source was SHG and not TPF. Collagen fibers are well known sources of SHG, whereas, nonlinear optical signals from elastin fibers primarily arise from the more broadband TPF. The collagen observed was determined to be within the SLP layer near the epithelium-SLP interface and was chosen as the desired plane on which to ablate tissue and form a void or pocket.

Sub-surface void formation was investigated by irradiating a series of 300 μm×300 μm squares at the epithelium-SLP interface using pulse energies of 50, 100, 500, and 750 nJ. These energies correspond to fluences of approximately 1.8, 3.6, 18.0, and 27.1 J/cm$^2$, respectfully. The size of the ablation was chosen so that the entire region of interest could be visualized before and after ablation using the 550 μm×550 μm field of view of the multiphoton microscope. Upon imaging after ablation, a void or bubble was considered to have been created when a region of signal loss was observed corresponding to the size and location of the targeted region. Because the source of the collagen imaging signal is SHG, photobleaching can be ruled out as the cause of lost signal in this region. Furthermore, deflection of the surrounding collagen was observed when forming larger voids, which supports the hypothesis that bubble expansion occurred rather than a photochemical depolymerization of collagen.

Figure 21:
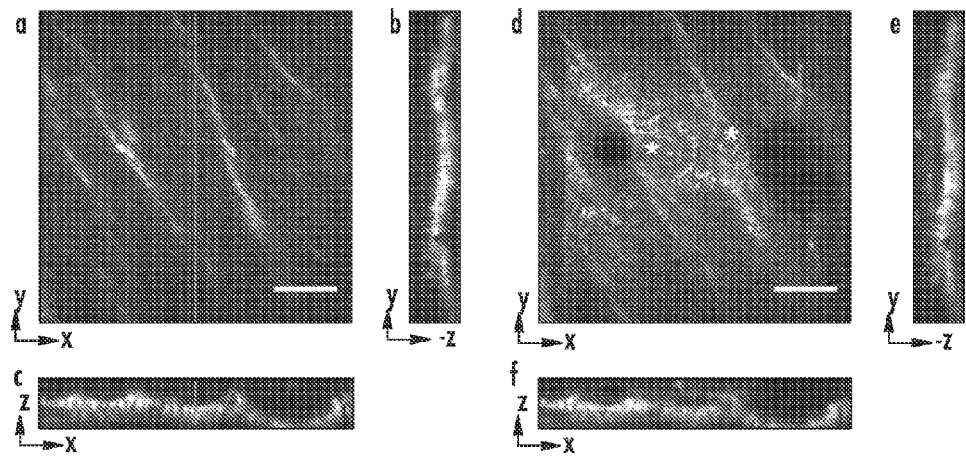
FIG. 21 shows representative images following irradiation using 100 nJ pulses.

FIG. 21 shows representative images following irradiation using 100 nJ pulses. FIG. 21(a) is an image of the plane targeted for ablation immediately prior to irradiation. The horizontal and vertical lines in FIG. 21(a) denote sectioning lines corresponding to the cross-sectional images of FIG. 21(b) and FIG. 21(c), respectively. FIG. 21(d) represents the same field of view as shown in FIG. 21(a), 1 minute after irradiation with 100 nJ pulses. An approximately square region of induced luminescence at the ablated region and two circular regions corresponding to areas of localized bubble nucleation during irradiation can be observed. White asterisks are provided in FIG. 21(d) immediately to the right of two regions that appear to be disrupted collagen fibers, suggesting a thin sub-resolution plane may have been disrupted at this energy. The horizontal and vertical lines in FIG. 21(d) denote the sectioning lines corresponding to the cross-sectional images of FIG. 21(e) and FIG. 21(f), respectively. Arrows indicate fluorescent scarring that is apparent in the cross-sectional images. Imaging depth in both sets of images is 80 μm. The length of the white scale bars in FIGS. 21(a) and 21(d) are 100 μm.

FIG. 21 presents a representative example of a sample ablated with 100 nJ pulses. No voids were observed using 50 nJ pulses; however, irradiation with 100 nJ pulses produced very thin planes of induced luminescence and occasionally small localized voids within the ablation region. The increased luminescence was found to accompany void formation at all pulse energies investigated and was observed originating from the periphery of the ablated region. Induced luminescence resulting from irradiation using 100 nJ pulses can be observed when comparing the cross sectional images before and after ablation, FIGS. 21(b) and 21(c) and FIGS. 21(e) and 21(f), respectively. When a notch filter was employed to filter out broadband fluorescent emission as before, this luminescence signal was not detected. It is hypothesized that the observed broad-band emission was fluorescent in nature rather than due to an enhancement or generation of second harmonic signal. This luminescence ring appeared long-lived and could still be observed one hour after ablation. Although the mechanism behind the increased luminescence is not known with certainty, this phenomenon has been observed by several other groups using fluorescence imaging to visualize femtosecond laser ablation of tissue and has been referred to as "fluorescent scarring." In clinical applications utilizing ablation monitoring with nonlinear imaging, the fluorescent scarring may be used as a signal source to determine the extent of successful ablation.

At low fluences near the damage threshold, the extent of ablation is smaller than the spot size of the focused laser beam. The focusing conditions for imaging may be similar to those for surgery. The smaller voids that were occasionally formed in the tissue when using 100 nJ pulses often were observed in areas irradiated at the beginning or ending of the ablation procedure and may result from an increased energy exposure in these areas. Less frequently, small bubbles were observed in the middle of the region of ablation. These bubbles may result from inhomogeneities in the tissue giving rise to a slightly lower breakdown threshold in certain places. Both types of bubbles or small voids can be seen in the example shown in FIG. 21(d). The presence of fluorescent scarring and occasional bubble nucleation indicates that the tissue was modified when using pulses as low as 100 nJ; however, complete ablation of the scanned regions at this pulse energy or lower pulse energies can be verified using a secondary means, such as histology.

Generally, higher pulse energies resulted in the formation of larger voids inside the tissue. Using 500 and 750 nJ pulses, large voids were created that covered the scanned region of ablation and extending above and below the plane of ablation. These large voids may arise from long-lived bubbles created at the plane of ablation that may merge and expand, displacing the tissue above and below the ablation plane. The formation of bubbles that expand beyond the focal volume was consistent with previous observations of femtosecond laser ablation well above the optical breakdown threshold, where increased pulse energy beyond the threshold led to increased maximum bubble diameter and the vaporization of biomolecules produced an amount of gas that cannot be condensed and diffuses into the surrounding tissue, leading to longer bubble lifetimes (Vogel et al., Applied Physics B 81:1015-47 (2005)).

Figure 22:
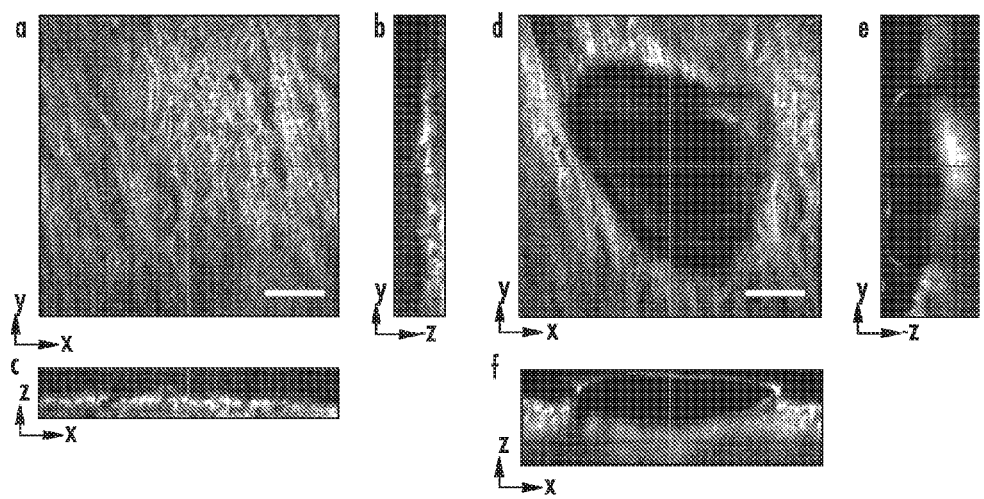
FIG. 22 shows representative sub-surface void formation using 500 nJ pulses.

FIG. 22 illustrates a representative ablation procedure using 500 nJ pulses. In this example, the sub-surface void has maximum dimensions in the ablation plane of 350 µm×390 µm, and has a maximum height of 90 µm. FIG. 22(a) shows an image of the plane targeted for ablation immediately prior to irradiation. The horizontal and vertical lines in FIG. 22(a) denote sectioning lines corresponding to the cross-sectional images of FIG. 22(b) and FIG. 22(c), respectively. The imaging depth was 80 µm. FIG. 22(d) is an image of the same plane as in FIG. 22(a) approximately 1 minute after irradiation of the target region with 500 nJ pulses. The horizontal and vertical lines represent sectioning lines corresponding to the cross-sectional images of FIG. 22(e) and FIG. 22(f), respectively. To fully capture the extent of the formed void, the imaging depth was increased to 160 µm. Fluorescent scarring is apparent at the periphery of the ablated void in FIG. 22(e) and FIG. 22(f). The white scale bars in FIGS. 22(a) and 22(d) are 100 µm.

Figure 23:
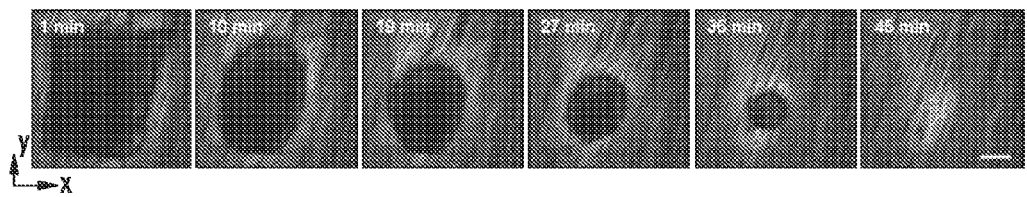
FIG. 23 shows representative time-lapse images after ablation using 750 nJ pulses.

FIG. 23 shows representative time-lapse images after ablation of tissue using 750 nJ pulses. The images were obtained from an x-y plane located 15 µm below the targeted ablation plane. Time stamps in the upper left corner denote how much time has elapsed since irradiation with 750 nJ pulses. In the first image, a large void was observed, corresponding roughly to the size and shape of irradiation but clearly extending below the targeted ablation plane. As time progresses, the void appeared to recede, allowing the collagen that had been compressed to return to the field of view. The void initially measured approximately 350 µm×400 µm in the targeted ablation plane and extended 40 µm and 45 µm above and below this plane, respectively. Over 45 minutes, the bubble was observed to collapse until it measured only 40 µm at its thickest point.

Figure 24:
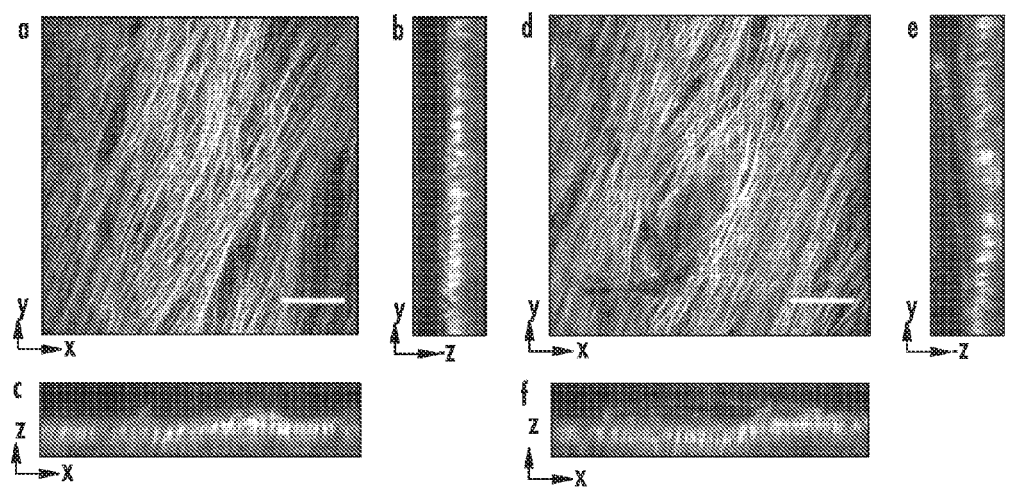
FIG. 24 shows representative images of sub-surface void formation using 750 nJ pulses.

FIG. 24 shows representative images of sub-surface void formation using 750 nJ pulses. FIG. 24(a) is an image of the plane targeted for ablation immediately prior to irradiation. The horizontal and vertical lines denote sectioning lines corresponding to the cross-sectional images of FIG. 24(b) and FIG. 24(c), respectively. After irradiation with 750 nJ pulses, a large void was observed which then collapsed over 45 minutes. FIG. 24(d) is an image of the plane targeted for ablation approximately 45 minutes after irradiation, e.g., after collapse of the formed void was substantially complete. The horizontal and vertical lines denote sectioning lines corresponding to the cross-sectional images of FIG. 24(e) and FIG. 24(f), respectively. Fluorescent scarring at the periphery of the ablated void is apparent in FIG. 24(e) and FIG. 24(f). Also, tilting of the void can be observed in the y-z plane in FIG. 24(e). During ablation, the laser began scanning at the bottom of the image and ended at the top. The apparent rise of the ablation during the ablation process is thought to be due to the interaction of incoming laser pulses with the pre-existing bubble from previous pulses. Imaging depth in both sets of images is 120 µm. The white scale bars in FIGS. 24(a) and 24(d) are 100 µm.

The remaining void, shown in FIG. 24(d)-(f), was observed to have an area of approximately 320 µm×350 µm, similar to the dimensions of the target area scanned by the laser. However, the planar void exhibited a tilt out of the plane of ablation toward the surface of the tissue. Over the 350 µm extent of the ablation, the void rose just over 50 µm and almost broke the plane of the tissue surface. No such tilt was observed in the fluorescent scarring when ablation was performed using 100 nJ pulses, which indicates that tilting of the sample stage was not the source of observed tilt in the ablated void. This tilt may have been caused by incoming ablative energy pulses interacting with the long-lived bubbles formed by the previous high-energy pulses.

What is claimed is:

1. A method of treating a vocal fold pathology, comprising:
focusing pulsed laser light using a lens into a sub-epithelial focal volume of the vocal fold; wherein the pulse duration of the laser light is a nanosecond or less and wherein the pulsed light has a wavelength of between 600 nm and 2250 nm;
wherein the focused pulsed laser light ablates sub-epithelial tissue of the vocal fold in the focal volume to form a sub-epithelial void in the vocal fold and wherein tissue ablation caused by the laser light of the vocal fold tissue is confined to the sub-epithelial focal volume; and
directing a substance into the sub-epithelial void, wherein the substance is confined within the sub-epithelial void to treat the vocal fold pathology.

2. The method of claim 1, wherein a length and a width of the sub-epithelial void as measured substantially parallel to the surface of the vocal fold are each at least about 1 millimeter in length.

3. The method of claim 2, wherein the length and the width of the sub-epithelial void are at least about 2 millimeters.

4. The method of claim 2, wherein the sub-epithelial void is formed at a depth of between about 100 and 200 microns below the epithelial layer of the vocal fold.

5. The method of claim 1, wherein the sub-epithelial void is formed above a scar tissue in the vocal fold.

6. The method of claim 1, wherein the sub-epithelial void is formed within a scar tissue in the vocal fold.

7. The method of claim 1, wherein the pulsed laser light is provided by an optical energy source.

8. The method of claim 7, wherein the optical energy source comprises a picosecond laser.

9. The method of claim 7, wherein the optical energy source comprises a femtosecond laser.

10. The method of claim 7, further comprising:
applying optical energy to the vocal fold within the subject, wherein the optical energy is configured for imaging at least a portion of the vocal fold;
receiving light from the vocal fold; and
generating an image of the vocal fold based on the received light.

11. The method of claim 10, further comprising forming the sub-epithelial void at a location based on the image.

12. The method of claim 1, wherein the substance is a biomaterial.

13. The method of claim 12, wherein the biomaterial comprises at least one of collagen, polymeric gel, fat, or hyaluronic acid.

\* \* \* \* \*